US012694263B2

(12) United States Patent
Gong et al.

(10) Patent No.: US 12,694,263 B2
(45) Date of Patent: Jul. 28, 2026

(54) MODELLING CAUSATION IN MACHINE LEARNING

(71) Applicant: Microsoft Technology Licensing, LLC, Redmond, WA (US)

(72) Inventors: Wenbo Gong, Cambridge (GB); Cheng Zhang, Cambridge (GB); Nick Pawlowski, Cambridge (GB); Joel Jennings, Cambridge (GB); Karen Fassio, Bremerton, WA (US); Marife Defante, Woodinville, WA (US); Steve Thomas, Redmond, WA (US); Alice Horan, Redmond, WA (US); Chao Ma, Cambridge (GB); Matthew Ashman, Cambridge (GB); Agrin Hilmkil, Stockholm (SE)

(73) Assignee: Microsoft Technology Licensing, LLC, Redmond, WA (US)

( * ) Notice: Subject to any disclaimer, the term of this patent is extended or adjusted under 35 U.S.C. 154(b) by 839 days.

(21) Appl. No.: 17/936,347

(22) Filed: Sep. 28, 2022

(65) Prior Publication Data

US 2024/0104338 A1 Mar. 28, 2024

Related U.S. Application Data

(60) Provisional application No. 63/376,550, filed on Sep. 21, 2022.

(51) Int. Cl.
G06N 3/04 (2023.01)
G06N 3/0455 (2023.01)
(Continued)

(52) U.S. Cl.
CPC ............. G06N 3/04 (2013.01); G06N 3/0455 (2023.01); G06N 3/084 (2013.01); G06N 7/01 (2023.01); G16H 20/00 (2018.01); *G16H 50/20* (2018.01)

(58) Field of Classification Search
CPC .......... G06N 3/04; G06N 3/045; G06N 3/088; G06N 3/0455; G06N 3/084; G06N 20/20; (Continued)

(56) References Cited

U.S. PATENT DOCUMENTS 7,117,185 B1 * 10/2006 Aliferis .................. G06N 20/00
706/14
10,699,450 B2 * 6/2020 Weissbrod ............ G06F 3/0482
(Continued)

FOREIGN PATENT DOCUMENTS

WO WO-2007144804 A1 * 12/2007 ............. G16H 50/20

OTHER PUBLICATIONS

Liu, Yan, et al. "Learning temporal causal graphs for relational time-series analysis." Proceedings of the 27th International Conference on Machine Learning (ICML-10). 2010. (Year: 2010).*
(Continued)

*Primary Examiner* — Andrew L Tank
(74) *Attorney, Agent, or Firm* — Barta Jones, PLLC

(57) ABSTRACT
A method comprising: sampling a temporal causal graph from a temporal graph distribution specifying probabilities of directed causal edges between different variables of a feature vector at a present time step, and from one variable at a preceding time step to another variables at the present time step. Based on this there are identified: a present parent which is a cause of the selected variable in the present time step, and a preceding parent which is a cause of the selected variable from the preceding time step. The method then comprises: inputting a value of each identified present and
(Continued)

preceding parent into a respective encoder, resulting in a respective embedding of each of the present and preceding parents; combining the embeddings of the present and preceding parents, resulting in a combined embedding; inputting the combined embedding into a decoder, resulting in a reconstructed value of the selected variable.

20 Claims, 14 Drawing Sheets

(51) Int. Cl.

| | |
|---|---|
| G06N 3/084 | (2023.01) |
| G06N 7/01 | (2023.01) |
| G16H 20/00 | (2018.01) |
| G16H 50/20 | (2018.01) |

(58) Field of Classification Search
CPC ............ G06N 5/025; G06N 5/01; G06N 7/01; G16H 50/20; G16H 50/50; G16H 20/00; G16H 50/70; G06F 17/18; G06F 18/29
See application file for complete search history.

(56) References Cited

U.S. PATENT DOCUMENTS

| | | | | |
|---|---|---|---|---|
| 11,468,348 | B1 | 10/2022 | Cui | |
| 12,034,747 | B2 * | 7/2024 | Raghavendra | G06N 20/00 |
| 2009/0006289 | A1 * | 1/2009 | Jaros | G06N 3/049 |
| | | | | 706/12 |
| 2011/0112998 | A1 * | 5/2011 | Abe | G06N 7/01 |
| | | | | 706/13 |
| 2011/0167031 | A1 * | 7/2011 | Kleinberg | G06N 5/04 |
| | | | | 706/46 |
| 2013/0046721 | A1 * | 2/2013 | Jiang | G06N 7/01 |
| | | | | 706/47 |
| 2016/0292248 | A1 * | 10/2016 | Garcia | G06Q 10/063 |
| 2017/0220937 | A1 * | 8/2017 | Wada | G06F 16/2228 |
| 2019/0326019 | A1 * | 10/2019 | Ramazzotti | G06N 20/00 |
| 2020/0233920 | A1 * | 7/2020 | Meeds | G06V 20/698 |
| 2020/0245009 | A1 * | 7/2020 | Saini | H04N 21/23614 |
| 2020/0279417 | A1 | 9/2020 | Lee | |
| 2021/0064517 | A1 * | 3/2021 | Wong | G06F 11/3698 |
| 2021/0256406 | A1 * | 8/2021 | Lau | G06N 7/01 |
| 2021/0295955 | A1 | 9/2021 | Lee et al. | |
| 2022/0093271 | A1 * | 3/2022 | Huang | G06N 7/01 |
| 2023/0065173 | A1 * | 3/2023 | Shibahara | G16H 20/10 |
| 2023/0072173 | A1 * | 3/2023 | Gupta | G16H 50/70 |
| 2023/0128111 | A1 * | 4/2023 | Greenewald | G06F 17/18 |
| | | | | 705/2 |
| 2023/0229906 | A1 | 7/2023 | Zhang et al. | |
| 2023/0359867 | A1 * | 11/2023 | Park | G06N 3/084 |
| 2023/0376734 | A1 * | 11/2023 | Liu | G06N 3/045 |
| 2023/0401423 | A1 * | 12/2023 | Sim | G06N 20/00 |
| 2024/0047042 | A1 * | 2/2024 | Daza | G16H 50/20 |
| 2024/0104370 | A1 | 3/2024 | Ma | |
| 2024/0126945 | A1 * | 4/2024 | Bellot | G06F 30/20 |

OTHER PUBLICATIONS

Gong, Mingming, et al. "Causal discovery from temporally aggregated time series." Uncertainty in artificial intelligence: proceedings of the . . . conference. Conference on Uncertainty in Artificial Intelligence. vol. 2017. 2017. (Year: 2017).*

Gootjes-Dreesbach, Luise, et al. "Variational autoencoder modular Bayesian networks for simulation of heterogeneous clinical study data." Frontiers in big Data 3 (2020): 16. (Year: 2020).*

Zhang, Xin, and Jiali You. "A gated dilated causal convolution based encoder-decoder for network traffic forecasting." IEEE Access 8 (2020): 6087-6097. (Year: 2020).*

Wang, Yanbang, et al. "Inductive representation learning in temporal networks via causal anonymous walks." arXiv preprint arXiv: 2101.05974v1 (2021). (Year: 2021).*

Berrevoets, Jeroen, et al. "Disentangled counterfactual recurrent networks for treatment effect inference over time." arXiv preprint arXiv:2112.03811v1 (2021). (Year: 2021).*

Kaddour, Jean, et al. "Causal effect inference for structured treatments." Advances in Neural Information Processing Systems 34 (2021): 24841-24854. (Year: 2021).*

Moraffah, Raha, et al. "Causal Inference for Time series Analysis: Problems, Methods and Evaluation." arXiv preprint arXiv: 2102. 05829v1 (2021). (Year: 2021).*

Chen, Y., Zhang, J. & Qin, X. Interpretable instance disease prediction based on causal feature selection and effect analysis. BMC Med Inform Decis Mak 22, 51 (2022). https://doi.org/10. 1186/s12911-022-01788-8 (Year: 2022).*

Wang, L., Adiga, A., Chen, J., Sadilek, A., Venkatramanan, S., & Marathe, M. (Jun. 2022). Causalgnn: Causal-based graph neural networks for spatio-temporal epidemic forecasting. In Proceedings of the AAAI conference on artificial intelligence (vol. 36, No. 11, pp. 12191-12199). (Year: 2022).*

Wang, Xinyue, et al. "Meta-learning Causal Discovery." arXiv preprint arXiv:2209.05598v1 (2022) (Year: 2022).*

Zhang, Tao, Hao-Ran Shan, and Max A. Little. "Causal GraphSAGE: A robust graph method for classification based on causal sampling." Pattern recognition 128 (2022): 108696. (Year: 2022).*

Amornbunchornvej, et al., "Variable-Lag Granger Causality for Time Series Analysis", In Proceedings of IEEE International Conference on Data Science and Advanced Analytics (DSAA), Oct. 5, 2019, pp. 21-30.

Bellot, et al., "Deconfounded Score Method: Scoring DAGs with Dense Unobserved Confounding", In Repository of arXiv:2103. 15106v2, May 25, 2021, 19 Pages.

Zhang, et al., "On the Identifiability of the Post-Nonlinear Causal Model", In Repository of arXiv:1205.2599v1, May 9, 2012, pp. 647-655.

Bhattacharya, et al., "Differentiable Causal Discovery Under Unmeasured Confounding", In Proceedings of The 24th International Conference on Artificial Intelligence and Statistics, PMLR, Apr. 13, 2021, 11 Pages.

Blei, et al., "Variational Inference: A Review for Statisticians", In Journal of The American Statistical Association, vol. 112, Issue 518, Feb. 27, 2017, pp. 859-877.

Bussmann, et al., "Neural Additive Vector Autoregression Models for Causal Discovery in Time Series", In Proceedings of International Conference on Discovery Science, Oct. 9, 2021, pp. 446-460.

Bussmann, et al., "Neural Additive Vector Autoregression Models for Causal Discovery in Time Series", In Repository of arXiv:2010. 09429v2, Oct. 18, 2021, 18 Pages.

Cai, et al., "Triad Constraints for Learning Causal Structure of Latent Variables", In Proceedings of Advances in Neural Information Processing Systems, vol. 32, Dec. 8, 2019, 10 Pages.

Dang, et al., "seq2graph: Discovering Dynamic Dependencies from Multivariate Time Series with Multi-level Attention", In Repository of arXiv:1812.04448v1, Dec. 7, 2018, 9 Pages.

Durkan, et al., "Neural Spline Flows", In Proceedings of Advances in Neural Information Processing Systems, vol. 32, Dec. 8, 2019, 12 Pages.

Geffner, et al., "Deep End-to-end Causal Inference", In Repository of arXiv:2202.02195v2, Jun. 20, 2022, 31 Pages.

Geffner, et al., "FCause: Flow-based Causal Discovery", Retrieved From: https://openreview.net/attachment?id=HO_LL-oqBzW&name= pdf, Sep. 29, 2021, 19 Pages.

Glymour, et al., "Review of Causal Discovery Methods Based on Graphical Models", In Journal of Frontiers in Genetics, vol. 10, Article 524, Jun. 4, 2019, 15 Pages.

Granger, Clivew. , "Investigating Causal Relations by Econometric Models and Cross-spectral Methods", In Journal of Econometrica, vol. 37, Issue 3, Aug. 1, 1969, pp. 424-438.

Guo, et al., "A Survey of Learning Causality with Data: Problems and Methods", In Proceedings of ACM Computing Surveys, vol. 53, Issue 4, Jul. 22, 2020, 37 Pages.

Heckerman, et al., "A Bayesian Approach to Causal Discovery", In Publication of Springer Berlin Heidelberg, 2006, 28 Pages.

(56) References Cited

OTHER PUBLICATIONS

Hoyer, et al., "Nonlinear Causal Discovery with Additive Noise Models", In Proceedings of Advances in Neural Information Processing Systems (NIPS), vol. 21, Dec. 8, 2008, 8 Pages.

Hyvärinen, et al., "Estimation of a Structural Vector Autoregression Model Using Non-Gaussianity", In Journal of Machine Learning Research, vol. 11, May 1, 2010, pp. 1709-1731.

Jang, et al., "Categorical Reparameterization with Gumbel-Softmax", In Repository of arXiv:1611.01144v1, Nov. 3, 2016, 13 Pages.

Kaiser, et al., "Unsuitability of NOTEARS for Causal Graph Discovery", In Repository of arXiv:2104.05441v1, Apr. 12, 2021, 5 Pages.

Zheng, et al., "DAGs with NO Tears: Continuous Optimization for Structure Learning", In Proceedings of Advances n Neural Information Processing Systems, vol. 31, Dec. 3, 2018, 12 Pages.

Lippe, et al., "Efficient Neural Causal Discovery without Acyclicity Constraints", In Repository of arXiv:2107.10483v1, Jul. 22, 2021, 34 Pages.

Löwe, et al., "Amortized Causal Discovery: Learning to Infer Causal Graphs from Time-Series Data", In Proceedings of Machine Learning Research, vol. 140, Apr. 11, 2022, 17 Pages.

Maathuis, et al., "Handbook of Graphical Models", In Publication of CRC Press, Nov. 12, 2018, 546 Pages.

Maddison, et al., "The Concrete Distribution: A Continuous Relaxation of Discrete Random Variables", In Repository of arXiv:1611.00712v2, Nov. 6, 2016, 17 Pages.

Monti, et al., "Autoregressive Flow-Based Causal Discovery and Inference", In Repository of arXiv:2007.09390v1, Jul. 18, 2020, 6 Pages.

Moraffah, et al., "Causal Inference for Time Series Analysis: Problems, Methods and Evaluation", In Journal of Knowledge and Information Systems, vol. 63, Nov. 23, 2021, pp. 3041-3085.

Naser, et al., "Causality, Causal Discovery, and Causal Inference in Structural Engineering", In Repository of arXiv:2204.01543v3, Aug. 8, 2022, 27 Pages.

Ness, et al., "A Bayesian Active Learning Experimental Design for Inferring Signaling Networks", In Proceedings of International Conference on Research in Computational Molecular Biology, May 3, 2017, 11 Pages.

Pamfil, et al., "DYNOTEARS: Structure Learning from Time-Series Data", In Repository of arXiv:2002.00498v2, Apr. 27, 2020, 23 Pages.

Pamfil, et al., "DYNOTEARS: Structure Learning from Time-Series Data", In Proceedings of International Conference on Artificial Intelligence and Statistics, Aug. 26, 2020, 10 Pages.

Pawlowski, et al., "Deep Structural Causal Models for Tractable Counterfactual Inference", In Proceedings of Advances in Neural Information Processing Systems, vol. 33, Dec. 6, 2020, 13 Pages.

Pearl, Judea, "Causal Inference in Statistics: An Overview", In Journal of Statistics Surveys, vol. 3, Oct. 13, 2009, pp. 96-146.

Pena, Jose M. , "Learning Acyclic Directed Mixed Graphs from Observations and Interventions", In Proceedings of the Eighth International Conference on Probabilistic Graphical Models, PMLR, vol. 52, Sep. 6, 2016, pp. 392-403.

Pena, Josem. , "Reasoning with Alternative Acyclic Directed Mixed Graphs", In Journal of Behaviormetrika, vol. 45, Issue 2, Oct. 2018, pp. 389-422.

Peters, et al., "Causal Inference on Time Series using Restricted Structural Equation Models", In Proceedings of Advances in Neural Information Processing Systems, vol. 26, Dec. 5, 2013, 9 Pages.

Peters, et al., "Causal Inference on Time Series using Structural Equation Models", In Repository of arXiv:1207.5136v1, Jul. 21, 2012, 11 Pages.

Peters, et al., "Elements of Causal Inference: Foundations and Learning Algorithms", Published by MIT Press, Nov. 29, 2017, 289 Pages.

Peters, et al., "Identifiability of Causal Graphs using Functional Models", In Repository of arXiv:1202.3757v1, Feb. 14, 2012, 10 Pages.

Reisach, et al., "Beware of the Simulated DAG! Varsortability in Additive Noise Models", In Repository of arXiv:2102.13647v1, Feb. 26, 2021, 19 Pages.

Richardson, Thomas, "Markov Properties for Acyclic Directed Mixed Graphs", In Scandinavian Journal of Statistics, vol. 30, No. 1, Feb. 28, 2003, pp. 145-157.

Runge, Jakob, "Causal network reconstruction from time series: From theoretical assumptions to practical estimation", In Journal of Chaos: An Interdisciplinary Journal of Nonlinear Science, vol. 28, Issue 7, Jul. 24, 2018, 20 Pages.

Shojaie, et al., "Discovering Graphical Granger Causality Using the Truncating Lasso Penalty", In Journal of Bioinformatics, vol. 26, Issue 18, Sep. 15, 2010, pp. 1517-i523.

Siggiridou, et al., "Granger Causality in Multivariate Time Series Using a Time-Ordered Restricted Vector Autoregressive Model", In Journal of IEEE Transactions on Signal Processing, vol. 64, Issue 7, Apr. 2016, pp. 1759-1773.

Spirtes, et al., "Causation, Prediction, and Search", In Publication of MIT Press, 2000, 546 Pages.

Tank, et al., "Neural Granger Causality for Nonlinear Time Series", In Journal of Stat, vol. 1050, Feb. 19, 2018, 18 Pages.

Tian, et al., "A General Identification Condition for Causal Effects", In Publication of eScholarship, University of California, Aug. 1, 2002, pp. 567-573.

Trippe, et al., "Conditional Density Estimation with Bayesian Normalising Flows", In Repository of arXiv:1802.04908v1, Feb. 14, 2018, 19 Pages.

Wu, et al., "Discovering Nonlinear Relations with Minimum Predictive Information Regularization", In Repository of arXiv:2001.01885v1, Jan. 7, 2020, 26 Pages.

Xu, et al., "Scalable Causal Graph Learning through a Deep Neural Network", In Proceedings of the 28th ACM International Conference on Information and Knowledge Management, Nov. 3, 2019, 10 Pages.

International Search Report and Written Opinion received for PCT Application No. PCT/US2023/031000, Dec. 15, 2023, 19 pages.

International Search Report and Written Opinion received for PCT Application No. PCT/US23/031103, mailed on Jan. 9, 2024, 14 pages.

Lowe S., et al., "Amortized Causal Discovery: Learning to Infer Causal Graphs from Time-Series Data," arxiv.org, Cornell University Library, 201 Olin Library Cornell University Ithaca, NY 14853, Feb. 21, 2022, 27 pages.

Meng Y., "Estimating Granger Causality with Unobserved Confounders via Deep Latent-Variable Recurrent Neural Network," arxiv.org, Cornell University Library, 201 Olin Library, Cornell University Ithaca, NY 14853, Sep. 9, 2019, 9 pages.

Wang, et al., "Estimating Individualized Causal Effect with Confounded Instruments", Proceedings of the 2020 5th International Conference on Big Data and computing, Aug. 14, 2022, pp. 1857-1867.

Zecevic M., et al., "Relating Graph Neural Networks to Structural Causal Models," arxiv.org, Cornell University Library, 201 Olin Library, Cornell University Ithaca, NY 14853, Oct. 22, 2021, 29 pages.

"International Search Report and Written Opinion Issued in PCT Application No. PCT/US23/010159", Mailed Date: Apr. 19, 2023, 11 Pages.

Chen et al., "Heterogeneous Treatment Effect Estimation through Deep Learning", arXiv:1810.11010v1, Oct. 25, 2018, 26 pages.

Fehner, Gerald, "Estimating casual effects of credit decisions", International Journal of Forecasting, vol. 28, 2012, pp. 248-260.

International Preliminary Report on Patentability received for PCT Application No. PCT/US2023/031000, Apr. 3, 2025, 14 pages.

International Preliminary Report on Patentability received for PCT Application No. PCT/US23/031103, mailed on Apr. 3, 2025, 10 pages.

Non-Final Office Action mailed on Apr. 22, 2025, in U.S. Appl. No. 17/579,877, 59 pages.

Sanchez-Martin, et al., "VACA: Design of Variational Graph Autoencoders for Interventional and Counterfactual Queries", arXiv:210.14690v1, Oct. 27, 2021, 31 pages.

(56)          References Cited

OTHER PUBLICATIONS

Zheng, et al., "DAGs with NO Tears: Smooth Optimization for Structure Learning", In Repository of arXiv:1803.01422v1, Mar. 4, 2018, 14 Pages.

Zhang, et al., "Advances in Variational Inference", In Journal of IEEE Transactions on Pattern Analysis and Machine Intelligence, vol. 41, Issue 8, Dec. 24, 2018, pp. 2008-2026.

Zhang, et al., "On Estimation of Functional Causal Models: General Results and Application to the Post-Nonlinear Causal Model", In Journal of ACM Transactions on Intelligent Systems and Technology (TIST), vol. 7, No. 2, Dec. 17, 2015, 23 Pages.

Final Office Action mailed on Jan. 8, 2026, in U.S. Appl. No. 17/936,338, 26 Pages.

Zheng, et al., "Dags with No. tears: Continuous optimization for structure learning", arXiv:1803.01422, Nov. 3, 2018, 22 pages.

Mireshghallah, et al., "Privacy in Deep Learning: A Survey", In Repository of arXiv:2004.12254, Version.5, Nov. 7, 2020, 24 Pages.

Non-Final Office Action mailed on Sep. 8, 2025, in U.S. Appl. No. 17/936,338, 39 Pages.

Sharp, et al., "Creating Causal Embeddings for Question Answering with Minimal Supervision", In Repository of arXiv:1609.08097v1, Sep. 26, 2016, 11 Pages.

Zecevic, et al., "Relating Graph Neural Networks to Structural Causal Models", In Repository of arXiv:2109.04173, vol. 3, Oct. 22, 2021, 29 Pages.

Final Office Action mailed on Nov. 13, 2025, in U.S. Appl. No. 17/579,877, 71 Pages.

First Examination Report Received for Indian Application No. 202417053257, mailed on Nov. 21, 2025, 07 Pages.

Summer Institute in Computational Social Science, "Tutorial on deep learning for causal inference", Retrieved from URL: https://www.youtube.com/watch?v=v9uf9rDYEMg, Published on: Jun. 25, 2021, 01 Page.

Yu, et al., "Dag-gnn: Dag structure learning with graph neural networks", In Proceedings of the 36th International Conference on Machine Learning, 2019, 10 pages.

Notice of Allowance mailed on Apr. 15, 2026, in U.S. Appl. No. 17/936,338, 18 Pages.

Kuipers, et al., "Efficient and Structure Learning of Bayesian Networks", In Repository of arXiv:1803.07859v4, Nov. 9, 2021, 41 Pages.

Non-Final Office Action mailed on May 14, 2026, in U.S. Appl. 17/579,877, 37 Pages.

* cited by examiner

Unobserved cause        Treatment $x_1$        $x_4$

Inference $x_2$        $x_3$

Observed condition        Effect

104

$i=1...D$        $G \sim q_\phi$ h → $x_1$ → $g^e_1$ → $e_1$

...

$x_2$ → $g^e_2$ → $e_2$ $x_D$ → $g^e_D$ → $e_D$

1

MODELLING CAUSATION IN MACHINE LEARNING

CROSS-REFERENCE TO RELATED APPLICATION

This application claims the benefit of U.S. provisional application No. 63/376,550 filed on Sep. 21, 2022, entitled "MODELLING CAUSATION IN MACHINE LEARNING," the entirety of which is hereby incorporated by reference herein.

BACKGROUND

Neural networks are used in the field of machine learning and artificial intelligence (AI). A neural network comprises plurality of nodes which are interconnected by links, sometimes referred to as edges. The input edges of one or more nodes form the input of the network as a whole, and the output edges of one or more other nodes form the output of the network as a whole, whilst the output edges of various nodes within the network form the input edges to other nodes. Each node represents a function of its input edge(s) weighted by a respective weight, the result being output(s) on its output edge(s). The weights can be gradually tuned based on a set of training data so as to tend towards a state where the output of the network will output a desired value for a given input.

Typically the nodes are arranged into layers with at least an input and an output layer. A "deep" neural network comprises one or more intermediate or "hidden" layers in between the input layer and the output layer. The neural network can take input data and propagate the input data through the layers of the network to generate output data. Certain nodes within the network perform operations on the data, and the result of those operations is passed to other nodes, and so on.

Each node is configured to generate an output by carrying out a function on the values input to that node. The inputs to one or more nodes form the input of the neural network, the outputs of some nodes form the inputs to other nodes, and the outputs of one or more nodes form the output of the network. At some or all of the nodes of the network, the input to that node is weighted by a respective weight. A weight may define the connectivity between a node in a given layer and the nodes in the next layer of the neural network. A weight can take the form of a scalar or a probabilistic distribution. When the weights are defined by a distribution, as in a Bayesian model, the neural network can be fully probabilistic and captures the concept of uncertainty. The values of the connections between nodes may also be modelled as distributions. The distributions may be represented in the form of a set of samples or a set of parameters parameterizing the distribution (e.g. the mean $\mu$ and standard deviation a or variance $\sigma^2$).

The network learns by operating on data input at the input layer, and adjusting the weights applied by some or all of the nodes based on the input data. There are different learning approaches, but in general there is a forward propagation through the network from input layer to output layer, a calculation of an overall error, and a backward propagation of the error through the network from output layer to input layer. In the next cycle, each node takes into account the back propagated error and produces a revised set of weights. In this way, the network can be trained to perform its desired operation.

Training may employ a supervised approach based on a set of labelled training data. Other approaches are also possible, such as a reinforcement approach wherein the network each data point is not initially labelled. The learning algorithm begins by guessing the corresponding output for each point, and is then told whether it was correct, gradually tuning the weights with each such piece of feedback. Another example is an unsupervised approach where input data points are not labelled at all and the learning algorithm is instead left to infer its own structure in the experience data.

Other forms of machine learning model are also known, other than just neural networks, for example clustering algorithms, random decision forests, and support vector machines.

Some machine learning models can be designed to perform causal discovery using observational data or both observational and interventional data. That is, for a set of variables (e.g. $[x_1, x_2, x_3]$), the model when trained can estimate a likely causal graph describing the causal relationships between these variables. E.g. in the case of three variables a simple causal graph could be $x_1 \rightarrow x_2 \rightarrow x_3$, meaning that $x_1$ causes $x_2$ and $x_2$ causes $x_3$ (put another way, $x_3$ is an effect of $x_2$ and $x_2$ is an effect of $x_1$). Or as another example, $x_1 \rightarrow x_2 \leftarrow x_3$, means that $x_1$ and $x_3$ are both causes of $x_2$ ($x_2$ is an effect of $x_1$ and $x_3$). However, in the past such models were only used for causal discovery alone, not for treatment effect estimation for decision making. Another type of model aims to perform treatment effect estimation, which commonly assumes that the causal graph is already given by the user. Such methods did not previously work with unknown causal graphs.

"Deep End-to-End Causal Inference" [DECI] (Geffner et al, Microsoft Research, arxiv.org/pdf/2202.02195.pdf) appreciated that in many applications, users would benefit from the ability to perform treatment effect estimation for decision making with observational data only, without needing to know the causal graph. Accordingly, Geffner et al provided an integrated machine learning model that both models the causal relationships between variables and performs treatment effect estimation, by averaging over multiple possible causal graphs sampled from a distribution. This advantageously allows the method to exploit a model that has been trained for causal discovery in order to also estimate treatment effects. The method thus enables "end-to-end" causal inference.

SUMMARY

It is recognized herein that there is still further scope to improve on the DECI model developed by Geffner et al, or the like. Particularly, existing models do not model well time series data. The nature of cause-and-effect is such that causes in the past cause effects in the future. However, in a model based on only a static causal graph, there is nothing to stop the model learning or predicting that a cause in the future causes an effect in the past.

To address such issues or similar, the present disclosure discloses a model in which, instead of a static graph that contains only edges between variables at single snapshot in time, the model samples a temporal causal graph which contains causal edges between variables at different time steps.

According to one aspect disclosed herein, there is provided computer-implemented method comprising: A) selecting a selected variable from among variables of a feature vector; B) sampling a temporal causal graph from a temporal graph distribution, the temporal graph distribution specifying probabilities of directed causal edges between different ones of the variables of the feature vector at a present time step, and from one of the variables of the feature vector at a preceding time step to one of the variables of the feature vector at the present time step; and C) from among of the variables of the feature vector, identifying a present parent which is a cause of the selected variable in the present time step according to the temporal causal graph, and identifying a preceding parent which is a cause of the selected variable from the preceding time step according to the temporal causal graph. The method further comprises: D) inputting an input value of each of the identified present and preceding parent into a respective encoder, resulting in a respective embedding of each of the present and preceding parents; E) combining the embeddings of the present and preceding parents, resulting in a combined embedding; and F) inputting the combined embedding into a decoder associated with the selected variable, resulting in a reconstructed value of the selected variable.

Augmenting the model to include a temporal graph will advantageously lead to more accurate predictions as it will more accurately model the causal reality of the modelled scenario. Alternatively or additionally, the model may also be used to predict the best order in which to apply a series of two or more treatments, and/or the timing with which to apply one or more treatments; and/or to predict how long a treatment will take to take effect.

Another potential issue to take into account when handling time series data, is that if the modelled noise is static, then the model may not be optimally specified. For instance consider a scenario where a symptom of a modelled patient, or a sensor reading from a modelled device, remains relatively smooth during some periods, but becomes more erratic during other periods. It would be desirable to take this into account in the modelled noise.

Optionally to address this, the presently disclosed model may also include a history dependent noise term, which is generated based on values of variables from past time steps.

Hence in embodiments, the method may comprise generating a history dependent noise term based on embeddings of the preceding parents; and combining the history dependent noise term with the reconstructed value of the selected variable, resulting in a simulated value of the reconstructed variable.

Making the simulated noise dependent on history will lead to more optimal predictions, such as estimated treatment effects, as the model will again be more likely to be a more realistic representation of the ground truth.

Optionally, in some embodiments, the disclosed model may also take into account the presence of possible confounders, which have the potential to bias existing models. Consider two variables $x_1$ and $x_2$ and a model which is attempting to discover whether there is a causal edge between them, or to predict a treatment effect based on the modelled causation. A hidden confounder is a third variable which is not observed and which is a cause of both $x_1$ and $x_2$. This could lead to a false conclusion that $x_1$ is the cause of $x_2$ (or vice versa) when in fact there is no causal link (or a weaker causal link) and instead both $x_1$ and $x_2$ are an effect of a common causal variable $u_{12}$ (a confounder) which is not present in the input data (i.e. not one of the variables of the input feature vector). For instance in the healthcare field $x_1$ could measure the presence or absence of a certain condition (e.g. disease) in a subject, whilst $x_2$ could be a lifestyle factor such as an aspect of the subject's diet (e.g. salt or fat intake, etc.) or whether they are a smoker, and the confounder $u_{12}$ could be a measure of a socioeconomic circumstance of the patient (e.g. annual income). Ignoring the socioeconomic circumstance may give the false impression that the lifestyle factor $x_2$ causes the condition $x_1$, whereas in fact the ground truth is that both $x_1$ and $x_2$ are effects the socioeconomic circumstance. To address such possibilities, embodiments of the present disclosure provide a machine learning model which models the possibility of hidden confounders as latent variables model.

Accordingly, in embodiments B) may further comprise sampling a second causal graph from a second graph distribution, the second causal graph modelling presence of possible confounders, a confounder being an unobserved cause of both of two variables in the feature vector. In this case C) further comprises, from among of the variables of the feature vector, identifying a parent variable which is a cause of the selected variable according to the first causal graph, and which together with the selected variable forms a confounded pair having a respective confounder being a cause of both according to the second causal graph; and D) further comprises inputting the input value of the parent variable and an input value of the selected variable into an inference network, resulting in a latent value modelling the respective confounder of the confounded pair, and inputting the latent value into a second encoder, resulting in an embedding of the confounder of the confounded pair; and in E) the combining includes combining the embedding of the present and preceding parents with the embedding of the confounder of the confounded pair, thereby resulting in said combined embedding.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Nor is the claimed subject matter limited to implementations that solve any or all of the disadvantages noted herein.

BRIEF DESCRIPTION OF THE DRAWINGS

To assist understanding of embodiments of the present disclosure and to show how such embodiments may be put into effect, reference is made, by way of example only, to the accompanying drawings in which.

DETAILED DESCRIPTION OF EMBODIMENTS

Example System Overview

Figure 1:
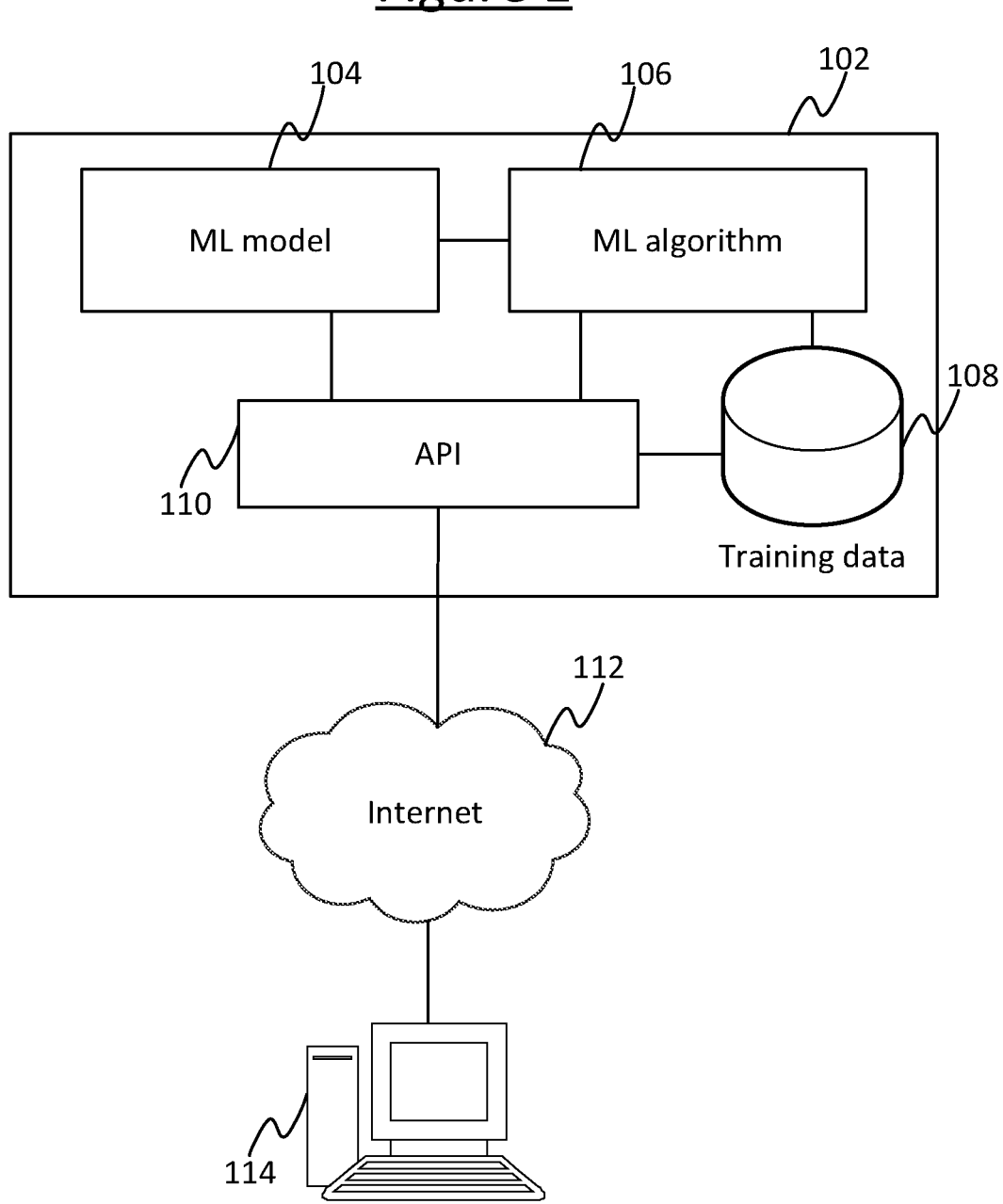
FIG. 1 is a schematic block diagram of a system in accordance with embodiments disclosed herein.

FIG. 1 illustrates an example system according to embodiments of the present disclosure. The system comprises a server system 102 of a first party, a network 112, and a client computer 114 of a second party. The server system 102 and client computer 114 are both operatively coupled to the network 112 so as to be able to communicate with one another via the network 112. The network 112 may take any suitable form and may comprise one or more constituent networks, e.g. a wide area network such as the Internet or a mobile cellular network, a local wired network such as an Ethernet network, or a local wireless network such as a Wi-Fi network, etc.

The server system 102 comprises processing apparatus comprising one or more processing units, and memory comprising one or more memory units. The, or each, processing unit may take any suitable form, e.g. a general purpose processor such as a CPU (central processing unit); or an accelerator processor or application specific processor such as a dedicated AI accelerator processor or a repurposed GPU (graphics processing unit), DSP (digital signal processor), or cryptoprocessor, etc. The, or each, memory unit may also take any suitable form, e.g. an EEPROM, SRAM, DRAM or solid state drive (SSD); a magnetic memory such as a magnetic disk or tape; or an optical medium such as an optical disk drive, quartz glass storage or magneto-optical memory; etc.

In the case of multiple processing units and/or memory units, these may be implemented in the same physical server unit, or different server units in the same rack or different racks, or in different racks in the same data centre or different data centres at different geographical sites. In the case of multiple server units, these may be networked together using any suitable networking technology such as a server fabric, an Ethernet network, or the Internet, etc. Distributed computing techniques are, in themselves, known in the art.

The memory of the server system 102 is arranged to store a machine learning (ML) model 104, a machine learning algorithm 106, training data 108, and an application programming interface (API) 110. The ML model 104, ML algorithm 106 and API 110 are arranged to run on the processing apparatus of the server system 102. The ML algorithm 106 is arranged so as, when run, to train the ML model 104 based on the training data 108. Once the model 104 is trained, the ML algorithm 106 may then estimate treatment effects based on the trained model. In some cases, after the ML model 104 been trained based on an initial portion of training data 108 and been made available for use in treatment effect estimation, training may also continue in an ongoing manner based on further training data 108, e.g. which may be obtained after the initial training.

The API 110, when run, allows the client computer 114 to submit a request for treatment effect estimation to the ML algorithm 106. The ML model 104 is a function of a plurality of variables. The request may specify a target variable to be examined, and may supply input values of one or more other variables (including intervened-on values and/or conditioned values). In response, the ML algorithm 106 may control the ML model 104 to generate samples of the target variable given the intervened-on and/or conditioned values of the one or more other variables. The API 110 returns the result of the requested causal query (the estimated treatment effect) to the client computer 114 via the network 112.

In embodiments, the API may also allow the client computer to submit some or all of the training data 108 for use in the training.

Causal Machine Learning Model

Figures 2, 3, 4:
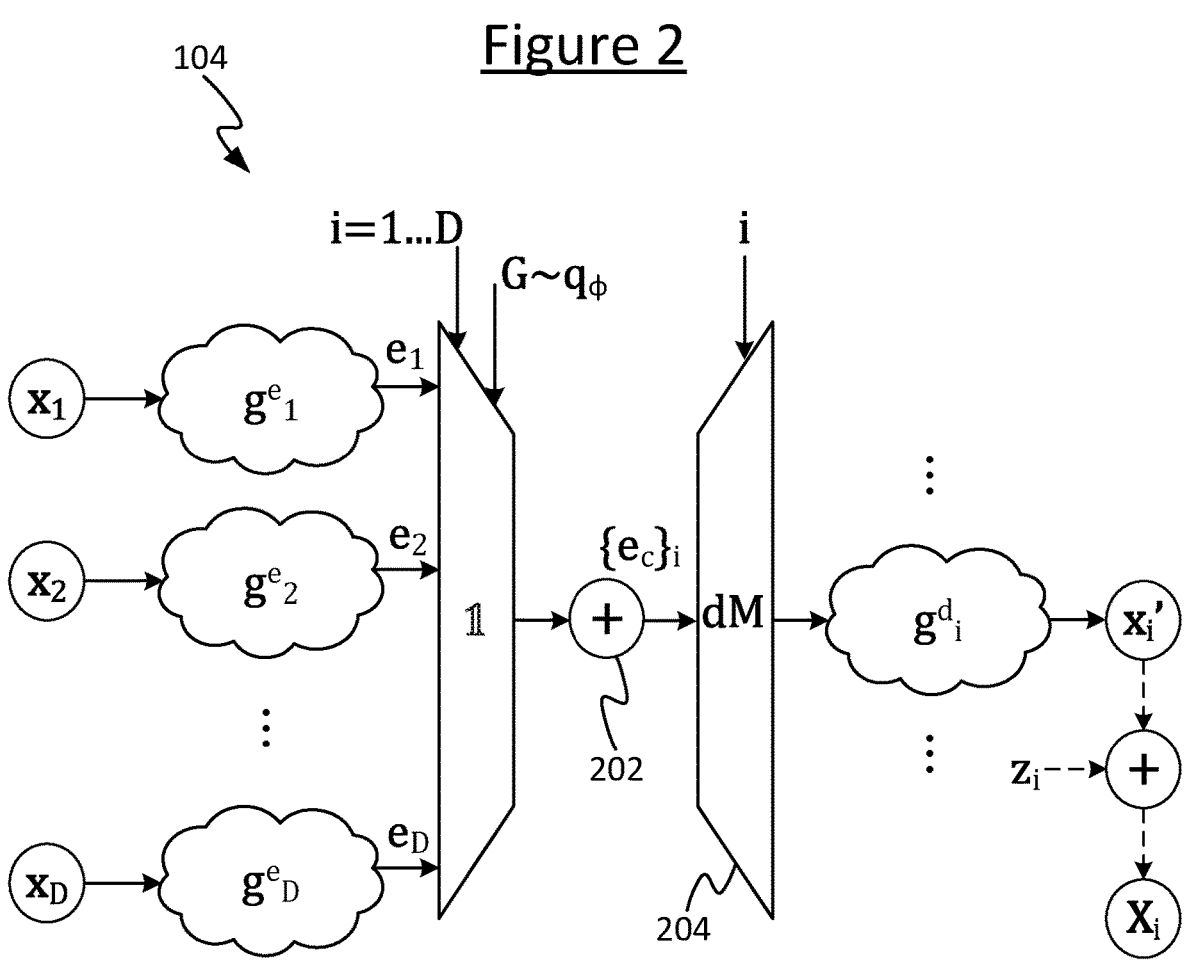
FIG. 2 is a schematic computation diagram illustrating an example of a machine learning model, FIG. 3 schematically illustrates an example of a causal graph.
FIG. 4 is schematic sketch of an example of a probabilistic distribution, FIG. 5 schematically illustrates another example of a causal graph.

FIG. 2 schematically illustrates an example implementation of a machine learning model 104 of a type as disclosed in "Deep End-to-End Causal Inference" (DECI) by Geffner et al. The ML model 104 comprises a respective encoder $$g_i^e$$

and a respective decoder $$g_i^d$$

for each of a plurality of variables $x_i$, where i is an index running from 1 to D where D>1. The set of variables $x_i \ldots x_D$ may be referred to as the input feature vector.

Each variable represents a different property of a subject being modelled. The subject may for example be a real-life entity, such as a human or other living being; or an object such as a mechanical, electrical or electronic device or system, e.g. industrial machinery, a vehicle, a communication network, or a computing device etc.; or a piece of software such as a game, operating system software, communications software, networking software, or control software for controlling a vehicle or an industrial processor or machine. Each property could be an inherent property of the being or object, or an environment of the being or object which may affect the being or object or be affected by the being or object.

For instance in a medical example, the variables represent different properties of a person or other living being (e.g. animal). One or more of the variables may represent a symptom experienced by the living being, e.g. whether the subject is exhibiting a certain condition such as a cough, sore throat, difficulty breathing, etc. (and perhaps a measure of degree of the condition), or a measured bodily quantity such as blood pressure, heart rate, vitamin D level, etc. One or more of the variables may represent environmental factors to which the subject is exposed, or behavioural factors of the subject, such as whether the subject lives in an area of high pollution (and perhaps a measure of the pollution level), or whether the subject is a smoker (and perhaps how many per day), etc. And/or, one or more of the variables may represent inherent properties of the subject such as a genetic factor.

In the example of a device, system or software, one or more of the variables may represent an output state of the device, system or software. One or more of the variables may represent an external factor to which the device, system or software is subjected, e.g. humidity, vibration, cosmic radiation, and/or a state of one or more input signals. For instance the variables may comprise a control signal, and/or an input image or other sensor data captured from the environment. Alternatively or additionally, one or more of the variables may represent an internal state of the device, system or software, e.g. an error signal, resource usage, etc.

One, more or all of the variables may be observed or observable. In some cases, one or more of the variables may be unobserved or unobservable.

Each respective encoder $$g_i^e$$

is arranged to receive an input value of its respective variable $x_i$, and to generate a respective embedding $e_i$ (i.e. a latent representation) based on the respective input value. As will be familiar to a person skilled in the art, an embedding, or latent representation or value, is in itself a known concept. It represents in the information in the respective input variable an abstracted form, typically in a compressed form, which is learned by the respective encoder during training. The embedding may be a scalar value, or may be a vector of dimension 'embedding_dim' which is greater than 1.

Note that a "value" as referred to herein could be a vector value or a scalar value. For example if one of the variables is an image (e.g. a scan of the subject), then the "value" of this vector variable is the array pixel values for the image.

The different variables $x_i$ may have a certain causal relationship between them, which may be expressed as a causal graph. A causal graph may be described as comprising a plurality of nodes and edges (note that these are not the same thing as the nodes and edges mentioned earlier in the context of a neural network). Each node represents a respective one of the variables $x_i$ in question. The edges are directional and represent causation. I.e. an edge from $x_{i=k}$ to $x_{i=l}$ represents that $x_k$ causes $x_l$ ($x_l$ is an effect of $x_k$). A simple example involving three variables is shown in FIG. 3. In this example $x_2$ causes $x_1$, and $x_1$ causes $x_3$. For example $x_3$ may represent having a respiratory virus, $x_1$ may represent a lung condition and $x_2$ may represent a genetic predisposition.

Of course other possible graphs are possible, including those with more variables and other causal relationships.

A given graph G may be expressed as a matrix, with two binary elements for each possible pair of variables $x_{i=k}$, $x_{i=l}$; one binary element to represent whether an edge exists between the two variables, and one to represent the direction of the edge if it exists (e.g. 0=no edge from k to l, 1=edge from k to l, or vice versa). For example for three variables this could be written as:

$$G = \begin{pmatrix} Exists1, 2 & Dir1, 2 \\ Exists1, 3 & Dir1, 3 \\ Exists2, 3 & Dir2, 3 \end{pmatrix}$$

Other equivalent representations are possible. E.g. an alternative representation of the probabilities of existence and direction of edges in a graph would be:

$$G = \begin{pmatrix} Exists1 \to 2 & Exists1 \to 3 & Exists2 \to 3 \\ Exists2 \to 1 & Exists3 \to 1 & Exists3 \to 1 \end{pmatrix}$$

For any given situation, the actual causal graph may not be known. A distribution $q_\phi$ of possible graphs may be expressed in a similar format to G, but with each element comprising a parameter $\phi$ (phi, also drawn $\varphi$) representing a probability instead of a binary value.

$$q_\varphi = \begin{pmatrix} \varphi\_exists1, 2 & \varphi\_dir1, 2 \\ \varphi\_exists1, 3 & \varphi\_dir1, 3 \\ \varphi\_exists2, 3 & \varphi\_dir2, 3 \end{pmatrix}$$

(Or an equivalent representation.) In other words the parameter $\phi\_exists1,2$ represents the probability that an edge between $x_1$ and $x_2$ exists; $\phi\_dir1,2$ represents the probability that the direction of the possible edge between $x_1$ and $x_2$ is directed from $x_1$ to $x_2$ (or vice versa); parameter $\phi\_exists1,2$ represents the probability that an edge between $x_1$ and $x_3$ exists; etc.

Returning to FIG. 2, the ML model 104 further comprises a selector 1, a combiner 202 and a demultiplexer 204. It will be appreciated that these are schematic representations of functional blocks implemented in software. The selector 1 is operable to sample a causal graph G from the distribution. This means selecting a particular graph G (with binary elements) whereby the existence and direction of the edges are determined pseudorandomly according to the corresponding probabilities in the distribution $q_\phi$.

Preferably the possible graphs are constrained to being directed acyclic graphs (DAGs), for the sake of practicality and simplicity of modelling.

The selector 1 also receives a value of the index i for a selected target variable $x_i$. For the currently selected variable $x_i$ (node of index i in the graph), the selector 1 selects the respective embeddings $e_{Pa(i)}$ generated by the respective encoders $$g_{Pa(i)}^e$$

of the parents Pa(i) of the node i (variable $x_i$) in the currently sampled graph G, and inputs these into the combiner 202.

The combiner 202 combines the selected embeddings $e_{Pa(i)}$ into a combined embedding $e_c$. In embodiments the combination is a sum. In general a sum could be a positive or negative sum (a subtraction would be a sum with negative weights). The combined (summed) representation thus has the same dimension as a single embedding, e.g. 'embedding_dim'. In alternative implementations however it is not excluded that another form of combination could be used, such as a concatenation.

The demultiplexer 204 also receives the index i of the currently selected variable $x_i$, and supplies the combined embedding $e_c$ into the input of the decoder $$g_i^d$$

associated with the currently selected variable $x_i$. This generates a value of a respective noiseless reconstructed version $x_i'$ of the respective variable $x_i$ based on the combined embedding $e_c$.

The encoders $$g_{i=1 \ldots D}^e$$

and decoders $$g_{i=1 \ldots D}^d$$

are constituent machine learning models comprised by the overall ML model 104. They are each parameterized by respective sets of parameters $\theta$ which are tuned during learning. In embodiments, each of the encoders $$g_{i=1 \ldots D}^e$$

and decoders $$g_{i=1 \ldots D}^d$$

is a respective neural network (in which case their parameters may be referred to as weights). However it is not excluded that some or all of them could instead be implemented with another form of constituent machine learning model.

Training

Figure 7:
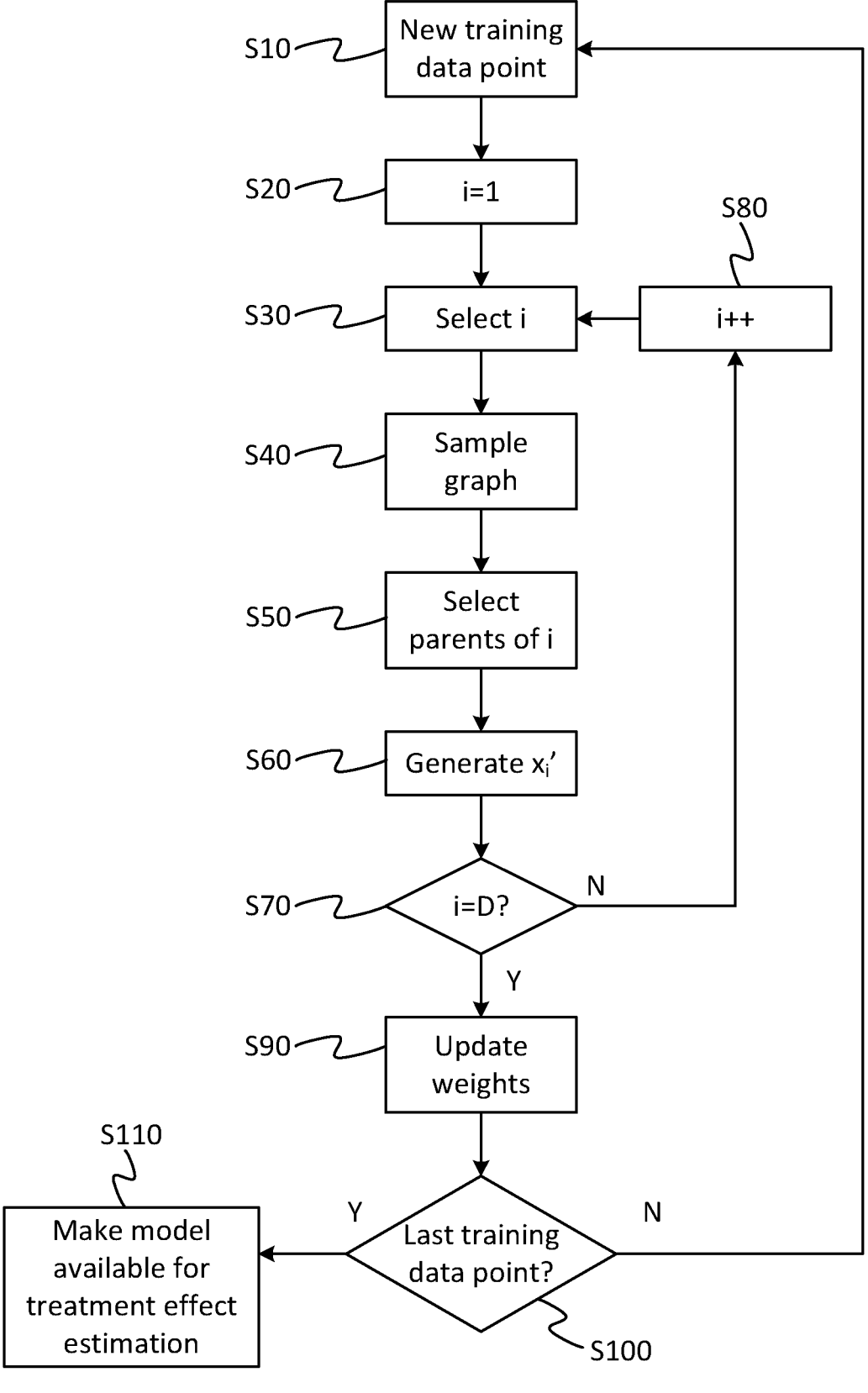
FIG. 7 is a schematic flowchart of a method of training a model in accordance with the present disclosure.

FIG. 7 schematically represents a method of training the DECI type model 104 based on a training data 108. The training data 108 comprises a plurality of training data points. Each data point $[x_1 \ldots x_D]$ comprises a set of input values, one respective value for each of the variables $x_i$.

The method processes each of the training data points, at least in an initial portion of the training data 108. At step S10 the method takes a new data point from memory, and at step S20 the index i is set to a first value (e.g. i=1) to specify a first target variable $x_i$ from among the set of variables in the data point. At step S30, this causes the selector 1 to select the target variable $x_i$ with the currently set value of the index i as the variable to be processed. At step S40 the selector 1 samples a random graph G from the distribution $q_\phi$. At step S50, the selector 1 selects the parents Pa(i) of the target variable $x_i$ (node i in the graph) and supplies the respective embeddings $e_{Pa(i)}$ from the encoders $$g_{Pa(i)}^e$$

of the selected parents into the combiner 202. At step S60, the combiner 202 combines (e.g. sums) the embeddings of the selected parents Pa(i) into the combined embedding $e_c$, and the demultiplexer 204 selects to supply the combined embedding $e_c$ into the decoder $$g_i^d$$

of the target variable $x_i$. The respective decoder $$g_i^d$$

is thus caused to generate a noiseless reconstruction $x_i'$ of the selected target variable $x_i$.

This could equally be expressed as:

$$x_i' = g_i^d\left(\sum_{j \in Pa(i)} g_j^e(x_j)\right)$$

where $\Sigma_{j \in Pa(i)}$ is another way of writing the operations of the selector 1 and combiner 202. Preferably, G is a DAG (directed and acyclic) so that it is valid to generate the value of any node in this way. The difference $x_i - x_i'$ may be referred to as the residual.

The process is repeated for each variable $x_i$ in the set of variables, i.e. for i=1 . . . D, thus creating a full reconstructed set of values $[x_1' \ldots x_D']$ for the data point in question. This is represented schematically by steps S70 and S80 in FIG. 7, looping back to S30. However note that this the "loop" may be a somewhat schematic representation. In practice some or all of the different variables $x_i$ for a given data point could be processed in parallel.

At step S90 the ML algorithm 106 applies a training function which updates the parameters (e.g. weights) $\theta$ of the encoders g $$g_{i=1 \ldots D}^e$$

and decoders $$g_{i=1 \ldots D}^d.$$

Simultaneously it also updates the parameters $\phi$ of the distribution $q_\phi$ of possible graphs. The training function attempts to update the parameters $\theta$, $\phi$ in such a way as to reduce a measure of overall difference between the set of input values of the set of input variables $[x_1 \ldots x_D]$ and the reconstructed version of the set variables $[x_1' \ldots x_D']$. For example in embodiments the training function is an evidence lower bound (ELBO) function. Training techniques of this kind are, in themselves, known in the art, e.g. based on stochastic back propagation and gradient descent.

During the training phase, $x_i$ is an observed data value that is attempted to be reconstructed. The residual $x_i - x_i'$ between the reconstruction and the observation may be used to compute the ELBO objective.

In embodiments, the model 104 may be a probabilistic model that it assigns a joint probability (likelihood) $p(X_1, \ldots, X_D)$ to all the variables $X_1, \ldots, X_D$; where $X_i$ represents the noiseless reconstruction $x_i$ combined with a random noise term $z_i$, e.g. additively $(X_i = x_i' + z_i)$, and $z_i$ may be sampled from a random distribution, $z_i \sim p(z_i)$. In such embodiments, then in order to train the model 104, one first collects a real-world data point with D-dimensional features $(x_1, x_2, \ldots, x_D)$, and then maximizes the likelihood of it being generated by the model. That is to say, the training operates to try to maximize $p(X_1=x_1, X_2=x_2, \ldots, X_D=x_D)$. This is done by adjusting the parameters (e.g. weights) $\theta$ of the model 104. The ELBO mentioned previously is an example of a numerical approximation to the quantity $p(X_1=x_1, X_2=x_2, \ldots, X_D=x_D)$. ELBO is typically much easier to compute than $p(X_1=x_1, X_2=x_2, \ldots, X_D=x_D)$.

The above-described process is repeated for each of the data points in the training data 108 (or at least an initial portion of the training data). This is represented schematically in FIG. 7 by step S100 and the loop back to S10. Though again, this form of illustration may be somewhat schematized and in some implementations, batches of data points could be reconstructed in parallel, and the model parameters updated based on the batches.

At the beginning of the overall training method the graph distribution $q_\phi$ may start with some predetermined set of probabilities, e.g. all elements 0.5 for the existence and direction of each possible edge, or using some prior domain knowledge to inform which edges are possible or impossible, or more or less likely. Then, as the model is trained with more and more data points, the probabilities (i.e. the parameters $\phi$ of $q_\phi$) are gradually learned in parallel with the parameters $\theta$ (e.g. weights) of the encoders and decoders $$g^e_{i=1,\ldots,D}, g^d_{i=1,\ldots,D}.$$

Treatment Effect Estimation

Once the model 104 has been trained sufficiently based on all the data points in the training data 108 (or at least an initial portion of the initial training data), then at step S110 the trained ML model 104 is made available to be used for treatment effect estimation (i.e., answering causal queries). In embodiments, this may comprise making the model 104 available to via the API 110 to estimate treatment effects/answer causal queries requested by the client computer 114.

Figure 8:
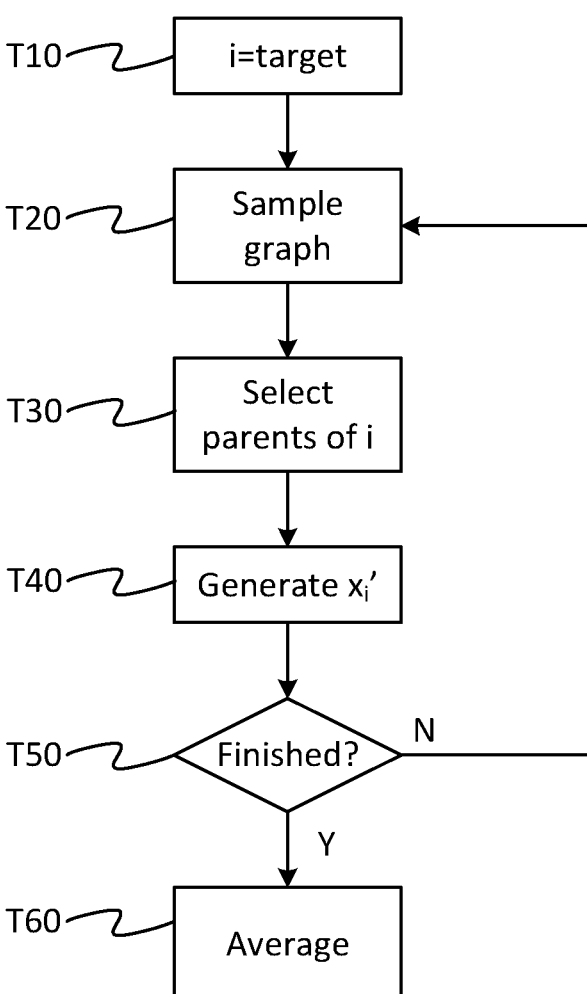
FIG. 8 is a schematic flowchart of a method of making treatment effect estimations using a trained model in accordance with embodiments disclosed herein, FIG. 9 schematically illustrates a causal graph (or part thereof) including a possible confounder between a pair of variables.

A method of using the ML model 104 to estimate a treatment effect is shown schematically in FIG. 8.

At step T10 the index i is set to that of a target variable $x_i$ whose treatment effect is to be estimated. In addition, the input values of one or more "intervened-on" variables are also set to their known values. The intervened-on variables are variables whose values are set to some specified value, to represent that the property that they represent has been controlled (the treatment, i.e. an intervention on the modelled property). An "intervened-on" variable could also be referred to as a treated variable or controlled variable. For example, in the medical application, the intervened-on variable(s) may represent one or more interventions performed on the subject, and the target variable may represent a possible symptom or condition of the subject (e.g. the presence of a certain disease). Or in the case where the subject is a device or software, the intervened-on variable(s) may represent one or more states that are set to defined values, and the target variable may represent a condition or state of the device or software that is being diagnosed.

At step T20, the selector 1 samples a graph G pseudo-randomly from the distribution $q_\phi$ according to the probabilities $\phi$. In other words the chance of there existing an edge in given direction between each pair of nodes i=k, i=l in the sampled graph G is determined by the pair of parameters $\phi\_exists(k,l)$; $\phi\_dir(k, l)$. Although optionally, some of the learned probabilities could be overridden to predetermined values based on prior knowledge (e.g. in some scenarios a given causality could be ruled out—probability set to zero—or may be known to be unlikely, either based on a priori or empirical knowledge).

At step T30 the selector 1 selects the parents Pa(i) of the target variable $x_i$ in the sampled graph G, and supplies the respective embeddings $e_{Pa(i)}$ from the encoders $$g^e_{Pa(i)}$$

of the selected parents into the combiner 202 to be combined (e.g. summed) into the combined embedding $e_c$. The demultiplexer 204 selects to pass the combined embedding $e_c$ into the decoder $$g^d_i$$

of the target variable $x_i$, thus causing it to generate a noiseless reconstruction of $$x'_i.$$

Thus the selection 1 selects the parents of node i in the graph G, so it depends on both i and G. The index is set to a particular target node i that one is trying to estimate (as well as selecting a graph G from $q_\phi$), and the model 104 outputs a noiseless reconstruction of $x_i$, denoted by $x_i'$. During training, such reconstruction was formed of each node given the actual data for its parent nodes.

Now at test time, the model 104 is used in a slightly different way for treatment effect estimation. Here, the target variable $x_i$ which is now treated as unknown, and the goal is to generate simulated values of the target variable, given other interventional variables. In some embodiments the simulated value could just be taken as the noiseless reconstructed value $x_i$. However for some purposes, the noiseless reconstruction $x_i'$ of the target variable $x_i$ may not be considered preferable, and instead the full interventional distribution may be taken into account. This can be characterized by the following sources of uncertainties: 1), different realizations of the graph G that could happen to have been selected during sampling (even an unlikely one), which can be modelled by simulating different graphs from $q_\phi$; and 2), the randomness of the residual noise random variables $z_i$. The latter can be taken into account by the following simulation equation:

$$X_i = g^d_i\left(\sum_{j\in Pa(i)} g^e_j(x_j)\right) + z_i, \; z_i \sim p(z_i).$$

In other words, during the treatment effect estimation phase, $X_i$ is a simulated value that is obtained through random sampling of $z_i$, wherein $X_i=x_i'+z_i$ (except for $x_{i=T}$, the intervened-on variable). More generally in other possible implementations, the noise $z_i$ could be combined with the noiseless reconstruction $x_i'$ in other ways in order to obtain $Xi$, not necessarily additively.

In the following description, reference may be made to $X_i$ as the simulated value of target variable $x_i$. However generally the simulated value could simply be the noiseless reconstructed value $x_i'$, or $X_i$ (which takes into account noise, e.g. $X_i = x_i' + z_i$), or a value which is simulated based on the reconstructed value $x_i'$ in any other way.

By whatever means the simulated value is determined, according to the present disclosure, an average is taken over multiple sampled graphs. In embodiments, an average is taken over multiple sampled graphs and residual noise variables $z_i$. In other words, for a given target variable $x_i$ to be estimated, multiple values of variable $X_i$ are simulated based on different respective sampled graphs G, each time sampled randomly from both $q_\phi$ and $z_i$ This is represented schematically in FIG. 8 by the loop from step T50 back to T20, to represent that multiple simulated values of $x_i$ are determined (for a given target variable $x_i$), each determined based on a different randomly sampled graph G (each time sampled from the distribution $q_\phi$) and optionally noises $z_i$. Again the illustration as a loop may be somewhat schematized, and in embodiments some or all of the different simulated values for a given target variable $x_i$, based on the different sampled graphs and sampled residual noises z, may in fact be computed in parallel.

In embodiments the average could be taken as a simple mean, median or mode of the different values of the simulated values $x_i'$ or $X_i'$ of the variable $x_i$ (as simulated with the different sampled graphs and optionally residual noises). In embodiments, such averaging is based on estimating an expectation of the probabilistic distribution of the simulated values.

FIG. 4 schematically illustrates the idea of a probabilistic distribution $p(x_i)$. The horizontal axis represents the value of the target variable being simulated, $x_i$, and the vertical axis represents the probability that the variable takes that value. If the distribution is modelled as having a predetermined form, it may be described by one or more parameters, e.g. a mean $\mu$ and standard deviation a or variance $\sigma^2$ in the case of a Gaussian. Other more complex distributions are also possible, which may be parameterized by more than two parameters, e.g. a spline function. As a convenient shorthand the probabilistic distribution may be referred to as a function the target variable of $x_i$, i.e. $p(xi)$, in the sense that it models the distribution of the target variable $x_i$, but in fact it will be appreciated that the distribution is in fact determined based on the corresponding simulated values $x_i'$ or $X_i$.

Based on the trained model 104, it is possible using statistical methods to estimate an expectation $E[p(x_Y)|do(x_T = val1)]$ of the probabilistic distribution p of a particular target variable $x_{i=Y}$ given the intervened value val1 of another, treatment/intervention variable $x_{i=T}$. In embodiments, the target variable $x_Y$ may model an outcome of a treatment modelled by $x_T$. Note that "treatment" as used most broadly herein does not necessarily limit to a medical treatment or a treatment of a living being, though those are certainly possible use cases. In other examples, the treatment may comprise applying a signal, repair, debugging action or upgrade to an electronic, electrical or mechanical device or system, or software, where the effect may be some state of the device, system or software which is to be improved by the system. In embodiments, the actual real-world treatment may be applied in dependence on the estimation (e.g. expectation) of the effect of the modelled treatment, for example on condition that the treatment estimation (e.g. expectation) is above or below a specified threshold or within a specified range.

One suitable measure of expectation may be referred to as the average treatment effect (ATE). This may be expressed as:

$$E[p(x_Y)|do(x_T = val1)] - E[p(x_{i=Y})|(do(x_T = val2)]$$

or $$E[p(x_Y)|do(x_T = val1)] - E[p(x_{i=Y})]$$

which could also be expressed $E[p(x_Y)|do(x_T=val1)]-E[p(x_{i=Y})|do(x_T=mean(x_T))]$, where val1 is some treatment, val2 is some other treatment, and "do" represents applying the treatment. In other words, the ATE is the difference between: a) the expectation of the distribution of the effect $x_Y$ given the value val1 of a treatment $x_T$ and b) the expectation of the distribution of the effect $x_Y$ given the value val2 of a treatment $x_T$, or the difference between a) the expectation of the distribution of the effect $x_Y$ given the value val1 of a treatment $x_T$ and b) the expectation of the distribution of the effect $x_Y$ without applying a value of the treatment $x_T$. Note that in variants the equality $x_T=val1$ or $x_T=val2$ could be replaced with another form of expression such as a "greater than", "less than" or range type expression.

An estimation of $E[p(x_Y)|do(x_T=treatment)$ may be determined based on the modelled distributions of noise, together with the learned graph and arrow functions. This may be done using the noise distribution at node $x_Y$, and using noise samples from other upstream variables, plus knowledge of the graph and its behaviour under the intervention $do(x_T=treatment)$, in order to thus make the ATE estimation calculation. The expectation $E[p(x_Y)|do(x_T=val)]$ of a target variable $x_Y$ given a treatment $x_T=val$ may be computed as:

$$E\left[g_Y^d\left(\sum\nolimits_{i \in Pa(Y)} e_i\right) + z_Y\right]$$

where $z_Y$ is a noise term. E is an average over everything that is random in the equation. Consider for example a simple graph:

$$x_1 \rightarrow x_2 \leftarrow x_3$$

where $x_1$ is the treatment $x_T$, and $x_2$ is the target variable $x_Y$. In the computation of E, $x_1$ is set to its known value. E may then be written:

$$E\left[g_Y^d(g_1^e(x_1 = val) + g_3^e(x_3)) + z_Y\right]$$

To compute E, one example method is simply to take the mean of the different sampled values $x_Y'$ or $X_Y$ of the target variable $x_Y$, based on the different sampled graphs, optionally also including some random noise (e.g. additive noise) in each sample. Another option is to fit the sampled values of $x_Y$ to a predetermined form of distribution, such shown as in FIG. 4, e.g. a Gaussian, normal or spline function (again optionally also including random noise). The average may then be determined as the average of the fitted distribution.

Note that during the determination of the multiple instances of $x_i'$ it is possible, especially for some distributions, that the same graph G ends up being sampled multiple times, or even every time. However the graph is still being freshly sampled each time and even if the sampled graphs turn out to be the same, they may still be described as different instances of the sampled graph, in the sense that they are individually sampled anew each time. In the case where the multiple graphs happen to be the same, then the averaging only averages the noise z.

In some cases, if the treated (i.e. controlled) variable has one or more parents, the graph G may be mutilated: $G \rightarrow G_{do(xT=val)}$. E.g. consider the graph:

$$x_4 \rightarrow x_1 \rightarrow x_2 \leftarrow x_3$$

where again $x_1$ is the treatment $x_T$, and $x_2$ is the target variable $x_Y$. In the computation of E, $x_1$ is set to its known value. Therefore $x_4$ has no effect on the outcome of $x_2$. So in the determination of the expectation, the graph is mutilated to remove the node $x_4$ and the edge from $x_4 \rightarrow x_1$. In other words, fixing the value of the known (controlled) variable $x_1$ means that any effect of the edge from the parent of the known variable $x_1$.

Another type of average which may be determined according to embodiments disclosed herein may be referred to as the conditional ATE (CATE). This is the difference between: a) the expectation of the target variable $x_Y$ given the treatment $x_T$=val1 conditional on an observation $\gamma$ of at least one other of the variables $x_C$ in the set, and b) the expectation of the target variable $x_Y$ without the treatment (either with a different treatment val2 or no treatment) but still conditional on the same observation of $x_C$. That is, or:

$$E[p(x_Y)|do(x_T = val1), x_C = Y] - E[p(x_Y)|do(x_T = val2), x_C = Y]$$

or:

$$E[p(x_Y)|do(x_T = val1), x_C = Y] - E[p(x_Y)|, x_C = Y]$$

which could also be expressed $E[p(x_Y)|do(x_T=val1), x_C=\gamma] - E[p(x_{i=Y})|do(x_T=mean(x_T)) x_C=\gamma]$.

Note that in variants the equality $x_T$=val1, $x_T$=val2, or $x_C=\gamma$ could be replaced with another form of expression such as a "greater than", "less than" or range type expression.

Figures 5, 6:
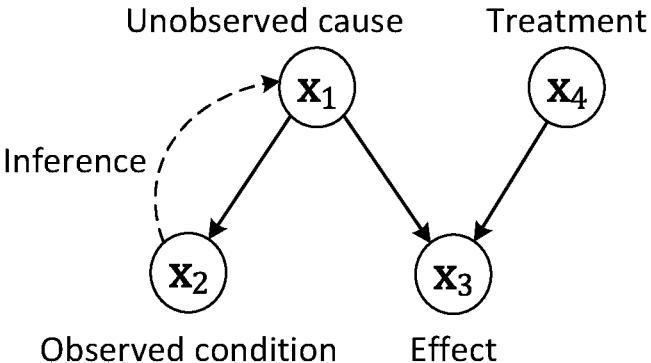
FIG. 6 is a schematic computation diagram illustrating a further machine learning model.

FIG. 5 illustrates by way of example why estimating the conditional treatment effect is not necessarily straightforward. In this example $x_3$ is the target xv whose treatment effect will be estimated and $x_4$ is the treatment $x_T$, where the treatment is the cause of the target effect. In addition, there is another, unobserved cause $x_1$ of the target effect, and another observable effect $x_2$ of the unobserved cause $x_1$. The variable $x_2$ is to be the observed condition $x_C$. For instance, in a medical example the target effect $x_3$ could be some condition or symptom of the subject (e.g. a respiratory problem), the treatment $x_4$ could be a possible medical intervention (e.g. taking some drug or vitamin), the unobserved cause $x_1$ may be a genetic factor, and the other observable cause $x_2$ may be some observable physical quality of the subject's body (e.g. body mass index). In general the unobserved cause could be unobservable, or merely unobserved.

The observable condition $x_2$ contains information about the unobserved cause $x_1$, which in turn can reveal information about the desired effect $x_3$ (=$x_Y$). For example if it is known that an athlete is in the Olympics and that they are a footballer, this reduces the probability that they are also a rower. In fact for any two variables that are effects of a common cause and whose intersection is not 100%, knowing something about one gives information about the other. E.g. if it is known that a subject has lung cancer and that they were exposed to a carcinogenic chemical other than tobacco, this reduces the probability that they were are smoker.

However the causal direction is from $x_1 \rightarrow x_2$, and the model 104 of FIG. 2 is only configured to learn effects of causes in the direction from cause to effect—it is not configured to learn inferences of effect from cause. I.e. it is not configured to "go against the arrows" in the figure (the directional causal edges).

To address this, as illustrated in FIG. 6, in embodiments the ML model 104 may be adapted to include at least one inference network h disposed between at least one observable condition $x_c$ ($x_2$ in the example) and at least one unobservable potential cause ($x_1$ in the example) of the condition $x_c$. As illustrated in FIG. 6, in some such embodiments, the inference network h (or individual such networks) may be disposed between the unobserved cause and multiple potential effects (up to all the other variables). This will allow the model to learn which variable(s) may be an effect of the unobserved cause, if relationship is not prior knowledge.

The inference network(s) h may be trained at the training stage simultaneously along with the encoders $g^e$ and decoders $g^d$ and the parameters of the graph distribution $q_\phi$, or alternatively after the rest of the model (see below). In embodiments the inference network h may comprise a neural network, in which case training the inference network comprises tuning the weights of the inference network. Alternatively the use of other forms of machine learning is not excluded for the inference network.

The inclusion of the inference model makes it possible to estimate a conditional expectation such as $E[x_Y|do(x_T=val1), x_C=\gamma]$.

To estimate the conditional expectation, then initially during the estimation of the target variable $x_Y$, the conditional variable $x_c$ is not fixed. In other words, the method proceeds as described above with respect to ATE, to obtain multiple different samples of $x_Y$ based on multiple respective sampled graphs. At the same time, respective simulated samples $x_c$ of the conditional variable are also obtained in the same way based on the respective sampled graphs. This gives a two dimensional set of samples ($x_Y$, $x_c$), which could be described as a plot or "scatter plot". Then a predetermined form of function is fitted to the 2D set of samples ($x_Y$, $x_c$), such as a straight line, a curve, or a probabilistic distribution. After that, xc is set to its observed value in the fitted function, and a corresponding value of $x_Y$ is read out from the fitted function. This is taken as the conditional expectation of $x_Y$ given $x_c$.

At least two alternative variants to computing CATE may be employed, depending on implementation.

Variant I: estimate CATE using the same approach as used to estimate ATE, but performing a re-weighing of the terms inside of the expectations such that the condition (that gives CATE its name) is satisfied. This type of approach is known as an importance sampling technique. The weights of the different samples used to compute the expectation are provided by an inference network, which is trained together with the rest of the ML model 104.

Variant II: after the model 104 of FIG. 2 has been trained and a specific CATE query is received (e.g. via the API 110), the inference network h is trained to estimate the effect variable from the conditioning variable. To train this model, data simulated from the trained model of FIG. 2 is used, while applying some treatment specified in the query. Then the conditional average treatment effect is estimated by inputting the relevant value of the conditioning variable into the inference network h. It returns a distribution over effects from which the expected effect can be computed.

The main difference between the two approaches is that the first solely uses components learnt from the observed data during model training, while the second requires learning a new network after the model 104 has been trained. The reasoning for proposing both methods is that there are specifics settings where one or the other are more computationally efficient.

Note that the disclosed methods are not limited to the controlled (i.e. treated) variable $x_T$ being a direct parent of the target variable xv (i.e. the variable whose treatment effect being estimated). The treated variable or the effect variable can be any arbitrary variable in the set $x_{i=1 \ldots D}$, e.g. a grandparent of the target variable $x_Y$.

In embodiments, the simulation of the target variable takes into account a potential effect of all causal variables across the sampled graph. An example implementation of this is as follows. This may be used in conjunction with any of the ways of averaging discussed above, or others.

The method of estimating the target variable $x_Y$ (e.g. the treatment effect) may comprise an inner and an outer loop. In the inner loop, the method loops through i=1 . . . D, so as to generate the simulated value $X_i$ (or just $x_i'$) of each of the input variables $x_i$ (even those that are not the target variable), except skipping over the one or more controlled (treated or known) variables $x_T$ which are set to their known, fixed values (any edges into those nodes have been "mutilated" away, i.e. removed from the sampled graph). Then, proceeding to the next round (iteration) of the outer loop, the simulated values $X_i$ of the non-controlled variables are fed back to the respective inputs of the model 104. In other words (other than for the one or more controlled variables $x_T$), the simulated values $X_i$ from the previous round or cycle (iteration) of the outer loop become the input values $x_i$ of the current iteration of the outer loop to generate an updated set of values for the simulated variables $x_i$. This may be repeated one or more further times, and the simulated values will start to converge (i.e. the difference between the input layer and output layer of the model 104 will get smaller each time). If noise is included the noise is frozen throughout a given inner loop, then re-sampled each outer loop. The total number of iterations of the outer loop may be predetermined, or the outer loop may be iterated until some convergence criterion is met. In embodiments the outer loop is iterated at least D-1 times, which guarantees convergence without needing to evaluate a convergence criterion.

This method advantageously allows causal effects to propagate throughout the graph. For example if $x_1$ causes $x_2$ and $x_2$ causes $x_3$, and an intervention is performed on x1 then the outer loop will be run at least two times to propagate the effect through to x3.

However the method of using an inner and outer loop is not essential. An alternative would be to perform a topological sort of the nodes and propagate effects through in a hierarchical fashion starting from the greatest grandparents or "source nodes" (those which are only causes and not effects). Or as another alternative, though less preferred, it is not necessary to propagate effects through multiple generations and instead only the effects of immediate parents of the target variable may be taken into account.

Optional Extension to Include Latent Confounders

The following describes an optional extension to the model to accommodate the possible presence of "confounders".

Figure 9:
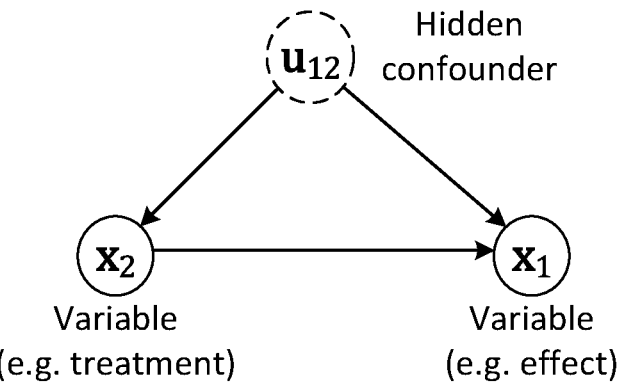

FIG. 9 schematically illustrates the issue of the presence of possible "hidden confounders", which may also be referred to just as confounders. A confounder is a variable that is both A) unobserved (i.e. hidden, so not part of the input feature vector); and B) a cause of at least two variables that are among the variables of the input feature vector $[x_1 \ldots x_D]$. These two variables may be referred to herein as the "confounded" variables or a "confounded pair" of the respective confounder. In the example of FIG. 9 the confounded variables are labelled $x_1$ and $x_2$ and the confounder between them is labelled $u_{12}$. The confounder could be unobservable or merely unobserved. Of course the causal graph may be more complex than shown in FIG. 9, and confounders may exist between more than one pair of variables of the input feature vector.

An issue recognized herein is that existing machine learning models do not take into account the presence of possible confounders, which may lead to an erroneous bias in the training of such models or predictions made by such models. Consider for example a scenario where $x_1$ is a variable measuring the presence or absence of a certain condition (e.g. disease) in a subject (e.g. patient), and $x_2$ is a variable measuring a property of the subject which may or may not affect the possible presence of the condition. For instance $x_2$ could measure a lifestyle factor such as an aspect of the subject's diet (e.g. salt or fat intake, etc.), whether they are a smoker, a dosage of a certain medication they are taking, or an environmental factor such as living in an area of high pollution or near an electricity pylon. Say then that the model is being used to try to learn whether there is a causal link between $x_1$ and $x_2$, or to predict what would be the effect on $x_1$ of treating $x_2$. However there may be an unobserved common cause of the two variables, i.e. a confounder. For instance, the confounder $u_{12}$ could represent a factor in the socioeconomic circumstances of the patient (e.g. annual income, education or family circumstances). Ignoring the confounder (e.g. socioeconomic circumstance) may give the false impression that the lifestyle factor $x_2$ causes the condition $x_1$, whereas in fact the ground truth is that both $x_1$ and $x_2$ are effects of the socioeconomic circumstance, in which case $x_2$ may not actually be a cause of $x_1$ or may only be a weaker cause than it would otherwise appear.

The presently disclosed extension—which in embodiments may be applied as an extension to the previous work by Geffner et al summarised in the Background section—introduces the modelling of possible hidden confounders into a causal machine learning model by introducing a second causal graph sampled from a second graph distribution.

Figure 10:
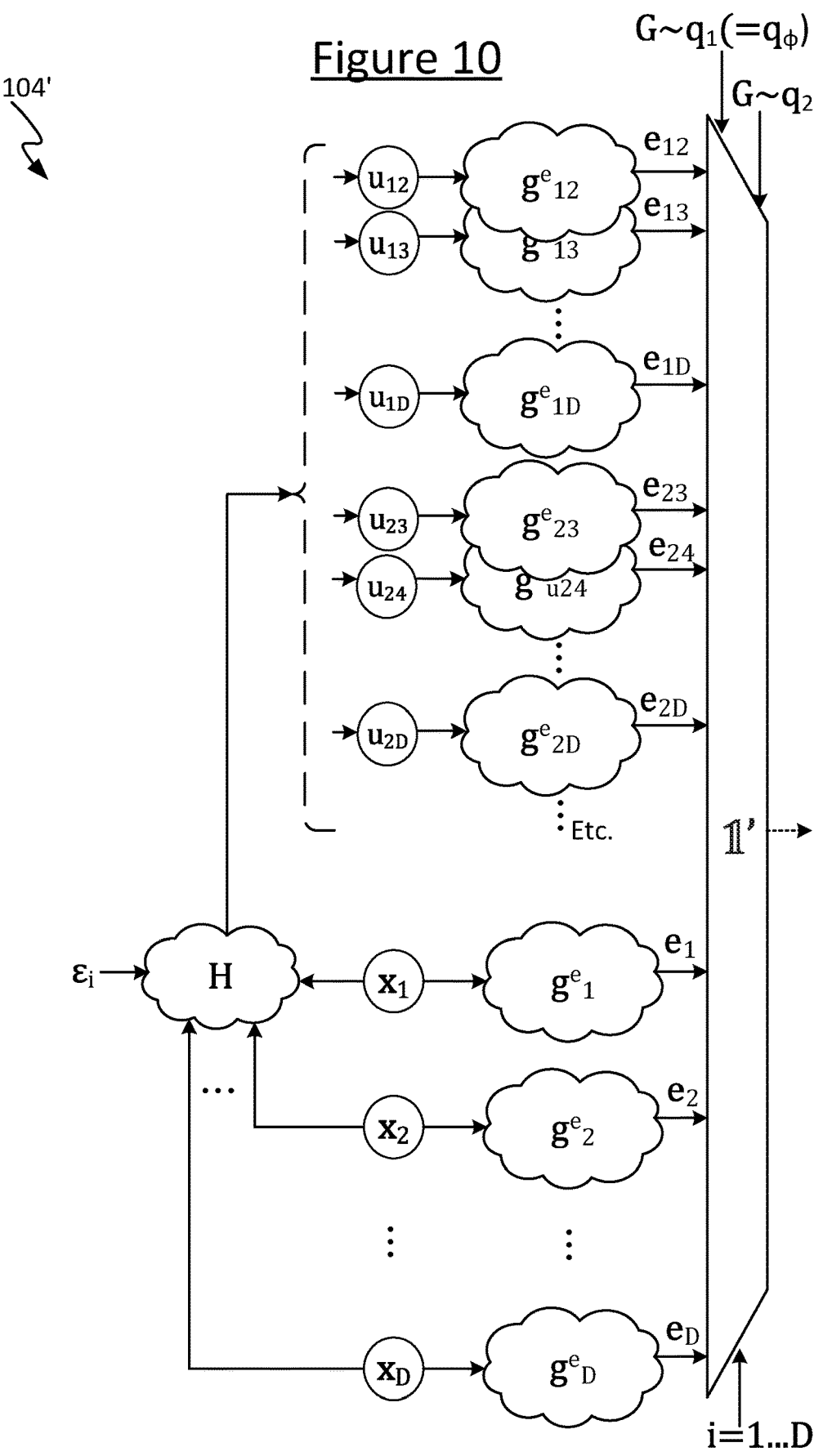
FIG. 10 is a schematic computation diagram illustrating a machine learning model that models the possible presence of hidden confounders in accordance with embodiments disclosed herein.

The extended model works in a similar manner to the model 104 described in relation to FIG. 2 and like elements function in the same manner except where stated otherwise. FIG. 10 schematically illustrates the extension to the model on the encoder side. The decoder side works the same as described in relation to FIG. 2.

As illustrated in FIG. 10, as in the base model 104 of FIG. 2, the extended model 104' comprises a respective first encoder $g^e_i$ for each variable $x_i$ (i.e. each feature) of the input feature vector $[x_1 \ldots x_D]$, each arranged to encode the value of its respective variable $x_i$ into a respective embedding $e_i$.

The extended model 104' additionally comprises an inference network H, and a respective second encoder $g^e_{ij}$ for each of a plurality of pairs of input variables $x_i$, $x_j$ in the input feature vector—preferably one for each possible pair (i.e. every combination of two variables from the input vector). For each of the plurality of pairs of variables $x_i$, $x_j$, the inference network H is arranged to encode the respective values of one or more of the input variables $x_1 \ldots x_D$ (e.g. in training, at least the two respective values of the pair together) into a respective latent value $u_{ij}$ for the respective pair. This latent value represents a modelled value of the (possible) confounder that potentially exists between respective pair of input variables $x_i$, $x_j$. The inference network H may also be a function of a pseudorandom noise term $\varepsilon_i$. These noises will be added as part of the input. That is, $u=H(x, \varepsilon)$, as shown in FIG. 10.

In embodiments, the inference network H is implemented as one common inference network that encodes all the variables $x_1 \ldots x_D$ together into the latent confounder value $u_{ij}$ for a given pair. Alternatively it is not excluded that the inference network H could be structured as a respective constituent inference network $H_{ij}$ for each of the plurality of pairs of input variables input variables $x_i$, $x_j$. Other internal structures of H are also possible.

The extended model 104' further comprises a respective second encoder $g^e_{ij}$ for each respective latent value $u_{ij}$ (corresponding to each respective pair of input variables $x_{ij}$). Each respective second encoder $g^e_{ij}$ is arranged to encode the respective latent value $u_{ij}$ of the respective confounder into a respective embedding $e_{ij}$.

The extended model 104' comprises a selector 1' analogous to the selector 1 described in relation to the base model of FIG. 2, but with additional functionality. As in FIG. 2, a causal graph $G_\phi$ is sampled from the graph distribution $q_\phi$, and a certain selected variable $x_i$ is selected; and the selector 1 then selects the parent variables $Pa_i$ that are parents of the selected variable $x_i$ according to sampled graph $G_\phi$, and inputs these into the combiner 202 (e.g. adder or concatenator). The graph distribution used for this is the same as the graph distribution $q_\phi$ described previously with respect to FIG. 2. I.e. it comprises matrix whose elements represent the probabilities of directed causal edges existing between the different possible pairs of variables in the input vector $[x_1 \ldots x_D]$. In the context of the extended model 104', this may also be described as the first graph distribution, or the directed graph distribution; and the graph sampled therefrom may be referred to as the first causal graph or the directed graph. In other words:

$$q_\phi = q_1 = q_{directed}$$

$$G_\phi = G_1 = G_{directed}$$

However, in addition, the extended model 104' also samples a second causal graph $G_2$ from a second graph distribution $q_2$. These may also be referred to herein as the bidirected graph distribution and bidirected graph:

$$q_2 = q_{bidirected}$$

$$G_2 = G_{bidirected}$$

The second graph distribution $q_2$ is a graph distribution representing the probabilities that confounders exist between pairs of variables. It may be expressed as a matrix in which the different elements represent the probabilities that there exists a confounder between different pairs of variables $x_i$, $x_j$, preferably having an entry for each possible pair of variables in the input feature vector $[x_1 \ldots x_D]$ (i.e. every combination of two variables from the input vector). So for a simple three variable input vector (D=3), the second graph distribution would have three entries:

$$\psi\_exists12$$

$$\psi\_exists13$$

$$\psi\_exists23$$

where $\Psi\_exists(i,j)$ represents the probability that a confounder exists between variables with indices i and j. More generally the second graph distribution $q_2$ may be expressed as:

$$q_2 = \begin{pmatrix} \psi\_exists1,\, 1 & & \\ \vdots & \ddots & \\ \psi\_exists1,\, D & \ldots & \psi\_exists(D-1),\, D \end{pmatrix}$$

Other equivalent representations may also be possible.

To sample an actual graph $G_2$ from the second graph distribution $q_2$, the presence or absence of each edge in the graph $G_2$ is determined pseudorandomly according to the probability specified in the corresponding element of the distribution $q_2$. E.g. if $\psi\_exists1,1=0.7$, then the element (1,2) in G2—representing whether or not a confounder $u_{12}$ exists between variables $x_1$ and $x_2$—has a 70% chance of being 1 (meaning confounder present) and a 30% chance of being 0 (meaning no confounder present). Again, other equivalent mathematical expressions of the same functionality are also possible. The value of the confounder, if it exists in the sampled graph $G_2$, taken from the output of the inference network H. In embodiments H may be configured to model a probabilistic distribution, which may also be described as a third distribution $q_3$, from which the values of $u_{ij}$ are sampled.

Based on the sampled graphs $G_1$ and $G_2$, in addition to the embeddings $e_i$ of the parents Pa(i) of the selected variable $x_i$ determined from the first causal graph $G_1$ (=$G_\phi$), as sampled from the first graph distribution $q_1$ (=$q_\phi$), the selector 1' also selects the embeddings $e_{ij}$ of any confounded pairs that include the selected variable $x_i$—i.e. of any confounders $u_{ij}$ that affect the selected variable $x_1$—as determined from the second causal graph $G_2$ sampled from the second graph distribution $q_2$. These embeddings $e_{ij}$ of the selected confounders $u_{ij}$ are input into the combiner 202 (e.g. adder or concatenator) along with the embeddings $e_i$ of the parents Pa(i) of the selected variable $x_i$. The combiner 202 then combines (i.e. sums or concatenates, depending on implementation) all of the embeddings $e_i$ of the selected parents and the embeddings $e_{ij}$ of the selected confounders together into a combined embedding $e_C$.

As shown in FIG. 2, the combined embedding $e_C$ is then input into the decoder $g^d_i$ associated with the selected variable $x_i$, which decodes the combined embedding to produce a respective reconstructed value $x_i'$ of the input variable $x_i$. Optionally the pseudorandom noise $z_i$ may be added (or included in some other, non-additive way) to create the noisy reconstructed value $X_i$. Either may be used as the simulated value of $x_i$. This side of the model 104' (the decoder side) works the same as in the base model 104, as described previously with respect to FIG. 2.

It will be appreciated that the inference network H, second encoders $g^e_{ij}$, and selector $\mathbb{1}$ may be implemented as modules of software in a similar manner to the other components as described in relation to the model of FIG. 2. As with the first encoders $g^e_i$ and decoders $g^d_i$, each of the inference network H and second encoders $g^e_{ij}$ may be implemented as a respective neural network, or alternatively other types of constituent ML models such as random forests or clustering algorithms, or any other form of parametric or non-parametric function, are not excluded.

Figure 11:
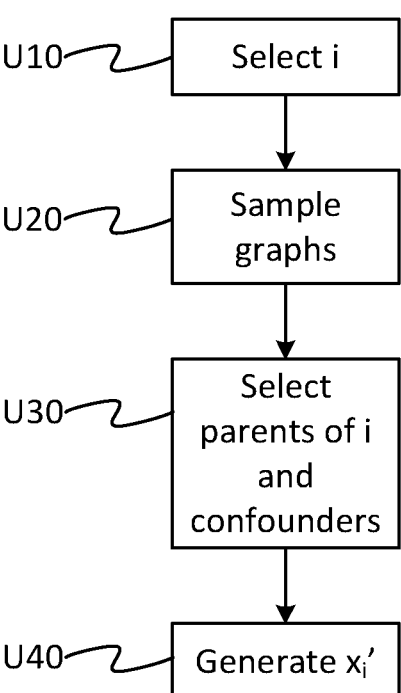
FIG. 11 is a schematic flow chart showing the core functionality of the model of FIG. 10, FIG. 12 schematically illustrates an example of a temporal causal graph.

The core functionality of the extended model 104' is represented in the flow chart of FIG. 11. By core functionality here, it is meant the mechanism of the model for sampling a causal graph that includes latent confounders, identifying parents of a selected variable according to the sampled graph, including any confounders, and then combining and decoding the embeddings of the identified parents, including the embeddings of any confounders. This mechanism may be used in both training and in subsequent treatment effect estimation.

At step U10 the method selects one of the variables $x_i$ from among the features of the input feature vector $[x_1 \ldots x_D]$. When used in training this variable $x_i$ is one of the variables to be reconstructed in order to determine a loss effect. When used in treatment effect estimation the selected variable $x_i$ will be the target variable, and the intervened-on variable (i.e. variable to be treated) will also be selected separately (though may be null). At step U20 the method samples a first causal graph $G_1$ from the first graph distribution $q_1$ and samples a second causal graph $G_2$ from the second graph distribution $q_2$. At step U30 the method determines which of the other variables $[x_1 \ldots x_{i-1}, x_{i+1} \ldots x_D]$ in the feature vector are parents Pa(i) of the selected variable $x_i$ in the sampled first graph $G_1$. Note this may involve mutilating the graph as described previously. The method also determines which of these parents Pa(i) share a confounder $u_{ij}$ with the selected variable $x_i$ in the sampled second graph $G_2$. In general this could be none, one, some or all of the parents Pa(i) identified from the first graph $G_1$.

At step U40 the method generates the reconstructed value $x_i'$ of the selected variable $x_i$. This is done by inputting the input values of each of the selected parents Pa(i) (as determined from the first graph $G_1$) into the respective first encoders $g^e_i$ in order to generate their respective embeddings $e_i$; and inputting at least the input value of the parent in each selected confounded pair $x_i$, $x_j$ (as determined from the second graph $G_2$) into the inference network H to generate the respective latent value $u_{ij}$, and inputting this into the respective second encoder $g^{eij}$ for the respective confounder in order to generate the respective embedding $e_{ij}$ for each respective pair of confounded variables. In some circumstances, the values input into the inference network H to generate the latent value $u_{ij}$ for a confounded pair i,j (and in turn the respective embedding $e_{ij}$) may also comprise one or more additional input values in addition to the parent of the respective pair. E.g. in training these one or more additional input values preferably comprise the observed input value of the selected variable as well. And in training or inference (e.g. treatment effect estimation), the one or more additional input values may comprise input values of one or more other of the variables of the feature vector $\{x_1 \ldots x_D\}$ (other than the selected variable $x_i$ or the respective parent $x_j$ of the pair i,j), as one or more of these variables may potentially also comprise information about the possible confounder. In general, H can generate $u_{ij}$ for the selected variable $x_i$ based on what is known about any or all of the other variables. The more is known, the better that H will predict $u_{ij}$. One (of many) ways to it is to take the average: $H(x_j) = $ sum over $x_i\{H(x_i, x_j)*p(x_j)\}$. So H can generate $u_{ij}$ from only a specified value of the parent $x_j$. H can even generate $u_{ij}$ given nothing as input, meaning H is just generating $u_{ij}$ randomly from a distribution learned at training. When estimating average treatment effects, this is acceptable, since in the one will marginalize out all the variables x in the entire population anyway.

Continuing step U40, all the generated embeddings $e_i$; $e_{ij}$ for the selected parents and confounders are input into the combiner 202 to be combined (e.g. summed or concatenated) into the combined embedding $e_C$, which is then decoded by the respective decoder $g^d_i$ for the selected variable $x_i$ to produce the respective reconstructed value $x_i'$. Optionally a noise term $z_i$ may be added to produce the simulated value $X_i$. Alternatively the noiseless reconstructed value $x_i'$ could be used as the simulated value.

It will be appreciated that FIG. 11 is somewhat schematized and all the steps of FIG. 11 do not necessarily have to be performed linearly. E.g. the method could identify the parents Pa(i) from the first graph and begin generating the parents' embeddings $e_i$ before it has begun identifying all of the confounded pairs $x_i$, $x_j$. Or the method could begin generating embeddings for some parents while still selecting other parents from the graph $G_1$, etc.

Training of the model 104' may be performed in an analogous manner to that already described in relation to FIGS. 2 and 7, by replacing steps S30-S70 in FIG. 7 with steps U10-U40 from FIG. 11. In other words, training begins with a given training data point comprising a set of respective values of at least some the variables (features) of the feature vector $\underline{x}_i = [x_1 \ldots x_D]$. Preferably this will be values of all the variables of the feature vector if available, but the function H can take any number of observations as input, so if one or more values are unobserved then they are simply not passed through H. The method then cycles through the indices of each variable i=1 . . . D observed in the feature vector, and for each performs the method of FIG. 11 with the current variable as the selected variable in order to produce a respective simulated value $x_i'$ or $X_i$. Over the cycle, the method will thus produce a simulated value $x_i'$ or $X_i$ for each variable in the feature vector (or at least those that are observed), which together thus result in a simulated feature vector $\underline{x}'=[x_1' \ldots x_D']$ or $\underline{X}_i=[X_i \ldots X_D]$. The method then determines a measure of the discrepancy between the input feature vector $\underline{x}_i$ and the simulated feature vector $\underline{x}_i'$ or $\underline{X}_i$ for the given training data point, and based on this tunes the parameters (e.g. weights) of all the constituent models (e.g. neural networks) of the ML model 104', including the first encoders $g^e_i$, second encoders $g^e_{ij}$, inference network H, and decoders $g^d_i$, as well as the first and second graph distributions $q_1$ and $q_2$. E.g. this may be done using an ELBO function, or any other suitable learning function. Algorithms for comparing an input feature vector with a simulated version in order to tune the parameters of a ML model are, in themselves, known in the art. The method may be repeated over multiple training data points in order to refine the training.

Once the model 104' has been trained to at least some extent, it may be used to estimate whether a likely confounder exists between a given target pair of variables $x_i$, $x_j$ (i.e. a pair of variables of interest). This may be done by accessing the trained second graph distribution $q_2$ from memory and reading out the value of the probability $\psi\_exists(i, j)$. If the probability is high (e.g. above a threshold) it may be determined that an unobserved confounder is likely to exist between the two variables $x_i$ and $x_j$, whereas conversely, if the probability is low (e.g. below a threshold) it may be determined that such a confounder is not likely to exists between the variables in question.

In dependence on this, a decision may be made as to whether or not to action a treatment on a first, intervened-on one of the two variables $x_j$ as a means of affecting a second, targeted one of the two variables $x_i$. Consider a scenario where $x_j$ is a apparently cause of $x_i$ according to the first graph distribution $q_1$, because the relevant elements—e.g. $\phi\_exists(l,k)$, $\phi\_dir(i,j)$—of the first graph distribution $q_1$ have been read out from memory and indicate a high probability (e.g. above a threshold probability) of a directed edge existing from $x_j$ to $x_i$. Thus from the first graph distribution $q_1$ alone, it may appear that treating $x_j$ is an effective way of affecting $x_i$. However, if $\psi\_exists(i, j)$ in the second graph distribution $q_2$ also indicates a high probability (e.g. above a threshold probability) of a hidden confounder existing between $x_j$ and $x_i$, then it may be determined that in fact $x_j$ should not be treated as a means of affecting target variable $x_i$.

The trained model 104' may also be used to estimate the value of such a confounder. This may be done by reading out the value of $u_{ij}$ from the output of the inference network after a suitable amount of training. In embodiments the inference network H may model a probabilistic distribution, which could also be described as $q_3$, from which the value $u_{ij}$ is sampled. The decision as to whether to action the treatment may also be dependent on the value of the estimated confounder. E.g. if a confounder is determined likely to be present but having a weak effect, it may be decided still to action the treatment of $x_j$ as a means of affecting target variable $x_i$.

In alternative or additional applications, the trained model 104' may be used to perform treatment effect estimation in an analogous manner to that already described in relation to FIGS. 2 and 8, by replacing steps T10-T40 in FIG. 8 with steps U10-U40 from FIG. 11. In other words, the target variable is selected as the selected variable $x_i$, and input values of one or more other, intervened-on (i.e. controlled) variables $x_j$ is/are set to its/their intended value (i.e. the proposed value for treatment). As discussed earlier the inference network H can take any number of observations, so if any variables are not intervened-on or observed, their values are simply not passed through H. The method of FIG. 11 is then used to generate a simulated value $x_i'$ or $X_i$ of the target variable $x_i$. In embodiments this may be repeated over multiple different sampled instances of the first and second causal graphs $G_1$, $G_2$; i.e. repeating the steps of FIG. 11 but newly re-sampling the first causal graph $G_1$ from the first graph distribution $q_1$ and the re-sampling the second causal graph $G_2$ from the second graph distribution $q_2$ afresh each time (while keeping the same selection of the target variable and the same fixed values of the intervened on variable or variables $x_j$). The estimated effect of the treatment may then be determined by averaging over these multiple rounds of graph sampling. E.g. this may comprise determining the average treatment effect (ATE) or any other averaging technique described previously with respect to FIGS. 2 and 8.

A decision about whether or not to action the proposed treatment of the (to-be) intervened-on variable or variables $x_j$ may be made in dependence on the estimated treatment effect. If the treatment is determined to be effective and to have a positive effect on the target variable $x_i$ (e.g. having above a threshold effect), then the treatment may be actioned; but otherwise the treatment may not be actioned.

Extension to Accommodate Time Series Data

Figure 12:
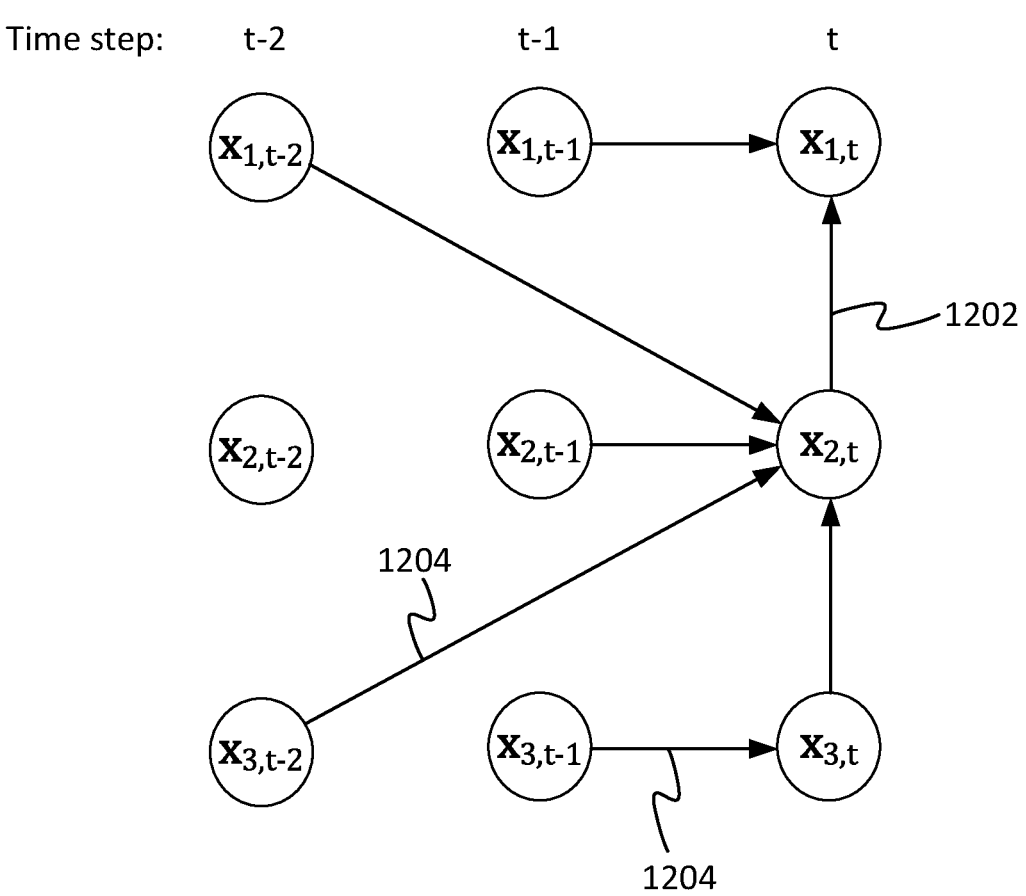

FIG. 12 illustrates the concept of a temporal causal graph by way of example. The modelled scenario may be divided into a series of two or more time steps, including a current time step t representing a present time, and one or more preceding time steps t–1, t–2, . . . representing one or more points in time in the past. Conceptually the nodes of the graph may be thought of as arranged into layers, each layer corresponding to a given time step. Each node in the graph represents a particular one of the variables of the input feature vector at a given time step. In the layer representing the present time t, the graph includes nodes representing a plurality of variables $x_{1,t} \ldots x_{D,t}$ of the feature vector at the present time (up to all the features of the feature vector). In the layer representing the first preceding time step t–1, the graph includes nodes representing a plurality of variables $x_{1,t-1} \ldots x_{D,t-1}$ at the previous time step. These may include some or all of the same variables $x_{1,t} \ldots x_{D,t}$ as included at the first time step, i.e. representing the same features of the feature vector, but instantiated at the preceding time step (the values of variables may change over time). Preferably it is the same set of variables as in the first time step. Similarly each further preceding layer before that (t–2 . . . t–T), if present, represents variables of the feature vector at earlier times going backward in time. Each layer may represent some or all of the same set of variables as included in other layers, but at different steps in time. In the case of more than two time steps, these may or may not be evenly spaced in time. Preferably the time steps are evenly spaced.

As well as edges 1202 between between nodes in the layer representing variables $x_{1,t} \ldots x_{D,t}$ at the present time t, the temporal graph is able to include one or more edges 1204 directed from the nodes representing one or more variables $x_{1,t-1} \ldots x_{D,t-1}; \ldots x_{1,t-T} \ldots x_{D,t-T}$ in layers representing one or more preceding steps in time t–1 . . . t–T to nodes in the layer representing variables $x_{1,t} \ldots x_{D,t}$ at the present time t. These could include an edge from a given variable at a preceding time step to the same or a different variable at the present time step. The edges could include an edge from a given variable in a preceding time step to a single other variable in the current time step, or from a given variable in a preceding time step to multiple variables at the present time step. The edges could include edges from a plurality of different variables in a given preceding time step, each to a respective set of one or more variables in the present time step, where the sets may or may not include one, some or all of the same variables. The edges could include edges from variables in a plurality of different preceding time steps, each to a respective set of one or more variables in the present time step, where again the sets may or may not include one, some or all of the same variables. In general there may be any combination of edges between any one or more variables of the feature vector at the present time step or any one or more preceding time steps and any one or more variables of the feature vector at the present time step; excepting only that edges between time steps must be directed forward in time, i.e. from a preceding time steps to the present time step. Preferably however, the graph formed by edges from present time steps to present time steps should not contain any directed cycles. (i.e. it should form a directed acyclic graph).

A particular instance of a temporal graph G may be sampled from a temporal graph distribution $q_\phi$ where $q_\phi$ now represents a temporal graph distribution rather than a static graph distribution as specified earlier. In other words $q_\phi$ now represents not only the probabilities of causal edges existing between various possible combinations of variables $x_{1,t} \ldots x_{D,t}$ at the present time t; but also from each of one or more of variables $x_{1,t-1} \ldots x_{D,t-1}; \ldots x_{1,t-T} \ldots x_{D,t-T}$ at one or more preceding time steps $t-1 \ldots t-T$ each to a respective one, more or all of the variables $x_{1,t} \ldots x_{D,t}$ at the present time step t. Preferably $q_\phi$ includes an entry representing the probability of an edge existing between every possible combination variables in preceding and present time-step layers.

As a temporal graph distribution, $q_\phi$ may now be expressed as a matrix: $q_\phi = \{q^\phi_t, q^\phi_{t-1}, \ldots, q^\phi_{t-T}\}$; where $q^\phi_t$ is the same as the static version of $q_\phi$ that was defined earlier in relation to FIG. 2, i.e.:

$$q_t^\varphi = \begin{pmatrix} \varphi\_\text{exists}1,2 & & & dir1,2 & \\ \vdots & \ddots & & \vdots & \ddots \\ \varphi\_\text{exists}1,D & \ldots & \varphi\_\text{exists}(D-1,D)' & dir1,D & \ldots & dir(D-1,D) \end{pmatrix}$$

Which could also be written as $q^\phi_t = \{\phi\_\text{exists}(i,j); \phi\_\text{dir}(i,j)\}$ counting through all modelled possible combinations of i and j.

The parameter $\phi\_\text{exists}(i,j)$ represents the probability that a causal edge exists between $x_i$ and $x_j$; and $\phi\_\text{dir}(i,j)$ represents the probability that the direction of the possible edge between $x_i$ and $x_j$ is directed from $x_i$ to $x_j$ (or vice versa). Other equivalent mathematical representations of the same functionality may also be possible. Note this submatrix $q^\phi_t$ is just for present time to present time, and so does not included existence of edges $\{1,1\}, \{2,2\} \ldots \{D, D\}$.

The other submatrices $q^\phi_{t-1} \ldots q^\phi_{t-T}$ modelling the distribution of edges from historical time steps do not contain entries for direction as edges from the past, if they exist, must always be directed forward in time. However these submatrices may include edges $\{1,1\}, \{2,2\} \ldots \{D, D\}$. Therefore $$q_{t-\tau}^\varphi = \begin{pmatrix} \varphi_\tau\_\text{exists}1,1 & \ldots & \varphi_\tau\_\text{exists}D,1 \\ \vdots & \ddots & \vdots \\ \varphi_\tau\_\text{exists}1,D & \ldots & \varphi_\tau\_\text{exists}(D,D) \end{pmatrix}$$

where $\tau=1 \ldots T$. In other words: $q^\phi_{t-\tau} = \{\phi_\tau\_\text{exists}(i,j)\}$ counting through all modelled possible combinations of i and j. The parameter $\phi_\tau\_\text{exists}(i,j)$ represents the probability that an edge exists between $x_i$ at past time $\tau$ and $x_j$ at the present time t. Again other equivalent mathematical representations of the same functionality may also be possible.

Figure 13:
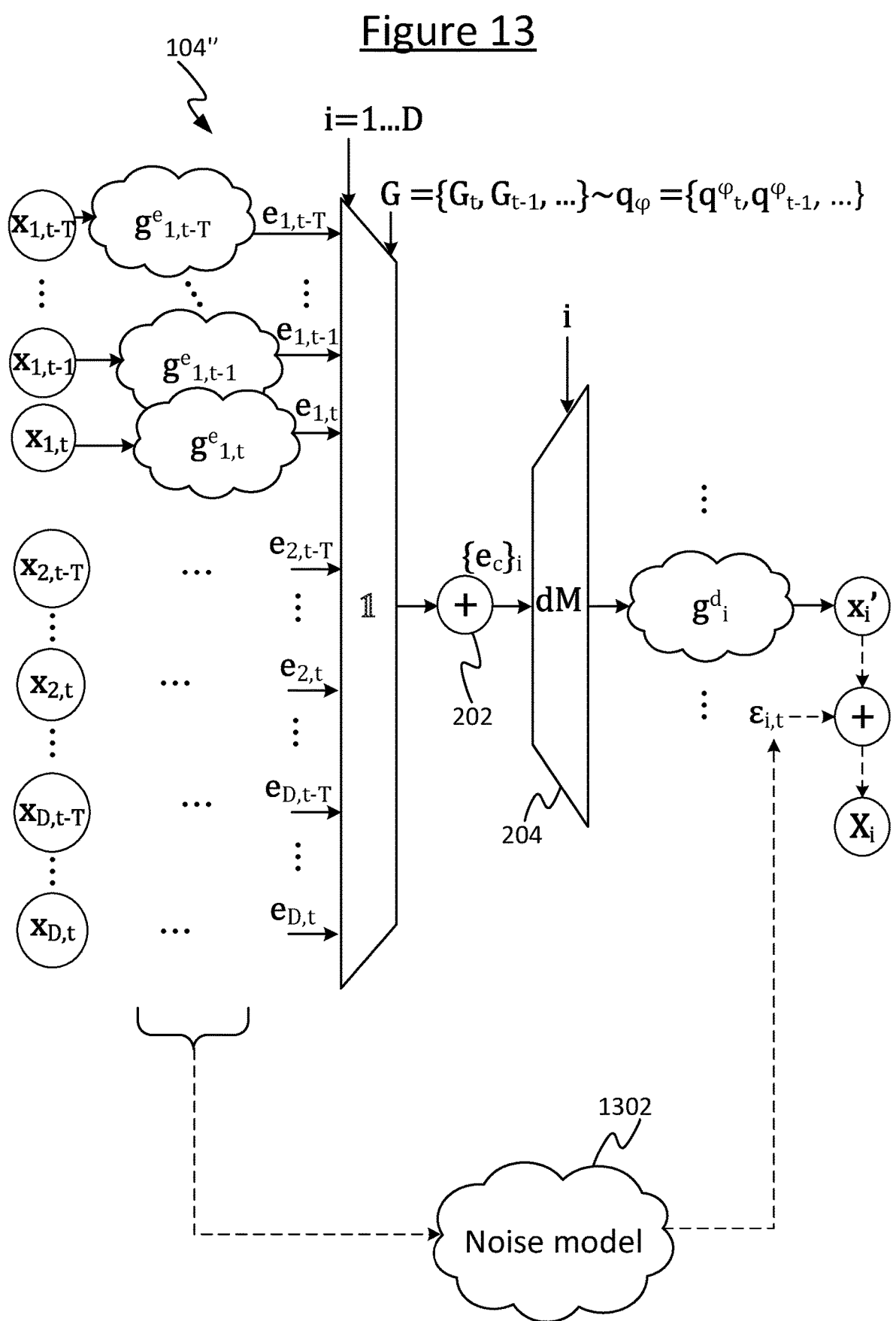
FIG. 13 is a schematic computation diagram illustrating a machine learning model that models temporal relationships between time series data in accordance with embodiments disclosed herein.

FIG. 13 shows schematically an extension of the model of FIG. 2 to accommodate the modelling of temporal causality using a temporal graph sampled from a temporal graph distribution. Based on this the extended model includes embeddings for different time steps.

The extended model 104" is the same as the base model 104 or 104' described in relation to FIG. 2 or 10, except where specified otherwise where the extended model 104" builds on the base model. As well as a respective first encoder $g^e_{i,t}$ for each of the variables $x_{i,t}$ at present time t, as in the model of FIG. 2, the extended model 104" also includes a respective first encoder $g^e_{i,t-\tau}$ for each of a plurality of the variables $x_{i,t-\tau}$ of the feature vector for each of the one or more preceding time steps $t-\tau$, where $\tau=1 \ldots T$. Each first encoder $g^e_{i,t}; g^e_{i,t-\tau}$ is arranged to receive an input value of its respective variable $x_{i,t}; x_{i,t-\tau}$ at its respective time step t, and to encode into a respective embedding $e_{i,t}; e_{i,t-\tau}$ for its respective combination of variable index i and time step t.

The selector 1 receives a selection of a particular selected variable of index i from among the variables (i.e. features) of the input feature vector $\{x_1 \ldots x_D\}$. The selector 1 also also takes as an input a particular sampled graph G from the graph distribution $q_\phi$, remembering that q is now a temporal graph distribution and so G may now be a temporal graph containing one or more edges from one or more variables at a past time $t-\tau$ to one or more variables at the present time t (depending on what edges get sampled from the distribution $q_\phi$ on any given graph sampling event). The edges present in G are determined to exist or not pseudorandomly according to the corresponding probabilities specified in the temporal graph distribution $q_\phi$.

The selector 1 then selects the parents $Pa_i$ that are causes of the selected variable $x_i$ in the sampled temporal graph G, including any parents from past time steps $t-1 \ldots t-T$. For these parents, the respective embeddings $e_{j,t}; e_{j,t-\tau}$ are generated from the respective encoder $g^e$, and the selector inputs these into the combiner 202 (e.g. adder or concatenator) to be combined (e.g. summed or concatenated) into the combined embedding $e_C$ for the selection variable $x_i$, which may also be written $\{e_C\}_i$ to indicate that it will vary with i. The combined embedding $e_C$ is input into the respective decoder $g^d_i$ associated with the selected variable in order to thereby generate a respective reconstructed value $x_i'$, in the same way as the decoder side of FIG. 2, except that this is now specifically the reconstructed value of the selected variable $x_i$ for in the present time step t.

Using a temporal graph can lead to more accurate predictions of treatment effects or the like since the model 104" has the capacity to more accurately reflect the causation of the modelled scenario, which may be temporal in nature. In embodiments, the model 104" may also be used to predict the best order in which to apply treatments, the best timing in which to apply one or more treatments, and/or to predict the likely timing of an effect of one or more treatments. In example use cases, the model 104" (once trained) may be used to determine treatments to apply to a data centre or cloud server system, by predicting the effects of one or more server units failing or being taken offline, or having a high load. In another example, the model 104" may be used to determine the order in which to apply controls in an autonomous vehicle or robot, or to apply certain actions in an industrial process or farming (e.g. when to apply pesticides and fertilizer, etc.).

In embodiments the reconstructed value may be combined (e.g. summed) with a noise term to generate the simulated value $X_i$. Alternatively the noiseless reconstructed value $x_i'$ could simply be used as the simulated value without including noise. If noise is included, this may be combined with the reconstructed value $x_i'$ as an additive noise term, or alternatively other non-additive means of combining a noise term with the reconstructed value $x_i'$ may be used. Either way, in some embodiments a static noise term $z_i$ as discussed previously could be used. However more preferably, the static noise term is replaced with a history-dependent noise term $\varepsilon_{i,t}$.

The history-dependent noise term $\varepsilon_{i,t}$ is a noise term that takes into account the values of the preceding parent variables $Pa_i^9(<t)$ of the selected variable $x_i$ in the sampled graph G. This means the model will take into account the past smoothness or noisiness of time series data in which at least one variable has different values over time. Thus by including the optional history-dependent noise term, the model 104'' will be a better specified representation of the real-world scenario being modelled, e.g. taking into account the level of fluctuation in a symptom of a patient, or a sensor reading measuring the state of a device or its environment, or traffic conditions experienced over a network, or a condition of a crop of plants, or so forth.

A simulated value $X_{i,t}$ that is determined based on a temporal causal graph G, and which includes history dependent noise, could be expressed as:

$$X_{i,t} = f_{i,t}\left[Pa_i^G(<t),\ Pa_i^G(t),\ \epsilon_{t,i}\right] \tag{1}$$

In embodiments disclosed herein, this formula is broken down and implemented as follows.

$$X_{i,t} = f_i\left[Pa_i^G(<t),\ Pa_i^G(t)\right] + g_i\left[Pa_i^G(<t),\ \epsilon_{t,i}\right] \tag{1a}$$

Equation 1 is not very practical in terms of modelling as it is too general. On the other hand Equation 1a (also called equation 5 later in the subsection "Example Implementation: Auto-Regressive DECI) breaks the representation down into a part that is based only on the parents from the present and preceding time steps, but not the noise; and a part that is based only on the parents from previous time steps and the noise, but not the parents from the present time step. If the model is too general as in Equation 1, then it may not work well as it cannot be identified from observational data alone. On the other hand if the model is made too specific, then it may also not work well because sometimes the data may violate the assumptions of the equation. The inventors have found that Equation 1a provides a good workable trade-off between specificity and generality.

Figure 14:
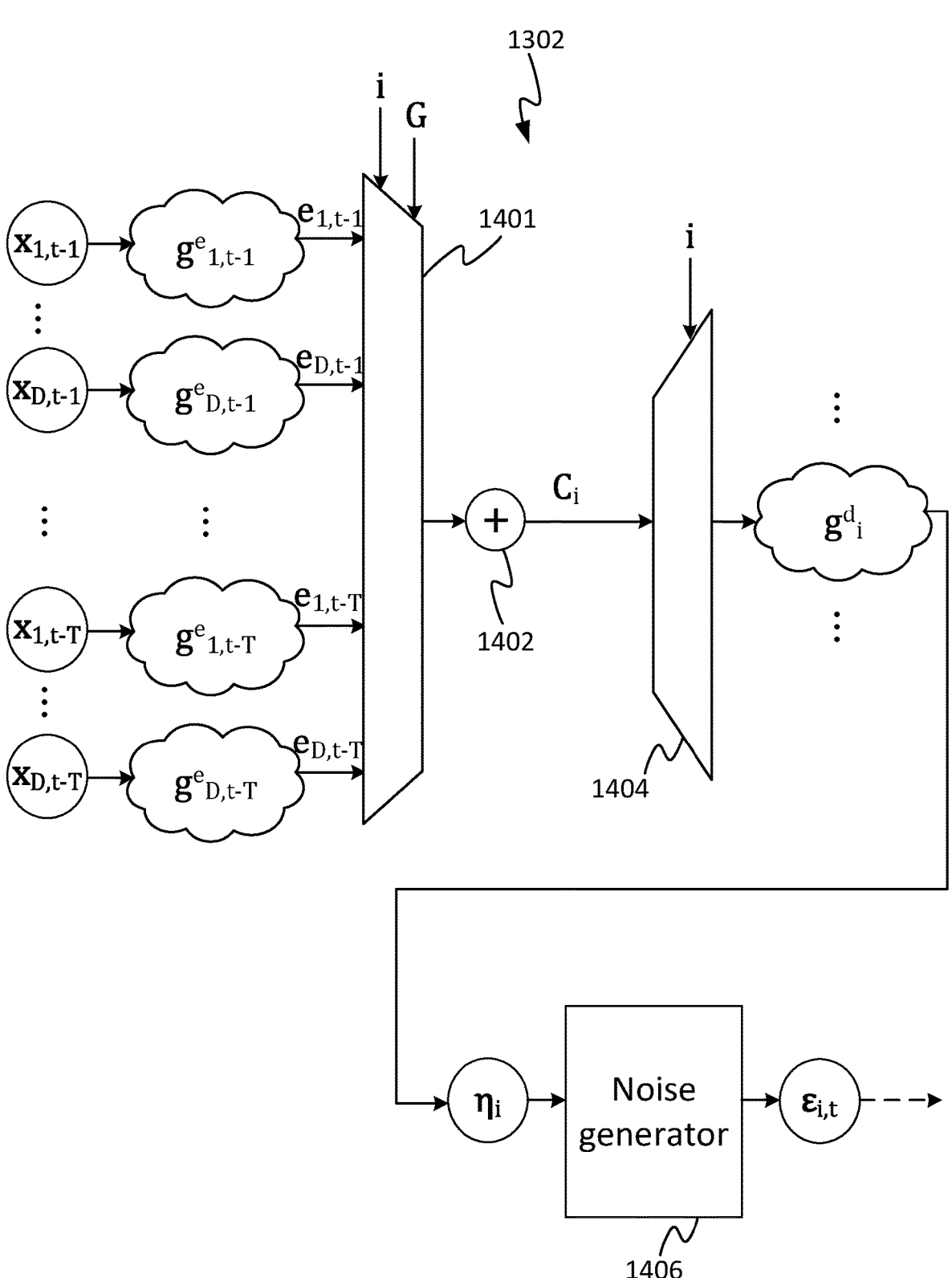
FIG. 14 is a schematic computation diagram of a history-dependent noise model in accordance with embodiments disclosed herein.

Equation 1a may be implemented as shown in FIGS. 13 and 14. The embeddings $e_{i,t-\tau}$ of the identified parents $Pa_i^G(<t)$ from any preceding times steps—but not the parents $Pa_i^G(t)$ from the current time step—are selected by a selector 1401 and input into a noise model 1302. In embodiments these are the same embeddings that you use to generate the reconstructed values $x_i'$ in FIG. 13, generated by the same encoders $g_i^e$. Alternatively however the embeddings used here in the noise model 1302 of FIG. 14 could be separate embeddings generated by separate encoder networks than used in FIG. 13. This selector 1401 may be implemented by some or all of the same code as the selector 1 (it will be appreciated that the figures are somewhat schematized and do not necessarily imply that the illustrated functions have to be implemented by separate modules of code). These embeddings $e_{i,t-\tau}$ are input into the history dependent noise model 1302 which is configured to generate the history-dependent noise term $\varepsilon_{i,t}$ in dependence on the input embeddings.

An example implementation of the history-dependent noise model 1302 is shown in FIG. 14. The noise model comprises a combiner 1402 (e.g. adder or concatenator), a demultiplexer 1404, and a respective decoder $g_i^d$ associated with each of the possible variables $x_i \ldots x_D$ that may be selected as the selected variable $x_i$. The combiner 1402 of the noise model 1302 may share some or all of the same code with the combiner 202 of the wider model 104/104'' as described previously with respect to FIGS. 2 and 13. The demultiplexer 1404 of the noise model 1302 may share some or all of the same code with the demultiplexer 204 of the wider model 104/104'' as described previously with respect to FIGS. 2 and 13. In embodiments, the decoders $g_i^d$ used here in the noise model 1302 of FIG. 14 may be different than those used to decode the combined embedding $e_C$ in the wider model 104/104'/104'' as described previously with respect to FIGS. 2 and 13. For example the $x_i'$ decoder would only output a single value: $x_i'$, but in embodiments the output $\eta_i$ that is the input to the noise generator 1406 actually has a slightly different form than the output of the decoder that produces $x_i'$. E.g. Specifically, $\eta_i$ might be the mean and variance (or standard deviation) of a distribution such as a Gaussian distribution (two values) and the noise generator 1406 would generate a sample from this distribution. Alternatively however, in other embodiments the same decoders $g_i^d$ may be used both to decode $\eta_i$ in the noise model 1402 of FIG. 14 and to decode $C_i$ in the wider model. Again it will be appreciated that the figures are somewhat schematized and do not necessarily imply that the components 1402, 1404 and $g_i^d$ are separate modules of code than those shown in FIG. 13).

The noise model 1302 further comprises a noise generator 1406. The combiner 1402 combines (e.g. sums or concatenates) the embeddings $e_{i,t-\tau}$ of the selected past parents $Pa_i^G(<t)$ into a further combined embedding $C_i$. The demultiplexer 1404 routes this further embedding $C_i$ into the respective decoder $g_i^d$ associated with the selected variable $x_i$. This decodes the embedding $C_i$ into a set of one or more parameter values $\eta_i$, which are the values of one or more parameters of a probabilistic distribution. The noise generator 1406 then generates the history dependent noise term $\varepsilon_{i,t}$ based on the probabilistic distribution as parameterized by the one or more parameter values. E.g. the probabilistic distribution could be a Gaussian or a spline function. FIG. 4 shows an example of a probabilistic distribution such as a Gaussian that may be parameterized by two parameters, a centre point (e.g. mean $\mu$) and a width (e.g. standard distribution a or variance $\sigma^2$). In one example implementation, the noise generator 1406 could generate the distribution parameterized by the parameter(s) $\eta_i$ (the mean $\mu$ and standard deviation $\sigma$), and then sample the value of the history dependent noise term $\varepsilon_{i,t}$ directly from the generated probabilistic distribution. Alternatively however, more preferably the noise generator 1406 implements the sampling by taking a sample $E_i$ from a fixed distribution, e.g. a unit distribution such as a unit Gaussian (with mean of 0 and standard deviation of 1), and then apply a transform function F which transforms the combination of the sample $E_i$ from the fixed distribution and the generated parameter(s) $\eta_i$ into a sample $\varepsilon_{i,t}$ from the parameterized distribution (without having to actually generate the entire parameterized distribution). In other words $\varepsilon_{i,t} = F(E_i, \eta_i)$.

The various encoders $g_{i,t}^e$; $g_{i,t-\tau}^e$; decoders $g_i^d$ and noise model 1302 may be implemented as modules of software as part of the model 104'', stored in memory and arranged to run on one or more processors in a similar manner as described previously in relation to FIG. 2.

The extended model 104'' may be trained in the same way as described previously with reference to FIGS. 2 and 7, but using a temporal graph sampled from the temporal graph distribution $q_\phi = \{q_t^\phi, q_{t-1}^\phi, \ldots q_{t-T}^\phi\}$ instead of a static graph sampled from the static graph distribution, and including the embeddings of the past parents $Pa_i^G(<t)$ as well as the present parents $Pa_i^G(t)$, and optionally also including the history dependent noise $\varepsilon_{i,t}$.

Figure 15:
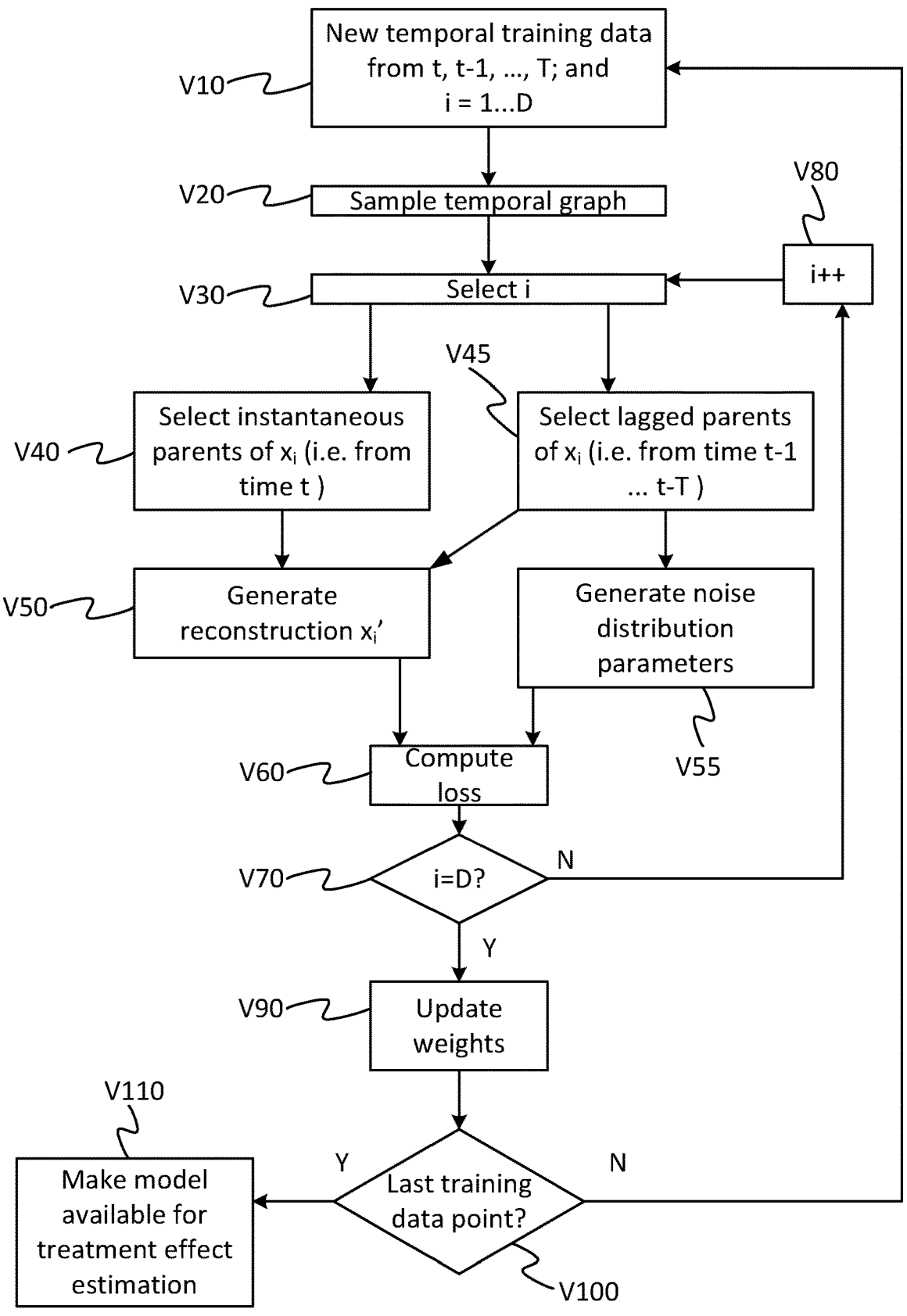
FIG. 15 is a schematic flow chart of a method of training the model of FIG. 13.

FIG. 15 shows the method of training the extended, temporal model 104''. At step V10 the method receives a new temporal training data point comprising values of some or all of the variables (features) of the feature vector $\{x_i \ldots x_D\}$ at two or more time steps. In embodiments it is all of the variables, but alternatively the model could be extended to handle missing data. At step V20 the method samples a temporal causal graph G from the temporal graph distribution $q_\phi=\{q^\Phi_t, q^\Phi_{t-1}, \ldots q^\Phi_{t-T}\}$. At step V30 the method selects a selected variable $x_i$ with index i from amongst the observed variables of the input feature vector.

At step V40 the method selects the instantaneous parents $Pa_i^G(t)$, i.e. from the present time step t, of the selected variable $x_i$. At step V45 the method selects the lagged parents $Pa_i^G(<t)$, i.e. from the one or more preceding time steps t–1 . . . t–T, of the selected variable $x_i$. At step V50 the method generates the noiseless reconstructed value of $x_i'$ of the selected variable $x_i$, by combining the embeddings $e_{i,t}$; $e_{i,t-1}$; . . . $e_{i,t-T}$ of the selected instantaneous and lagged parents. Optionally at step V55 the method also generates the history dependent noise $\varepsilon_{i,t}$. In embodiments however, only the noiseless reconstruction $x'_i$ is used during training, whereas the simulation $X_i$ with noise is used in treatment effect estimation. At step V60 the method determines the difference between the simulated value $X_i$ of the selected variable and the actual input value $x_i$. The simulated value may include the noise term, or in less preferred embodiments the noiseless reconstruction $x_i'$ could be used as the simulated value in step V60.

At step V70 the method loops back to step V30 via step V80 where it selects a new one of the observed variables of the feature vector, and repeats the method until reconstructed $x_i'$ values have been generated for the whole feature vector. At step V90 the method then updates the parameters (e.g. weights) of all the constituent models (e.g. NNs) which include at least the encoders $g^e$, decoders $g^d$ and temporal graph distribution $q_\phi$. The update is done based on the evaluating a measure of overall loss between the simulated value $\underline{X}_i$ or reconstructed value $\underline{x}'_i$, of the feature vector and the input value $\underline{x}_i$. E.g. this may be done using an ELBO function. In embodiments only the noiseless reconstruction is used during training, whereas the simulation with noise is used in treatment effect estimation. At step V100 the method loops back to V10 and repeats with a new training data point, tuning the parameters of the model 104" each time. This continues until the last training data point in the batch has been used, then the method proceeds to step V110 where the model 104" is made available to be used for making predictions, e.g. treatment effect estimation.

Figure 16:
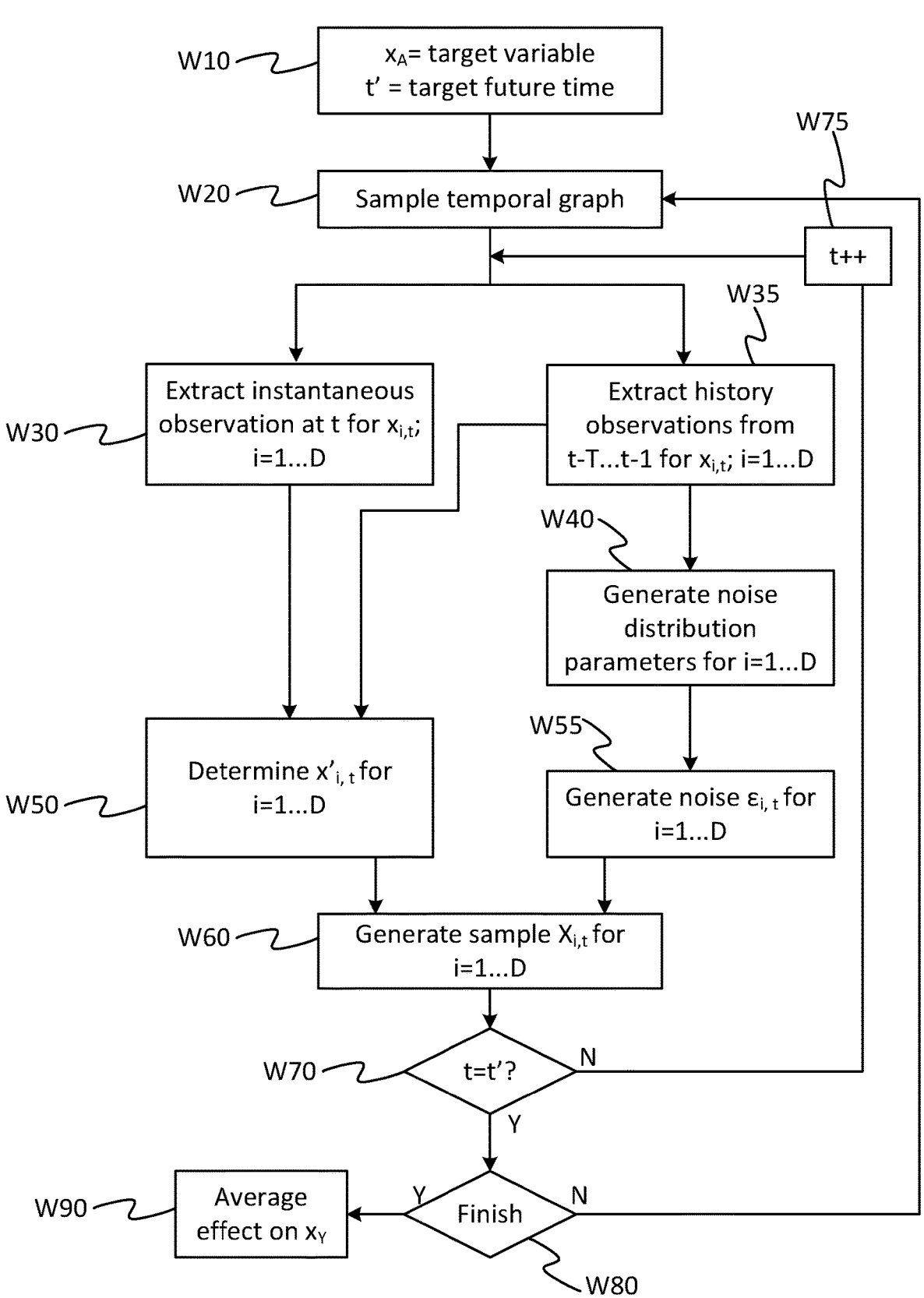
FIG. 16 is a schematic flow chart of a method of using the model of FIG. 13 for treatment effect estimation once trained.

The method of using the extended temporal model 104" to perform treatment effect estimation is analogous to that described earlier with reference to FIGS. 2 and 8. FIG. 16 shows a particular example method of using the model 104" to estimate that treatment effect that will be experienced at a future point in time.

At step W10 the method selects a target variable $x_A$ as the selected variable and a future time t' as a target time. A here is the value of the index i for the target variable. The method also selects at least one variable $x_B$ to be intervened on (i.e. treated). This may be referred to herein as the intervened-on variable, meaning the variable for a which an intervention (treatment) is proposed, i.e. an effect of intervening on that variable is to be estimated. B is the value of the index i of the intervened on variable $x_B$. The method also selects a value l of the proposed intervention on $x_B$, and a time t̃ as the time of the proposed intervention. The target time t' is the time for which the effect on the target variable is to be estimated, i.e. the time of interest. The time t̃ on the other hand is the time at which it is proposed to perform the intervention l on the intervened-on variable $x_B$.

The method begins with t=t̃ where t̃ is the start time, and at W20 samples a temporal graph G. At step W30 the method extracts instantaneous observations of the feature vector $\{x_i\}$, where i counts through the indices 1 . . . D of some or all of the features of the feature vector. This may include at least those that are observed and/or treated, and/or at least those that are immediate parents of the target variable i=A in the sampled graph. For any treated (i.e. intervened-on) variables x B these are set to their fixed, treated values l. For any observed values these are set to their observed values. In embodiments it may be assumed that observed or treated values are available for the entire feature vector at the start time t=t̃. At step W35 the method extracts any past observations of the feature vector $\{x_1 \ldots x_D\}$, i.e. for times t–T . . . t–1. At step W50 the method uses the values of the present and previous parents to generate the reconstructed value $x'_{i,t}$, cycling through the indices i=1 . . . D of some or all of the variables as the selected variable so as to reconstruct some or all of the feature vector in the manner discussed previously. The reason for reconstructing multiple variables, even though only one target variable $x_A$ may be ultimately of interest, is that when iterated over multiple time steps then these may have a knock-on effect on the target variable $x_A$ even if not immediate parents of $x_A$. At optional step W40 the method generates the noise distribution parameter(s) $\eta_i$, for some or all of i=1 . . . D, based on the historical data and sampled past parents, in the manner described previously; and then step W55 generates the history dependent noise based on this. At step W60 the method generates the simulated values $\{X_{i,t}\}$ for i=1 . . . D.

Note: the representation of steps W20-W60 in FIG. 16 may be somewhat of a simplification compared to the actual implementation. In embodiments these steps may be arranged into a sub-loop to count through i=1 . . . D, reconstructing each variable in turn, where the order of the indices from 1 to D preferably represent a topological order of the nodes in the sampled graph. That is, in the first cycle of the subloop the value of the variable i=1 with the highest topological order is determined, and then in the next cycle of the subloop the value of variable i=2 with the next highest topological order is determined, which may depend on the reconstructed or simulated value of the first variable, and so forth. Operating in this manner means that the method can takes into account that some variables may have a knock-on effect on others (not necessarily just their immediate parents). For example at a given t, $x_2$ might have knock-on effects on $x_3$ (or similar), and as such the sample $X_{i,t}$ can have an impact on $X_{j,t}$. The sub-loop will take account of this. This is shown in FIG. 17.

At step W70 the method loops back, via step W75 where t is incremented by one step, to the point of branching to steps W30/W35/W40. Each time the reconstructed or simulated values from the preceding step are fed back to the input of the model as the input values, unless intervened-on or observed values of the variables are of be used for any intermediate time steps between start time t=t̃ and target time t=t' in which case those values are used for those variables. The method continues repeating through to step W60 until future time t' is reached. After this the method proceeds to step W80 where, if not finished, it loops back to step W20 and repeats one or more times, resampling the graph at step W20 each time. Once the method has completed all the desired graph sampling loops, it finally proceeds to step W90 are an average treatment effect for the target variable $x_i$ of index i is determined averaged over all the sampled graphs.

The temporal graph is only sampled once throughout the entire time t to t'. Since there is additional time information, both the variable index i and a future time t' are specified (t'>=t) for the target variable. Therefore, in order to simulate a variable in the future, one needs to start with the current time t and simulate the all variables at the current time t (W30-W60). Then, one can proceed to simulate the variables at t+1. Repeat the above procedure until reaching t' (the loop of W70). This will generate simulation values of the target variable w.r.t the current temporal graph. Since it is desired to average multiple graphs, the procedure is then repeated one or more times (the loop of W80). Note also again that the flow charts may be somewhat schematized and in practice one or more steps and/or loops shown sequentially may in fact be performed in parallel.

Figure 17:
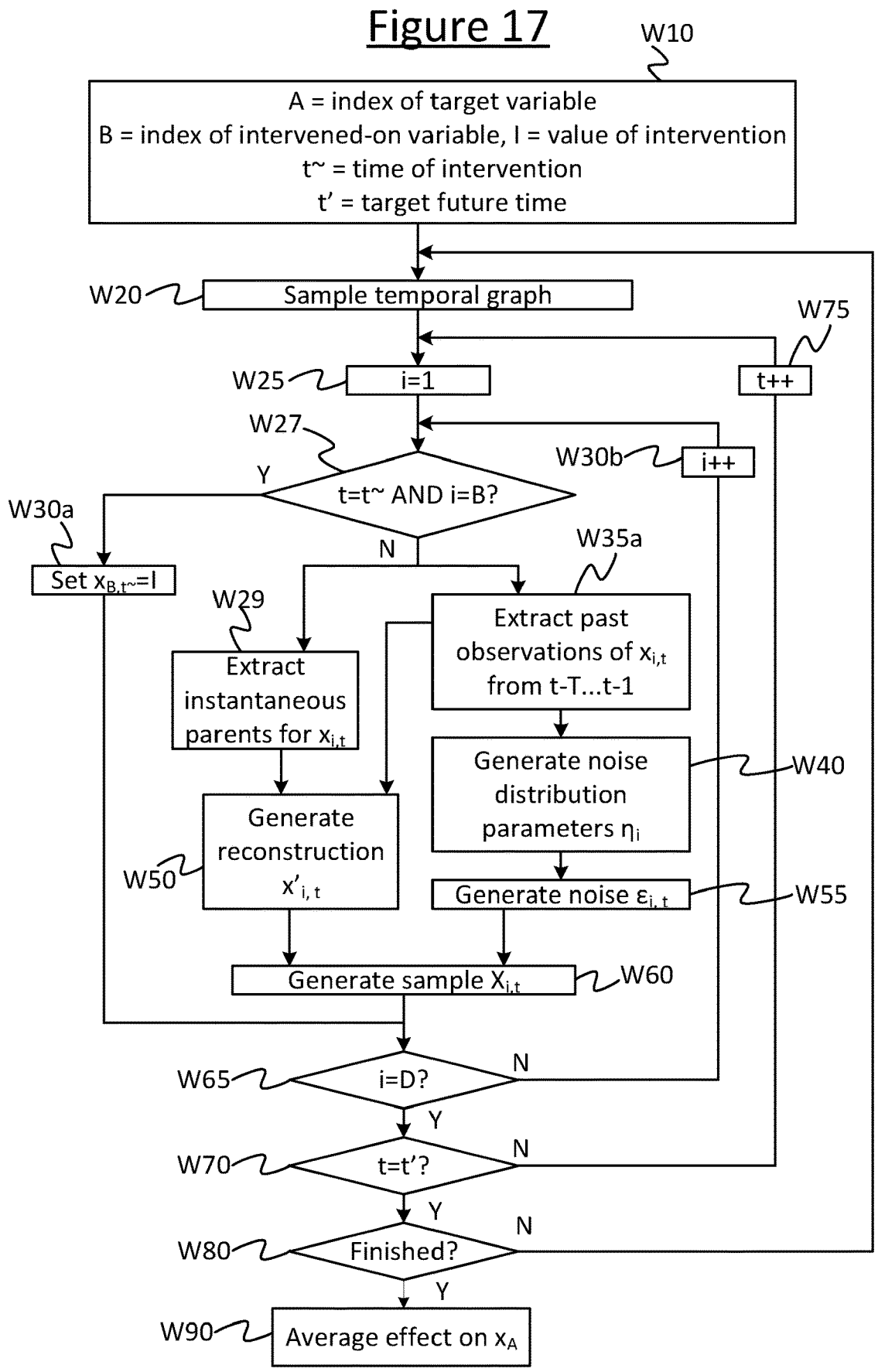
FIG. 17 gives additional exemplary detail expanding upon the flow chart of FIG. 16.

FIG. 17 shows explicitly the sub-loop mentioned previously with respect to steps W20-W60 of FIG. 16. FIG. 17 may be considered as a more detailed expansion of FIG. 16. At step W10 the method selects the variable $x_A$ with index i=A as the target variable, and selects at least one variable $x_B$ (index i=B) as the intervened-on variable, and l as the value of the intervention. The method also selects time $\tilde{t}$ as the time of the intervention and t' as the target future time. For example if the model 104" is being used to predict the effect of a heating control loop, $x_A$ could be the temperature of a target environment or device, $x_B$ could be the thermostat setting, l the value to which the thermostat is proposed to be set (the proposed treatment), time $\tilde{t}$ is the time of applying the thermostat setting, and time t' is the time for which it is desired to predict the resulting change in the temperature $x_A$. The method begins with the current time t set to an initial value, e.g. t=1, which could be the treatment time $\tilde{t}$ or a time earlier than the treatment time.

At step W20 the method samples a temporal graph G from the graph distribution $q_\phi$. At step W25 the method sets i=1. Preferably the index i counts in topological order of the nodes in the sampled graph, such that the variable $x_1$ indexed by i=1 has no parents, then the variable $x_2$ indexed by i=2 has either no parents or only $x_1$ as a parent, and so forth. At step W27 the method determines whether the current time t equals the treatment time $\tilde{t}$ AND the current value of the variable index i equals B, that of the intervened-on variable (i.e. treated variable) $x_B$. If both of these conditions are met then the method branches to step W30a where it sets the treated variable $x_B$ to the value of the intervention l. Though only a single treatment index value B is shown, more generally B could represent a set of one or more index values and l could represent a set of one or more corresponding intervention values, such that one or more variables i will be set to their corresponding intervened-on values l as the method counts though i via the loop W30b. Also, though not shown, optionally step W27 could check whether there exists an observed value of the current variable i for the current time t, and if so branch to W30a where that variable is set to its observed value. In other words, more generally step W27 could represent determining whether the current variable i at the present time t has a pre-specified value determined by some other means than reconstruction by the model 104" (whether because it is intervened-on or observed) and step W30a may represent setting any such variable to its specified value. In some cases the method could begin with a full set of observed and/or treated variables at the initial time t=1, such that at the initial time step all the variables of the feature vector are set to specified values.

If however it is determined at step W27 that the value of the present variable $x_{i,t}$ at index i at the present time t is not specified, then the method branches to step W29 where it extracts the values of any instantaneous parent(s) of $x_{i,t}$ from the sampled graph, and step W35a where it extracts the values of any lagged parents of $x_{i,t}$ according to the sampled graph. The method then proceeds to step W50 where it generates a noiseless reconstructed value $x'_{i,t}$ of the present variable $x_{i,t}$ for the present time t, using means as discussed previously in the description of the model 104". Optionally steps W45 and W55 are also performed to generate the history dependent noise term e a as also discussed previously. In this case then at step W60 the noise is added to (or otherwise combed with) the reconstructed variable $x'_{i,t}$ to generate the noisy simulated sample $X_{i,t}$ corresponding to the present variable $x_{i,t}$.

The method then proceeds to step W65 where it determines whether the counting index i has reached the value D of the index of the last variable in the feature vector (preferably sorted in topological order). If not the method branches to step W30b where it increments i by 1 and then loops back to step W25 and repeats until it has reconstructed the entire vector (or at least as much of it as is to be reconstructed). The steps W30a and W35a and the loop via W30b may be considered to correspond to the steps W30 and W35 in FIG. 16, in that steps W30a sets pre-specified (treated or observed) variables to their specified values and step W35 extracts the historical values, while the loop via W30b ensures that a reconstructed value $x'_{<i,t}$ is generated for any unspecified variable that comes before the present variable $x_{i,t}$ in the counting order (e.g. topological order). This is relevant since these variables $x'_{<i,t}$ could have an effect on the present variable. Counting through all variables i=1 ... D will mean that, over the entire count (i.e. all cycles of the subloop W27 to W30b), the past and present values of all the variables in the feature vector will be extracted as illustrated at a higher level of abstraction in steps W30 and W35 in FIG. 16.

If the last index D in the feature vector has been reached for the present time t, then at step W the method checks whether the present time t has reached the target time t' yet. If not, the method branches to step W75 where t is incremented by 1, and then loops back to step W25 where it repeats with the new value oft. When the method does reach the target time t', then the method proceeds to step W80 where it determines whether any more graphs are to be sampled. If so, the method loops back to step W20 where it repeats with a newly sampled temporal graph. Once the method has been repeated with the desired number of rounds of graph sampling, then it proceeds to step W90 where the average treatment effect on the target variable $x_A$ is determined, by averaging over the multiple sampled graphs as discussed previously.

Example Use Cases

The variables of the feature vector $x_i=[x_1 \ldots x_D]$ may represent properties of a tangible real-world entity being modelled, or an environment in which the entity resides. The entity may comprise a living being; or a physical object such as an electronic, electrical or mechanical device or system. Alternatively or additionally the object may comprise a piece of software running or to be run on a computer system.

In one example use case, the modelled real-world entity may comprise a living being, e.g. a human or animal. The disclosed model 104, 104' or 104" may be used to determine whether to action a treatment to the being in order to affect a condition of the being (e.g. to cure or alleviate a disease by which the being is afflicted). In this case the target variable $x_i$ represents a measure of the condition, e.g. a symptom experienced by the living being as a result of the condition, and one or more intervened-on variables $x_j$ represent one or more properties of the being or its environment which are susceptible to being controlled as a treatment (e.g. dosage of a drug, or a change in habit or environment, etc.). E.g. this may be used in a medical setting to treat a patient, where the potential treatment in question could be, for instance, a drug, surgery, or a lifestyle change. In another scenario the living being may comprise a plant or crop of plants, such as an agricultural crop, and the potential treatment could be the timing of sowing seeds, when to water or cover the plant/crop, or whether or when to apply a chemical such as a fertilizer or pesticide and/or in what quantity, etc. Whatever form the living being takes, a decision as to whether to perform the proposed treatment on the intervened-on variable(s) as a means to treat the target condition may be made in dependence on whether a confounder is estimated to exist between the proposed treatment and the target condition, and/or an estimate strength of the confounder. And/or, the decision may be made in dependence on the estimated treatment effect, e.g. ATE.

In another example use case, the real-world entity may comprise a mechanical, electrical or electronic system or device; and the disclosed model 104, 104' or 104" may be used to determine whether to action a treatment to affect a state of the system or device, such as to repair, maintain or debug the system or device. In this case the target variable $x_i$ may represent a measure of the state of the system or device, e.g. sensor data measuring wear, operating temperature, operating voltage, output or throughput, etc. The one or more intervened-on variables $x_j$ may represent one or more properties of the device or its environment susceptible to being treated, e.g. vibration, humidity, ambient temperature, applied current or voltage level, etc. E.g. this could be used in an industrial setting to service industrial equipment such as factory equipment. A decision as to whether to perform the proposed treatment on the intervened-on variable(s) as a means to treat the target state may be made in dependence on whether a confounder is estimated to exist between the proposed treatment and the target state, and/or an estimate strength of the confounder. And/or, the decision may be made in dependence on the estimated treatment effect, e.g. ATE.

In another example use case, the real-world entity being modelled may comprise software that is run, or to be run, on one or more processors in one or more computer devices at one or more locations; and the disclosed model 104, 104' or 104" may be used to determine whether to action a treatment to try to optimize the running of the software. In this case the target variable $x_i$ may comprise a measure of a current state of the software, e.g. memory or processing resource usage, or latency, etc. The one or more intervened-on variables $x_j$ may represent any property capable of affecting the running of the software, e.g. input data, or rebalancing or the load across a different combination of processors or devices. For example this could be used in a data centre or the cloud for load balancing of software run across different server devices. A decision as to whether to perform the proposed treatment on the intervened-on variable(s) as a means to optimize the running of the software may be made in dependence on whether a confounder is estimated to exist between the proposed treatment and the target state, and/or an estimate strength of the confounder. And/or, the decision may be made in dependence on the estimated treatment effect, e.g. ATE.

In another example use case the real-world entity being modelled may comprise a network, e.g. a mobile cellular network, a private intranet, or part of the internet (e.g. an overlay network such as a VoIP network overlaid on the network). The disclosed model 104, 104' or 104" may be used to determine whether to action a treatment to try to optimize the operation of the network. In this case the target variable $x_i$ may represent any state of the network that it may be wished to improve, e.g. a property of network traffic such as end-to-end delay, jitter, packet loss, error rate, etc. The one or more intervened-on variables $x_j$ may represent and property capable of affecting the target variable, e.g. balancing of traffic across the network, routing or timing of traffic, encoding scheme used, etc. A decision as to whether to perform the proposed treatment on the intervened-on variable(s) as a means to optimize the network performance may be made in dependence on whether a confounder is estimated to exist between the proposed treatment and the target state, and/or an estimate strength of the confounder. And/or, the decision may be made in dependence on the estimated treatment effect, e.g. ATE. The decision(s) may be made adaptively (i.e. dynamically in response to changing conditions), or as part of network planning.

In another example use case, the real-world entity may comprise an autonomous or semi-autonomous self-locomotive device such as a self-driving vehicle or robot. The disclosed model 104, 104' or 104" may be used to determine whether to action a treatment in the form of a control signal to control the motion of the device. In this case the target variable $x_i$ may represent sensor data providing information on the device's environment, e.g. image data or other sensor data (such as distance or motion sensor data) providing information on the environment of the device (such as presence of obstacles, location of another object to interact with). The one or more intervened-on variables $x_j$ may comprise a control signal that can be applied to control the device, e.g. to steer the vehicle or apply brakes or lights, or to move a robot arm in a certain way. A decision as to whether to perform a certain control operation (a type of "treatment") represented by the intervened-on variable, as a means to achieve a certain effect on the environment (e.g. avoid an obstacle or interact with another object), may be made in dependence on whether a confounder is estimated to exist between the proposed variable to be controlled and the target outcome, and/or an estimate strength of the confounder. And/or, the decision may be made in dependence on the estimated treatment effect, e.g. ATE.

Example Implementation: Auto-Regressive Deci

Further details of some example implementations of the various concepts discussed above are now described, by way of example only.

Identifying the causal relations between different variables is a question in many fields of scientific enquiry. Randomized control trial is the gold standard for discovering such relationships. However, it may not be always feasible due to practical or ethical reasons. Therefore, with no access to the interventional data, causal discovery may be used to discover the causal relations between different variables using the observational data. Recently, there has been a increasing trend towards causal discovery for time-series data. This is a relevant task in many fields of research including engineering, biology and medicine.

In a temporal system, one key underlying assumption that greatly simplifies the analysis is that the arrow cannot go against the flow of time. Causal discovery methods for temporal data may be based on the framework of Granger causality, stating that a variable in the past Granger causes another in the current time if the lagged one contains some unique information about the current one. These methods can be roughly categorized into (1) vector autoregressive based methods and (2) deep learning based approaches. However, one hidden assumption of Granger causality is that the time sampling interval is frequent enough such that no aggregation effect exists. In practice, this assumption can be easily violated, where the aggregation manifest itself as the instantaneous effect, i.e. the arrow between variables can exist within a time frame.

There is another line of research based on structure equation models (SEM), which can simultaneously model the lagged and instantaneous effect. The linear vector auto-regressive may be combined with non-Gaussian noise for causal discovery. For example a general structure equation model for time-series data, called TiMINo, provides a general theoretical framework for structure identifiability. The above methods assume that the noises are mutually independent and stationary in a way such that their distributions have independent (and learnable) parameters. However, this may not hold in many scenarios. For example, under education context, the observational noise of whether a student correctly answers a question should depend on his/her past learning history. If the student correctly answered similar past questions in a consistent way, the observational noise should be small. On the other hand, if the answer history is similar to a random guess, the observational noise should be large. This history-dependent noise distribution is ubiquitous in real life and cannot modelled by the aforementioned SEM.

To address the aforementioned issue, a particular embodiment of the present disclosure provides a novel SEM for time-series data based on the framework known as deep end-to-end causal inference (DECI) (Geffner et al, 2022). This may be named herein auto-regressive DECI (AR-DECI), which can model both non-linear lagged and instantaneous effect with history-dependent noise distribution. To implement this, the following contributions are provided.

A new formulation of temporal SEM with history-dependent noise, called AR-DECI, which combines SEM with vector auto-regressive to model both non-linear lagged and instantaneous effects. AR-DECI also adopts a Bayesian view of graph learning by using variational inference to approximate the graph posterior, which provides uncertainties over graphs under limited data. Also, we show one can compute interested treatment effect estimation by leveraging the fitted AR-DECI, e.g. conditional averaged treatment effect (CATE) with time-invariant interventions.

Theoretically, we show that the proposed AR-DECI is structure identifiable under assumptions. To achieve this, we provide a general framework for showing structure identifiability with history-dependent noise, where AR-DECI is a special case. Furthermore, we show AR-DECI unifies several aforementioned approaches based on SEM and Granger causality.

First we will briefly introduce necessary preliminaries required for building AR-DECI model. In particular, we will focus on the basic concepts of structure equation model, DECI (Geffner et al. 2022), and typical approaches for causal time series: Granger causality and vector auto-regressive models. Note that capital X may now be used to represent both input values and simulated values of the variables.

Structure Equation Models (SEM): Consider a multivariate time-series $X_t=(X_t^i)_{i \in V}$ where V is a set of nodes and $|V|=D$. SEM describes the functional relationships between individual variable $X_t^i$ across and within the time frame given a graph G. In particular, a general form of SEM is $$X_t^i = f_{i,t}\left(Pa_G^i(<t), Pa_G^i(t), \epsilon_{t,i}\right) \tag{1}$$

where $Pa_G^i(<t)$ contains the parent node specified by G in previous time frame (lagged parents) (i.e. parent nodes at time $t-1, t-2, \ldots$), $Pa_G^i(t)$ is the parent node at current time t (instantaneous parents), $\epsilon^{t,i}$ is the exogenous noise that is mutually independent to other variables in the model and $f_{i,t}$ describes the functional relationships between the parents and child node $X_t^i$. The above SEM induces a joint probability distribution over the entire time series $\{X_t\}_{t=0 \ldots T}$. Throughout the following, we make two underlying assumptions for SEM: (1) the function $f_i$ for all $i \in V$ and t is differentiable w.r.t all the arguments and (2) the induced joint distribution is absolutely continuous w.r.t the Lebesgue measure. Although the above form is very general, it is not very practical to be directly used for causal discovery due to the non-identifiability issue.

Deep End-to-end Causal Inference (DECI): Recently, Geffner et al. (2022) disclosed an end-to-end framework, called DECI, for causal inference with static data. DECI is based on a specific type of SEM, name additive noise model (ANM), which is structure identifiable under mild conditions. Specifically, the SEM of DECI is defined as:

$$X_i = f_i[Pa_G(X_i)] + \epsilon_i \tag{2}$$

where we drop its dependence of time t compared to Eq. (1) due to its static nature, and $\epsilon_i$ is the additive independence noise. DECI also adopts a Bayesian view for graph learning by applying variational inference to approximate the graph posterior $p(G|D)$ where D is the training dataset. By leveraging the trained DECI, one can not only perform causal discovery but also inference tasks such as estimating (conditional) average treatment effect, which provides us an end-to-end pipeline from observation data to the interested causal quantities.

Granger Causality: Granger causality has been extensively used as the underlying principle for identifying causal relationships in time series data. It is based on the idea that $X^i$ does not Granger causes $X_t^j$ if the history of $X^i$ does not help the prediction of $X_t^j$ given the past of all other time series $X_k$ for $k \neq i$. Formally, we can express Granger causality under the SEM framework:

Definition 1 (Granger Causality): Given a multivariate stationary time series $\{X_t\}_{t=0 \ldots T}$ and a SEM fi defined as:

$$X_t^j = f_{j,t}\left[Pa_G^i(<t), \epsilon_{t,j}\right] \tag{3}$$

where $Pa_G^i(<t)$ is the lagged parents of node $X_t^j$ and $\epsilon_{t,j}$ is the independent noise. Under this setup, time-series i Granger causes j if $\exists l \in [1, t]$ such that $X_{t-l}^j \in Pa_G^i(<t)$ and $f_{j,t}$ depends on $X_{t-l}^i$.

It has been shown that Granger causality is equivalent to causal relations for directed acyclic graph (DAG) if there are no latent confounders and instantaneous effect. One shortcoming of Granger causality is its incapability of handling the instantaneous effect, which can happen when the time sampling interval is not frequent enough.

Vector Auto-regressive Model: To overcome the aforementioned issue of Granger causality, another line of research focuses on directly fitting the identifiable SEM to the observational data with instantaneous parents. One typical approach is called vector auto-regressive model with the SEM defined as:

$$X_t^i = \beta^i + \sum_{\tau=0}^{K}\sum_{j=1}^{D} B_{ji}^\tau X_{t-\tau}^j + \epsilon_{t,i} \qquad (4)$$

where $\beta^j$ is the offset, $\tau$ is the lag, $B^\tau \in \mathbb{R}^{D \times D}$ is the weighted adjacency matrix specifying the connections in the DAG (i.e. if $B_{ji}^\tau=0$ means no connection between $X_{t-\tau}^j$ to $X_t^i$) and $\epsilon_{t,i}$ is the independent noise. Under certain assumptions, the above SEM has been shown to be structure identifiable, which validates its usage in causal discovery/inference tasks.

However, in real life, linear relationship is too restricted to capture the complex data generating mechanism and noise distribution may also be history-depended as described earlier. Therefore, a crucial research question is how to design an SEM for such effects with structure identifiability guarantees.

AR-DECI: Auto-Regressive Deep End-To-End Causal Inference

In this subsection, we will first focus on formulating the SEM of AR-DECI, followed by disclosing a variational objective with continuous DAG relaxation for training. In the end, we will discuss how to estimate CATE with time-invariant interventions.

Model formulation: For a multivariate stationary timeseries $\{X_t\}_{t=0 \ldots T}$ with a set of nodes V and $|V|=D$, we assume it follows a temporal graph adjacency matrix $G_{0:K}$ where K is the maximum lag K. We define $G_{\tau,ij}=1$ means there is a directed connection $X_{t-\tau}^i \rightarrow X_t^j$, and 0 means no connection. In the following, we interchange the usage of the notation G and $G_{0:K}$ for brevity. We provide the following SEM for AR-DECI:

$$X_t^i = f_i(Pa_G^i(<t), Pa_G^i(t)) + g_i(Pa_G^i(<t), \epsilon_{t,i}) \qquad (5)$$

where $f_i$, $g_i$ are general differentiable non-linear functions, $Pa_G^i(<t)$ is the lagged parents of node $X_t^i$ specified by adjacency $G_{1:K}$, $Pa_G^i(t)$ is the corresponding instantaneous parents specified by $G_0$, and $\epsilon_{t,i}$ is the independent noise. We also assume the above model satisfies causal Markov and minimality conditions. The above SEM has a similar additive structure as ANM, which has been leveraged in previous work to develop causal time-series models. A distinction of AR-DECI is that the noise $\epsilon_{t,i}$ is transformed by a non-linear history-dependent function $g_i$, meaning that the transformed noise distribution is history dependent and may not be independent to the other variables.

For the detailed design of the non-linear function fi, it should respect the relationships specified by graph $G_{0:K}$. Namely, if $X_{t-\tau}^j \notin Pa_G^i(<t) \cup Pa_G^i(t)$, then $\partial f_i / \partial X_{t-\tau}^j=0$. Building on the design of DECI, we disclose:

$$f_i(Pa_G^i(t), Pa_G^i(t)) = \zeta_i \left( \sum_{\tau=0}^{K}\sum_j^{D} G_{\tau,ji} \ell_{\tau j}(X_{t-\tau}^j) \right) \qquad (6)$$

where $\zeta_i$ and $\ell_{\tau i}$ (i=1, . . . ,D and $\tau$=0, . . . ,K) are MLPs. To reduce the number of neural networks, we adopts a weight sharing scheme across nodes and lags: $\zeta_i(\bullet)=\zeta(\bullet, u_{0,i})$ and $\ell_{\tau j}(\bullet)=\ell(\bullet, u_{\tau,j})$, where $u_{\tau,i}$ is the trainable embedding for node i at time $t-\tau$.

For the design of the noise transformation gi, it allows very flexible design choices. For the ease of evaluation and training, we limit our choice to be a conditional normalizing flow. Specifically, we choose conditional spline flow for $g_i$ with Gaussian noise $\epsilon_{t,i}$ for all t and i. Due to the invertibility of $g_i$, we have:

$$p_{g_i}(g_i(\epsilon_{t,i}) \mid Pa_G^i(<t)) = P_\epsilon(\epsilon_{t,i}) \left| \frac{\delta g_i^{-1}}{\delta \epsilon_{t,i}} \right| \qquad (7)$$

where we omit the dependency of $g_i$ with $Pa_G^i(<t)$ for clarity.

Variational Inference for AR-DECI

AR-DECI adopts a Bayesian view of causal discovery, which aims to learn a graph posterior distributions instead of inferring a single graph. For N observed multivariate time series $X^{(1)}_{0:T}, \ldots, X^{(N)}_{0:T}$, the joint likelihood of AR-DECI is:

$$p(X_{0:T}^{(1)}, \ldots, X_{0:T}^N, G) = p(G)\prod_{n=1}^{N} p_\theta(X_{0:T}^{(n)} \mid G) \qquad (8)$$

where $\theta$ is the model parameter. Once fitted, the posterior $p(G|X^{(1)}_{0:T}, \ldots, X^{(N)}_{0:T})$ incorporates the belief of the underlying causal relationships.

Graph Prior: To design a proper graph prior, we aim at three criteria: (1) constrain the graph to be a DAG; (2) favour sparse graph; (3) support prior knowledge. We choose the prior as:

$$p(G) \propto \exp(-\lambda_s \|G_{0:K}\|_F^2 - \rho h^2(G_0) - \alpha h(G_0) - \lambda_p \|G_{0:K} - G_{0:K}^p\|_F^2 \qquad (9)$$

where $h(G)=tr(e^{G \odot G})-D$ is the DAG penalty proposed in and is 0 if and only if G is a DAG; $\odot$ is the Hadamard product; $G^P$ is the prior knowledge of the graph; $\lambda_s$, $\lambda_p$ specifies the strength of the graph sparseness and prior knowledge, respectively; $\alpha$, $\rho$ characterize the strength of the DAG penalty. Since the connections from the history node to the current one can only follow the direction of the time flow, only the instantaneous connections can violate the DAG constraint. Thus, DAG penalty is only applied to $G_0$.

Variational Objective: Unfortunately from the Bayes' rule, the exact graph posterior $p(G|X^{(1)}_{0:T}, \ldots, X^{(N)}_{0:T})$ is intractable due to the large combinatorial space of all DAGs. To overcome this challenge, we adopt variational inference, which uses variational distribution $q_\varphi(G)$ to approximate the true posterior. We choose independent Bernoulli distribution for each directed edge as $q_\varphi(G)$. We derive the evidence lower bound (ELBO) as:

$$\log p_\theta\left(X_{0:T}^{(1)}, \ldots, X_{0:T}^{(N)}\right) \geq \tag{10}$$

$$\underbrace{\mathbb{E}_{q_\phi(G)}\left[\sum_{n=1}^{N}\log p_\theta\left(X_{0:T}^{(n)} \mid G\right) + \log p_\theta(G)\right]}_{ELBO(\theta,\phi)} + H(q_\phi(G))$$

where $H(q_\varphi(G))$ is the entropy of the variational distribution. From the causal Markov assumption and auto-regressive nature, we can derive:

$$\log p_\theta\left(X_{0:T}^{(n)} \mid G\right) = \sum_{t=0}^{T}\sum_{i=1}^{D}\log p_\theta\left(X_t^{i,(n)} \mid Pa_G^i(<t), Pa_g^i(t)\right) \tag{11}$$

and $$\log p_\theta\left(X_t^{i,(n)} \mid Pa_G^i(<t), Pa_G^i(t)\right) = p_{g_i}\left(z_t^{i,(n)} \mid Pa_G^i(<t)\right) \tag{12}$$

where $z^{i,(n)}_t = X^{i,(n)}_t - f_i[Pa^i{}_G(<t), Pa^i{}_G(t)]$ and $p_{gi}$ is defined in Eq. (7). The parameters $\theta$, $\varphi$ are optimized by maximizing the ELBO, where a Gumbel-softmax trick is used to estimate the gradients w.r.t $\varphi$.

Treatment effect estimation: We now show how to leverage the fitted AR-DECI for estimating the CATE. For simplicity, we only consider a special case of CATE defined as:

$$CATE(a, b) = \tag{13}$$

$$\mathbb{E}_{q_\phi}\left[\mathbb{E}_{p\left(X_{t+\tau}^Y \mid X_{<t}, do\left(X_t^I = a\right), G\right)}\left[X_{t+\tau}^Y\right] - \mathbb{E}_{p\left(X_{t+\tau}^Y \mid X_{<t}, do\left(X_t^I = b\right), G\right)}\left[X_{t+\tau}^Y\right]\right]$$

We assume the conditioning variable can only be $X_{<t}$ (i.e. the entire history before t), and the intervention and target variable can only be either at current time t or sometime in the future t+$\tau$. This formulation is for simplicity, and AR-DECI can be easily extended to more general cases using the CATE tricks in DECI (Geffner et al). Once fitted, the idea is to draw target samples $X^Y_{t-\tau}$ from the interventional distribution $p(X^Y_{t+\tau}|X_{<t}, do(X^I_t),G)$ for each graph sample $G \sim q_\varphi$ (G). Then, unbiased Monte Carlo estimation can be used to compute CATE. For sampling from the interventional distribution, we can use the "mutilated" graph $G\_do(X^I_t)$ to replace G, where all incoming edges to $X^I_t$ are removed. The intervention samples can be obtained by simulating the AR-DECI with history $X_{<t}$, $X^I_t = a$ or b and $G\_do(X^I_t)$.

Example Implementation: Confounded Deci

Further details of some example implementations of the various concepts discussed above are now described, by way of example only.

As discussed earlier, in practice it is not always possible to directly perform interventional studies (i.e., randomised AB testings) to estimate treatment effects, and it may be required to use observational studies. That is, the causal graph and the associated causal effects are to be inferred based on observational data, in embodiments solely based on observational data. Therefore, this would appear to require an assumption that all the data provided by users already contains all the information that is needed (i.e. there should not be any unmeasured confounders). However, this assumption is often unrealistic, as the modelled scenario is also impacted by certain variables that cannot be directly measured.

Therefore, it would be desirable to provide an effective and theoretically principled strategy for handling latent confoundings when performing joint causal discovery & inference. However, the existence of unmeasured confounding poses questions for causal discovery since there might exist multiple contradicting causal structures that are compatible with observations. Traditional methods for causal discovery mainly focus on estimating the causal relationships between observed variables and does not recover the causal relationships that involve unmeasured confounders. There also exists several related methods for causal discovery with latent confounders, but each comes with certain limitations on assumptions. Following the previous work by Geffner at al of developing deep end-to-end causal inference (DECI), this framework can be extended in order to handle latent confounders. The outcomes of this is to implement latent variable variants/baselines of DECI that explicitly take latent confounders into account. These variants/baselines should preferably: 1), be able to perform joint graph learning and functional learning; 2), have computational costs comparable to DECI; and 3), subsume DECI, in the sense that it should perform similarly to DECI when there is no latent confounders.

To recap the causal discovery without latent confounders using DECI, recall that in DECI, we perform causal discovery under no latent confounder assumptions, but modelling the causal graph G on all observed vertexes X jointly with the observations $x^1, \ldots, x^N$ as:

$$p_\theta\left(x^1, \ldots, x^N, G\right) = p(G)\prod_n p_\theta\left(x^n \mid G\right) \tag{1}$$

Here, p(G) is a prior over DAG, implemented by:

$$p(G) \propto \exp\left(-\lambda_s\|G\|_F^2 - \rho h(G)^2 - \alpha h(G)\right) \tag{2}$$

where G is the adjacency matrix representation, and $$h(G) = tr\left(e^{G\odot G}\right) - D \tag{3}$$

is the DAG penalty.

We aim to fit $\theta$, the parameters of our non-linear ANM, using observational data by maximizing (an lower bound of) log $p_\theta(x^1, \ldots, x^N)$. Given $\theta$, the question of causal discovery can be simply answered by the posterior, $p_\theta(G|x^1, \ldots, x^N)$. In the original DECI, we maximize the ELBO of log $p_\theta(x^1, \ldots, x^N)$ and use mean-field approximation $q\varphi(G)$ to perform approximate inference.

Causal discovery under ADMGs: in the present disclosure, we will extend DECI's framework to consider unmeasured confounders. Unfortunately, if some variables in a DAG is unobserved, the resulting set of (conditional) independences no longer corresponds to a DAG (on the observed variables).

To deal with unobserved variables, a common extension is the so called acyclic directed mixed graphs (ADMGs). In a ADMGs, a bidirected edge x↔y indicates the existence of a unmeasured founder $u_{xy}$, such that x←$u_{xy}$→y. Note that this would be different than a undirected edge x-y used in (CP)DAG, which indicates either x←y or x→y. Finally, the term acyclic in ADMG means that there is no cycles that contains only directed edges.

Therefore, causal discovery under latent confounders can be formulated as the same equation as the original DECI, $$p_\theta(x^1, \ldots, x^N, G) = p(G)\prod_n p_\theta(x^n \mid G) \tag{4}$$

except that the prior p(G) will be based on the constraint that G is a ADMG (instead of a DAG). We will discuss how to parameterize the ADMG constraint and how to parameterize $p_\theta(x^1, \ldots, x^N, G)$ later.

Note that in principle, an ADMG causal discovery algorithm is able to express search results using (a subset of) the following structures:

x→y: x is the cause of y;

x↔y: indicates the existence of a unmeasured founder $u_{xy}$, such that x←$u_{xy}$→y.

x-y: either x←y or x→y.

x⇒y: either x↔y, or x→y.

In the following, we mainly consider representing our posteriors using the first two, where they have better granularity than the last two.

D-DECI (Deconfounded DECI)

Magnification-based representation: We perform causal discovery on the highest granularity, i.e. explicitly model the latent confounders (denoted by U), and learn a DAG G' on X∪U. In other words, G' (on X∪U) is a magnification of G (on X); and the marginalized graph G over observed variables X will then be a ADMG. To relate G' to the previous notation of $G_1$ and $G_2$, $G_1$ is the adjacency matrix on X; and $G_2$ is the adjacency matrix on U. G' is basically a big matrix on both X and U, obtained by concatenating and unpacking $G_1$ and $G_2$. In other words, G'=M($G_1$, $G_2$), where M(·) is a pre-known mathematical function. G' may also be called magnified matrix. In short, it is obtained by concatenating and aggregating $G_1$ and $G_2$. For example, for a graph $x_1$→$x_2$↔$x_3$, the corresponding matrices will be:

$$G_1 = \begin{pmatrix} 0 & 1 & 0 \\ 0 & 0 & 0 \\ 0 & 0 & 0 \end{pmatrix}$$

$$G_2 = \begin{pmatrix} 0 & 0 & 0 \\ 0 & 0 & 1 \\ 0 & 1 & 0 \end{pmatrix}$$

$$G' = \begin{pmatrix} 0 & 1 & 0 & 0 \\ 0 & 0 & 0 & 0 \\ 0 & 0 & 0 & 0 \\ 0 & 1 & 1 & 0 \end{pmatrix}$$

where the 4th row of G' corresponds to the 4th variable (additional latent confounder) implied in the bidirected edge $x_2$↔$x_3$. That is, the 4th variable should point to both $x_2$ and $x_3$, hence those two 1s in the second and third cell of the 4th row.

Under this idea, we model the causal graph G' jointly with the observations $x^1, \ldots, x^N$, as well as latent confounders $u^1, \ldots, u^N$:

$$p_\theta(x^1, \ldots, x^N, u^1, \ldots, u^N, G') = p(G')\prod_n p_\theta(x^n, u^n \mid G') \tag{5}$$

We will define constraints on G' and the parameterization of $p_\theta(x'', u''|G')$ later. We call Eq. (5) magnification-based parameterization, since the original ADMGs formulation does not explicitly assume any functional forms. To optimize θ and perform approximate inference on G', we define:

1) A variational distribution $q_\varphi(G)$ to approximate the intractable posterior $p_\theta(x^1, \ldots, x^N)$. Similar to the original DECI, this can be parametrized as the product of independent Bernoulli distributions for each potential directed edge in G'. We parametrize edge existence and edge orientation separately, using the ENCO parametrization.

2) An inference network $q_\lambda(u|x)$ to approximate the intractable posterior $p_\theta$, G'(u|x), e.g., a Gaussian inference network used in VAEs. The inference network $q_\lambda(u|x)$ has also been referred to as H earlier.

We use them to build the ELBO, given by:

$$ELBO(\theta, \phi, \lambda) = \tag{6}$$

$$\mathbb{E}_{q_\phi(G)q_\lambda(u|x)}\left[\log\frac{p(G)\prod_n p_\theta(x^n, u^n \mid G)}{q_\phi(G)\prod_n q_\lambda(u^n \mid x^n)}\right] \le \log p_\theta(x^1, \ldots, x^N)$$

By committing to optimize Eq. (6), we implicitly make the following assumptions:

We already know the exact number of unmeasured variables. That is, the latent vertexes U is given and fixed.

For all unmeasured variables in U, they only possess out-going edges. That is, all variables U serve as confounders. This in practice and be implemented by model.set graph constraint( ) in DECI code base.

Prior over ADMGs: The ADMG constraint on the graph G' can be imposed in two ways:

Directly apply the DAG constraint on G'. That is, $$h(G') = tr\left(e^{G'\odot G}\right) - D = 0 \tag{7}$$

This ensures that once G' can be converted to an ADMG (by marginalizing U and only keeping X).

OR

First marginalize G' to the graph G on X, and then apply ADMG constraints on G. This can be done via the following three ADMG constraints:

Ancestral ADMG constraint:

$$h(G) = tr\left(e^D\right) - D + \sum\left(e^{G_{directed}} \odot G_{bidirected}\right) = 0 \tag{8}$$

where $G_{directed,i,j}=1$ if and only if $x_i$←$x_j$; and $G_{bidirected,i,j}=1=G$ if and only if $x_i$↔$x_j$.

Arid ADMG constraint:

$$h(G) = tr\left(e^D\right) - D + GREENERY(G_{directed}, G_{bidirected}) = 0 \tag{9}$$

Bow-free constraint:

$$h(G) = tr\left(e^D\right) - D + \sum(G_{directed} \odot G_{bidirected}) = 0 \tag{10}$$

By using any of those constraints, p(G') can be implemented by:

$$p(G') \propto \exp(-\lambda_s \|G'\|_F^2 - \rho h(G')^2 - \alpha h(G'))  \qquad (11)$$

Parameterization of $p_\theta(x^n, u^n | G')$: Similar to DECI, we can parameterize $p_\theta(x^n, u^n | G')$ using auto-regressive ANM. That is, $z = g_{G'}(x, u; \theta) = [x, u] - f_{G'} \cdot Q([x, u]; \theta)$. Where z are independent noise variables following the distribution $\Pi_i p_{z_i}$. Then we can write the observational likelihood as:

$$p_\theta(x^n, u^n \mid G') = p_z(g_{G'}([x^n, u^n]; \theta)) = \prod_{i=1}^{D} p_{z_i}(g_{G'}([x^n, u^n]; \theta)_i)  \qquad (12)$$

where we omitted the Jacobian-determinant term because it is always equal to one for DAGs G'.

Structural identifiability under latent confounders: Preferably, we would like to find a set of suitable assumptions such that D-DECI should satisfy the structural identifiability definition, as follows.

Definition 1 (D-DECI Structural Identifiability). For a distribution $p_\theta(x;G') := \int_u p_\theta(x, u|G')du$, the graph G' is said to be structural identifiable from $p_\theta(x;G')$ if there exists no other distribution $p_\theta'(x;G'')$ such that $G' \neq G''$ and $p_\theta(x;G') = p_\theta'(x;G'')$.

Generally, such structural identifiability does not hold. However, under the constraint of bow-freeness, we will prove identifiability, which will be discussed in the next section.

D-DECI Identifiability

Notation and assumptions: Let $x \in \mathbb{R}^0$ denote the observed data, $u \in \mathbb{R}^D$ denote the unobserved data, $v = [x; u]^T$, and $p(x, u; g^0)$ the ground truth data generating distribution, where $g^0$ is a binary adjacency matrix representing the true causal DAG. DDECI uses the additive noise model (ANM) defining the structural assignment $x_j' = f_i(pa(j); \theta) + n_j$ where pa(j) denotes the parents of $x_j$. The function f corresponds to the decoders $g^d$ described earlier. We'll also use the notation $pa_x(j)$ and $pa_u(j)$ to denote the parents of $x_j$ in the observed and unobserved set, respectively. $n_j$ are mutually independent noise variables. The noise term n has also been referred to as z earlier.

Assumption 1 (Form of $f_j$): We assume that the functions $f_j$ are non-linear and decompose as:

$$f_j(pa_x(j), pa_u(j); \theta) = f_{j,x}(pa_x(j); \theta) + f_{j,u}(pa_u(j); \theta)  \qquad (13)$$

Assumption 2 (Unobserved variables are latent confounders): All unobserved variables are latent confounders of observed variables, i.e. have the causal structure $x_j \leftarrow u_k \rightarrow x_i$. Justification of this is given by the proposition that any latent variable can be reparameterised by absorbing exogenous noise to make it a latent confounder. A distribution p(x) satisfies minimality w.r.t. $g$ if it is Markov w.r.t. $g$, but no to any proper subgraph of $g$. Since we cannot access the true data generating distribution $p(x, u; g^0)$, only the marginal distribution over observed variables $p(x; g^0)$, we require a slightly different definition of minimality. We define this below.

Definition 1 (Minimality): $p(x; g)$ is minimal if it does not satisfy the local Markov condition with respect to the ADMG of any subgraph of $g$. This form of minimality implies the bow-free constraint. To see this, note that the causal structure $x_i \leftarrow u_k \rightarrow x_j$ together with $x_i \leftarrow x_j$, and $x_i \leftarrow u_k \rightarrow x_j$ alone imply the same conditional independencies. Since the latter is a subgraph of the former, only it satisfies the minimality condition.

Assumption 3 (Minimality): For a distribution $p(x; g)$ generated by D-DECI, we assume the minimality condition holds.

Comments on assumption of latent variables: Treatment effect is invariant to parameterisations if intervening on observed variables only.

Proof of structural identifiability: Here we prove structural identifiability of $g$ given the assumptions of the previous section.

Lemma 1: Let M denote a set of variables not containing $v_i$, and let $s(v_i)$ denote a linear or nonlinear function of $v_i$. Then, the residual of $s(v_i)$ regressed on M cannot be independent of $n_i$:

$$\forall M \subseteq V \setminus \{v_i\}, g_i, [S(v_i) - g_i(M) \not\!\perp\!\!\!\perp n_i]  \qquad (14)$$

Proof: Assume that $[s(v_i) - g_i(M) \perp\!\!\!\perp n_i]$ holds, then M must contain at least one descendent of $v_i$ as it must have dependence on the noise $n_i$ to cancel effect of $n_i$ in $s(v_i)$. We can express $g_i(M)$ as $u_i(\cup_{j:v_j \in M} n_j \cup n_i)$. Since $g_i$ operates on variables defined by non-linear transformations of the exogenous noise terms, we cannot express $u_i$ as $a_i(\cup_{j:v_j \in M} n_j) + b_i (n_i)$. M contains a descendent of $v_i$, so $\cup_{j:v_j \in M} n_j \cup n_i$ includes at least one noise term $n_k$ that satisfies $v_i \perp\!\!\!\perp n_k$ (i.e. is not in $v_i$). Thus, terms containing ni cannot be fully removed from $s(v_i) - g_i(M)$ and so $[s(v_i) - g_i(M) \perp\!\!\!\perp n_i]$ does not hold.

Lemma 2: If an only if is satisfied, there is a latent confounder, and no direct cause, between $x_i$ and $x_j$.

$$\forall g_i, g_j, M \subseteq (X \setminus \{x_i\}), N \subseteq (X \setminus \{x_j\}), [(x_i - g_i(M) \not\!\perp\!\!\!\perp (x_j - g_j(N)]  \qquad (15)$$

Proof: Define $g_i$ and $g_j$ as $g_i(M) = f_{i,x}(pa_x(i)) + g'_i(M)$ and $g_j(N) = f_{j,x}(pa_x(j)) + g'_j N$ respectively. Then, (15) becomes equivalent to:

$$[(f_{i,u}(pa_u(i)) + n_i - g'_i(M) \not\!\perp\!\!\!\perp (f_{j,u}(pa_u(j)) + n_j - g'_j(N)]  \qquad (16)$$

This is equivalent to:

$$(f_{i,u}(pa_u(i)) + n_i) \not\!\perp\!\!\!\perp (f_{j,u}(pa_u(j)) + n_j)  \qquad (17)$$

And since $n_i \perp\!\!\!\perp n_j$, we have:

$$(f_{i,u}(pa_u(i)) \not\!\perp\!\!\!\perp n_j) \vee (n_i \not\!\perp\!\!\!\perp f_{j,u}(pa_u(j))) \vee f_{i,u}(pa_u(i)) \not\!\perp\!\!\!\perp f_{j,u}(pa_u(j)))  \qquad (18)$$

The first implies the existence of an unobserved mediator between $x_j$ and $x_i$, the second implies the existence of an unobserved mediator between $x_i$ and $x_j$, and the third implies the existence of an unobserved confounder. Given Assumptions 2 and 3, this indicates the presence of a latent confounder and no direct cause between $x_i$ and $x_j$.

Lemma 3. If (19) is satisfied, there is no causal relationship between $x_i$ and $x_j$ and no latent confounder.

$$\exists\, g_i, g_j, M \subseteq (X\backslash\{x_i, x_j\}), N \subseteq (X\backslash\{x_i, x_j\}), \tag{19}$$

$$[(x_i - g_i(M) \perp\!\!\!\perp (x_j - g_j(N))]$$

Lemma 4. If (20) and (21) are satisfied, $x_j$ is a direct cause of $x_i$ and there is no latent confounder.

$$\forall\, g_i, g_j, M \subseteq (X\backslash\{x_i, x_j\}), N \subseteq (X\backslash\{x_j\}), [(x_i - g_i(M) \not\perp\!\!\!\perp (x_j - g_j(N)] \tag{20}$$

$$\exists\, g_i, g_j, [(x_i - g_i(M) \perp\!\!\!\perp (x_j - g_j(N))] \tag{21}$$

Thus, for any pair of variables we can determine whether there exists a latent confounder, and if not we can determine whether or not there is a direct cause and the orientation.

MLE recovers ground proof: We can use the exact same proof as in the DECI paper to show that MLE recovers ground truth—we can just replace $g$ with the ADMG corresponding to $g$ projected onto x.

D-DECI recovers ground truth: In the infinite data limit, we have:

$$\lim_{N\to\infty} \frac{1}{N}\sum_{n=1}^{N} \mathbb{E}_{q_\phi(G)q(u_n|x_n)}[\log p_\theta(x_n, u_n \mid \mathcal{G})] - \frac{1}{N}\sum_{n=1}^{N} H(q(u_n \mid x_n)) - \tag{22}$$

$$\underbrace{\frac{1}{N}KL[q(\mathcal{G})\|p(\mathcal{G})]}_{\to 0} = \lim_{N\to\infty} \frac{1}{N}\sum_{n=1}^{N} \mathbb{E}_{q_\phi(G)}[\log p_\theta(x_n \mid \mathcal{G})] -$$

$$\frac{1}{N}\sum_{n=1}^{N} \mathbb{E}_{q(\mathcal{G})}[KL[q(u_n \mid x_n)\|p(u_n \mid x_n, \mathcal{G})]].$$

The posterior approximation $q(u_n|x_n)$ should preferably be very accurate (i.e. $\mathbb{E}_{q(\mathcal{G})}[KL[q(u_n|u_x)\|p(u_n|u_x, \mathcal{G})]]\approx 0$) to recover the ground truth causal structure.

Final Remarks

It will be appreciated that the above embodiments have been described by way of example only.

More generally, according to a first aspect disclosed herein there is provided (Statement 1): a computer-implemented method comprising: A) selecting a selected variable from among variables of a feature vector; B) sampling a temporal causal graph from a temporal graph distribution, the temporal graph distribution specifying probabilities of directed causal edges between different ones of the variables of the feature vector at a present time step, and from one of the variables of the feature vector at a preceding time step to one of the variables of the feature vector at the present time step; C) from among of the variables of the feature vector, identifying a present parent which is a cause of the selected variable in the present time step according to the temporal causal graph, and identifying a preceding parent which is a cause of the selected variable from the preceding time step according to the temporal causal graph; D) inputting an input value of each of the identified present and preceding parent into a respective encoder, resulting in a respective embedding of each of the present and preceding parents; E) combining the embeddings of the present and preceding parents, resulting in a combined embedding; and F) inputting the combined embedding into a decoder associated with the selected variable, resulting in a reconstructed value of the selected variable.

In embodiments the method may optionally further comprise features as set out in any of the following Statements.

Statement 2. The method of Statement 1, wherein: the temporal causal graph distribution sampled in B) specifies probabilities of directed causal edges existing from each of a plurality of variables of the feature vector from one or more preceding time steps, each to a variable of the feature vector at the present time step; and C) comprises, from among of the variables of the feature vector, identifying each present parent that is a cause of the selected variable in the present time step according to the temporal causal graph, and identifying each preceding parent variable which is a cause of the selected viable from a preceding time step according to the temporal causal graph.

Statement 3. The method of Statement 2, further comprising: generating a history dependent noise term based on embeddings of the preceding parents; and combining the history dependent noise term with the reconstructed value of the selected variable, resulting in a simulated value of the reconstructed variable.

Statement 4. The method of Statement 3, wherein embeddings of the present parents are not input into the noise model.

Statement 5. The method of Statement 4, wherein the generating of the history dependent noise term comprises: combining the embeddings of the preceding parents, resulting in a further embedding; inputting the further embedding into a decoder associated with the selected variable, resulting in one or more parameter values; and generating the history dependent noise term from the probabilistic distribution as parameterized by the one or more parameter values.

Statement 6. The method of any preceding Statement, wherein: B) further comprises sampling a second causal graph from a second graph distribution, the second causal graph modelling presence of possible confounders, a confounder being an unobserved cause of both of two variables in the feature vector; C) further comprises, from among of the variables of the feature vector, identifying a parent variable which is a cause of the selected variable according to the first causal graph, and which together with the selected variable forms a confounded pair having a respective confounder being a cause of both according to the second causal graph; and D) further comprises inputting the input value of the parent variable and an input value of the selected variable into an inference network, resulting in a latent value modelling the respective confounder of the confounded pair, and inputting the latent value into a second encoder, resulting in an embedding of the confounder of the confounded pair; and in E) the combining includes combining the embedding of the present and preceding parents with the embedding of the confounder of the confounded pair, thereby resulting in said combined embedding.

Statement 7. The method of any of Statements 2 to 5, or Statement 6 when dependent on any of Statements 2 to 5, comprising: i) for a given training data point comprising a given combination of input values of the variables of the feature vector at the present times step and each preceding time step, repeating A)-F) over multiple selections, each selection selecting a different one of the variables of the feature vector as the selected variable thereby resulting in a respective reconstructed value, the multiple selections together thereby resulting in a reconstructed version of the training data point comprising the reconstructed values for the training data point; ii) evaluating a measure of difference between the training data point and the reconstructed version; and iii) training model parameters of the encoders, decoders, and temporal graph distributions, based on the evaluated measure.

Statement 8. The method of Statement 7, comprising repeating i)-iii) over multiple input data points, each comprising a different combination of input values of the variables of the feature vector.

Statement 9. The method of Statement 7 or 8, wherein: each selection in i) further comprises a history dependent noise model generating a respective history dependent noise term based on embeddings of the preceding parents; and wherein the training further comprises training model parameters the history dependent noise model based on the evaluated measure.

Statement 10. The method of Statement 9, wherein in each selection in i), the generating of the history dependent noise term by the history-dependent noise model comprises: combining the embeddings of the preceding parents, resulting in a respective further embedding; inputting the respective further embedding into the decoder associated with the selected variable, resulting in a one or more parameter values; and generating the respective history dependent noise term based on the one or more parameter values.

Statement 11. The method of Statement 10, comprising repeating i)-iii) over multiple input data points, each comprising a different combination of input values of the variables of the feature vector.

Statement 12. The method of Statement 2, or any of Statements 3 to 11 when dependent on Statement 2, comprising: I) setting the input value of an intervened-on variable of the feature vector, other than the selected variable, to a specified value; and II) estimating an effect of the intervened-on variable on the selected variable based on the reconstructed value of the selected variable.

Statement 13. The method of Statement 12, wherein: I) comprises setting the input value of a plurality of intervened-on variables of the feature vector, other than the selected variable, to respective specified values; and II) comprises estimating the effect of the plurality of intervened-on variables based on the reconstructed value of the selected variable.

Statement 14. The method of Statement 13, wherein: I) comprises repeating A)-F) over multiple rounds, each using the same selected variable and setting the intervened-on variable to the same specified value, but performing the sampling of the temporal causal graph afresh each round, thereby resulting in a respective reconstructed value of the selected variable from each round; and II) comprises determining an average treatment effect of the intervened-on variable on the selected variable averaged over the multiple rounds.

Statement 15. The method of Statement 14, wherein each graph-sampling event further comprises: generating a history dependent noise term based on the embeddings of the preceding parents; and combining the history dependent noise term with the reconstructed value of the selected variable, resulting in a simulated value of the reconstructed variable; wherein said estimating based on the reconstructed values in II) comprises: estimating the effect of the intervened-on variable on the selected variable based on the simulated values.

Statement 16. The method of Statement 14 or 15, wherein one or both of: each round sets a plurality of intervened-on variables and/or observed variables of the feature vector to specified values (and in the case of multiple intervened-on variables, II comprises determining the average treatment effect of the plurality of intervened-on variables on the selected variable); and/or each round comprises an interior loop of D)-F) repeated around multiple iterations with the same sampled graph but for incrementing values of the present time step with each iteration, wherein each but the last iteration comprises, in addition to the target variable, reconstructing or simulating values of one or more further variables of the feature vector, and feeding back the simulated or reconstructed values as the specified input values of the next iteration.

Statement 17. The method of any of Statements 12 to 16, wherein the intervened-on variable models a treatment on a real-world entity or an environment thereof and the target variable models an effect of the treatment applied to the real-world entity, and the method further comprises actioning the treatment on the real-world entity in dependence on the estimated treatment effect.

Statement 18. The method of Statement 17, wherein one of: the real-world entity comprises a living being, and the treatment comprises a medical treatment to the living being or an environment thereof; or the real-world entity comprises a mechanical, electrical or electronic device or system, or an environment thereof; and the treatment comprises an act of maintaining, debugging, upgrading or controlling the device or system, or controlling the environment thereof; or the real-world entity comprises a network or software, and the treatment comprises an act of controlling the network or software.

Statement 19. A system comprising: processing apparatus comprising one or more processors; and memory comprising one or more memory units, wherein the memory stores: a machine learning model comprising the encoder and decoders of any preceding Statement, and optionally the noise model and/or a inference network; and code arranged to run on the processing apparatus and being configured so as when run to perform the method of any of Statements 1 to 18.

Statement 20. A computer program embodied on non-transitory computer-readable storage, wherein the computer program comprises instructions configured so as when run on one or more processors to perform the method of any of Statements 1 to 18.

According to a second aspect disclosed herein there is provided (Statement 1A) a computer-implemented method comprising: a) selecting a selected variable from among variables of a feature vector; b) sampling a first causal graph from a first graph distribution and sampling a second causal graph from a second graph distribution, the first causal graph modelling causation between variables in the feature vector, and the second causal graph modelling presence of possible confounders, a confounder being an unobserved cause of both of two variables in the feature vector; c) from among of the variables of the feature vector, identifying a parent variable which is a cause of the selected variable according to the first causal graph, and which together with the selected variable forms a confounded pair having a respective confounder being a cause of both according to the second causal graph; d) inputting an input value of the parent variable into a first encoder, resulting in a respective embedding of the parent variable; e) inputting at least the input value of the parent variable (and optionally also an input value of the selected variable and/or an input value of one or more others of the variables of the feature vector) into an inference network, resulting in a latent value modelling the respective confounder of the confounded pair, and inputting the latent value into a second encoder, resulting in an embedding of the confounder of the confounded pair; f) combining the embedding of the parent variable with the embedding of the confounder of the confounded pair, resulting in a combined embedding; and g) inputting the combined embedding into a decoder, resulting in a reconstructed value of the selected variable.

In embodiments there may optionally be provided a method in accordance with any of the following statements.

Statement 2A. The method of Statement 1A, wherein c) comprises: identifying each of the variables of the feature vector that is a respective parent variable of the selected variable according to the first causal graph, and identifying each respective confounded pair that comprises the selected variable and a respective one of the identified parent variables according to the second causal graph; d) comprises: inputting a respective input value of each of the parent variables into a respective first encoder for the parent, resulting in a respective embedding of each respective parent variable; e) comprises: for each identified confounded pair, inputting the input value of the respective parent variable and the input value of the selected variable into the inference network, thereby resulting in a respective latent value of each of the respective confounders, and inputting each of the latent values into a respective second encoder for the respective latent value, resulting in a respective embedding of each of the respective confounders; f) comprises combining the embeddings of all the identified parent variables and confounders together, thereby resulting in said combined embedding; and g) comprises inputting the combined embedding into a respective decoder associated with the selected variable, resulting in a reconstructed value of the selected variable.

Statement 3A. The method of Statement 2A, comprising: i) for a given training data point comprising a given combination of input values of the variables of the feature vector, repeating a)-g) over multiple selections, each selection selecting a different one of the variables of the feature vector as the selected variable thereby resulting in a respective reconstructed value, the multiple selections together thereby resulting in a respective reconstructed version of the training data point comprising the reconstructed values for the training data point; ii) evaluating a measure of difference between the training data point and the reconstructed version; and iii) training parameters of the inference network, first and second encoders, decoders, and first and second graph distributions, based on the evaluated measure.

Statement 4A. The method of Statement 3A, comprising repeating i)-iii) over multiple input data points, each comprising a different combination of input values of the variables of the feature vector.

Statement 5A. The method of Statement 4A, comprising, after the training over the multiple training data points, observing the second graph distribution to estimate whether a confounder exists between a target pair of the variables of the feature vector.

Statement 6A. The method of Statement 5A, comprising, after the training over the multiple training data points, observing the latent value of the respective confounder between the target pair of variables, resulting from the inference network, as an estimated value of the respective confounder.

Statement 7A. The method of Statement 5A or 6A, wherein the variables of the feature vector model properties of a real-world entity or an environment thereof, and the method comprises, in dependence in said estimating of whether a confounder exists between the target pair of variables, determining whether or not to apply a treatment to one of said target pair of variables to affect the other of said target pair of variables.

Statement 8A. The method of Statement 7A, wherein one of: the real-world entity comprises a living being, and the treatment comprises a medical treatment to the living being or the environment thereof; or the real-world entity comprises a mechanical, electrical or electronic device or system, or an environment thereof; and the treatment comprises an act of maintaining, debugging, upgrading or controlling the device or system, or controlling the environment thereof; or the real-world entity comprises a network or software, and the treatment comprises an act of controlling the network or software.

Statement 9A. The method of any of Statements 2A to 8A, comprising: I) setting the input value of an intervened-on variable of the feature vector, other than the selected variable, to a specified value; and II) estimating an effect of the intervened-on variable on the selected variable based on the reconstructed value of the selected variable.

Statement 10A. The method of Statement 9A, wherein: I) comprises setting the input value of a plurality of intervened-on variables of the feature vector, other than the selected variable, to respective specified values; and II) comprises estimating the effect of the plurality of intervened-on variables based on the reconstructed value of the selected variable.

Statement 11A. The method of Statement 9A or 10A, wherein: I) comprises repeating a)-g) over multiple graph-sampling events, each using the same selected variable and setting the intervened-on variable to the same specified value, but performing the sampling of the first and second causal graphs afresh each time, thereby resulting in a respective reconstructed value of the selected variable from each graph-sampling events; and II) comprises determining an average treatment affect of the intervened-on variable on the selected variable averaged over the multiple graph-sampling events.

Statement 12A. The method of Statement 11A, wherein each graph-sampling event sets a plurality of intervened-on values to specified values, the same values each time; and II) comprises determining the average treatment effect of the plurality of intervened-on variables on the selected variable.

Statement 13A. The method of Statement 9A, wherein the intervened-on variable models a treatment on a real-world entity or an environment thereof and the target variable models an effect of the treatment applied to the real-world entity, and the method further comprises actioning the treatment on the real-world entity in dependence on the estimated treatment effect.

Statement 14A. The method of Statement 13A, wherein one of: the real-world entity comprises a living being, and the treatment comprises a medical treatment to the living being or an environment thereof; or the real-world entity comprises a mechanical, electrical or electronic device or system, or an environment thereof; and the treatment comprises an act of maintaining, debugging, upgrading or controlling the device or system, or controlling the environment thereof; or the real-world entity comprises a network or software, and the treatment comprises an act of controlling the network or software.

Statement 15A. The method of any of Statements 2A to 14A, wherein the inference network comprises a respective constituent inference network for each pair of variables in the feature vector, and e) comprises: for each identified confounded pair, inputting the input value of the respective parent variable and the input value of the selected variable into the respective inference network for the respective confounded pair, thereby resulting in the respective latent value of the respective confounder. Alternatively the inference network may comprise a common inference network operable to encode all the variables of the feature vector together into the respective latent for each pair.

Statement 16A. The method of any of Statements 2A to 15A, wherein each of the first and second encoders and each of the decoders comprises a neural network.

Statement 17A. The method of any of Statements 1A to 16A, wherein the inference network comprises a neural network.

Statement 18A. The method of Statement 9A or any subsequent Statement when dependent thereon, wherein the method is performed on a server system of a first party, the server system comprising one or more server units at one or more sites; and the method further comprises, by the server system of the first party: providing an application programming interface, API, enabling a second party to contact the server system via a network; receiving a request from the second party over the network via the API; in response to the request, determining the estimated treatment effect on the target variable; and returning the estimated treatment effect to the second party over the network via the API.

Statement 19A. A computer program embodied on computer-readable storage, wherein the computer program comprises a machine learning model comprising a plurality of first encoders, a plurality of second encoders, a decoder and an inference network; and wherein the computer-program further comprises instructions configured so as when run on one or more processors to perform the method of any of Statements 1A to 18A.

Statement 20A. A system comprising: processing apparatus comprising one or more processors; and memory comprising one or more memory units, wherein the memory stores: a machine learning model comprising the first encoders, second encoders, decoders, and inference network of any preceding Statement; and code arranged to run on the processing apparatus and being configured so as when run to perform the method of any of Statements 1A to 18A.

The first aspect (Statement 1) or any embodiment thereof may be used independently or in conjunction with the second aspect (Statement 1A) or any embodiment thereof.

In some examples, the model 104/104'/104" and associated computer executable instructions are provided using any computer-readable media that are accessible by the computing equipment 102. Computer-readable media include, for example, computer storage media such as memory and communications media. Computer storage media include volatile and non-volatile, removable, and non-removable media implemented in any method or technology for storage of information such as computer readable instructions, data structures, program modules or the like. Computer storage media include, but are not limited to, Random Access Memory (RAM), Read-Only Memory (ROM), Erasable Programmable Read-Only Memory (EPROM), Electrically Erasable Programmable Read-Only Memory (EEPROM), persistent memory, phase change memory, flash memory or other memory technology, Compact Disk Read-Only Memory (CD-ROM), digital versatile disks (DVD) or other optical storage, magnetic cassettes, magnetic tape, magnetic disk storage, shingled disk storage or other magnetic storage devices, or any other non-transmission medium that can be used to store information for access by a computing apparatus. In contrast, communication media may embody computer readable instructions, data structures, program modules, or the like in a modulated data signal, such as a carrier wave, or other transport mechanism. As defined herein, computer storage media do not include communication media. Therefore, a computer storage medium should not be interpreted to be a propagating signal per se. Propagated signals per se are not examples of computer storage media. Although the computer storage medium may be described within the computing equipment 102, it will be appreciated by a person skilled in the art, that, in some examples, the storage is distributed or located remotely and accessed via a network or other communication link (e.g., using a communication interface).

Other variants or use cases of the disclosed techniques may become apparent to the person skilled in the art once given the disclosure herein. The scope of the disclosure is not limited by the described embodiments but only by the accompanying claims.

The invention claimed is:

1. A computer-implemented method comprising:
   selecting a variable from among variables of a feature vector;
   sampling a temporal causal graph from a temporal graph distribution, the temporal graph distribution specifying probabilities of directed causal edges between different ones of the variables of the feature vector at a present time step, and from one of the variables of the feature vector at a preceding time step to one of the variables of the feature vector at the present time step;
   from among the variables of the feature vector, identifying a present parent which is a cause of the selected variable in the present time step according to the temporal causal graph, and identifying a preceding parent which is a cause of the selected variable from the preceding time step according to the temporal causal graph;
   inputting input values of the present parent and the preceding parent into a respective encoder of a machine learning model, resulting in embeddings of the present and preceding parents;
   combining the embeddings of the present parent and the preceding parent, resulting in a combined embedding;
   inputting the combined embedding into a decoder associated with the selected variable, resulting in a reconstructed value of the selected variable, the machine learning model including the decoder;
   setting input values of a plurality of intervened-on variables of the feature vector, other than the selected variable, to respective specified values;
   estimating an effect of the plurality of intervened-on variables on the selected variable based on the reconstructed value of the selected variable;
   determining a reconstruction loss based on the effect of the plurality of intervened-on variables on the selected variable; and
   updating parameters of the encoder and the decoder of the machine learning model based on the reconstruction loss.

2. The method of claim 1, wherein the machine learning model is a trained machine learning model, the method further comprising:
   receiving a request to estimate an effect of the selected variable, the request including the input values of the plurality of intervened-on variables.

3. The method of claim 2, further comprising:

controlling the machine learning model to generate samples of the selected variable based on the input values of the plurality of intervened-on variables.

4. The method of claim 1, wherein each variable models a treatment on a real-world entity or an environment thereof and an effect of the treatment applied to the real-world entity, and the method further comprises actioning the treatment on the real-world entity based on the estimated effect of the treatment.

5. The method of claim 4, wherein one of:

the real-world entity comprises a living being, and the treatment comprises a medical treatment to the living being or an environment thereof;

the real-world entity comprises a mechanical, electrical or electronic device or system, or an environment thereof, and the treatment comprises an act of maintaining, debugging, upgrading or controlling the device or system, or controlling the environment thereof, or the real-world entity comprises a network or software, and the treatment comprises an act of controlling the network or software.

6. The method of claim 1, wherein the feature vector represents sensor measurements collected from a physical system, wherein the updated parameters of the encoder and the decoder of the machine learning model are used to control operations of the physical system.

7. The method of claim 1, wherein:

setting the input values comprises repeating the selecting, the sampling, the identifying, the inputting the input values, the combining, and the inputting the combined embedding over multiple rounds, each using the same selected variable and setting the intervened-on variable to the same specified value, and performing the sampling of the temporal causal graph afresh in each round, thereby resulting in a respective reconstructed value of the selected variable from each round; and estimating the effect comprises determining an average treatment effect of the plurality of intervened-on variables on the selected variable averaged over the multiple rounds.

8. The method of claim 7, wherein each round further comprises:

generating a history dependent noise term based on the embeddings of the preceding parents; and combining the history dependent noise term with the reconstructed value of the selected variable, resulting in a simulated value of the reconstructed variable;

wherein said estimating based on the reconstructed values comprises: estimating the effect of the plurality of intervened-on variables on the selected variable based on the simulated values.

9. The method of claim 8, wherein the generating of the history dependent noise term comprises:

combining the embeddings of the preceding parents, resulting in a further embedding;

inputting the further embedding into the decoder associated with the selected variable, resulting in one or more parameter values; and generating the history dependent noise term based on the one or more parameter values.

10. The method of claim 7, wherein:

each round sets a plurality of intervened-on variables and/or observed variables of the feature vector to specified input values; and each round comprises an interior loop of the inputting the input values, the combining, and the inputting the combined embedding repeated around multiple iterations with the same sampled graph but for incrementing values of the present time step with each iteration, wherein each but the last iteration comprises reconstructed or simulated values of one or more further variables of the feature vector, and feeding back the simulated or reconstructed values as the specified input values of the next iteration.

11. The method of claim 1, further comprising:

generating a history dependent noise term for the selected variable based on embeddings of the preceding parents; and combining the history dependent noise term with the reconstructed value of the selected variable, resulting in a simulated value of the reconstructed variable.

12. The method of claim 11, wherein embeddings of the present parents are not used to generate the history dependent noise term for the selected variable.

13. The method of claim 11, wherein the generating of the history dependent noise term comprises:

combining the embeddings of the preceding parents, resulting in a further embedding;

inputting the further embedding into the decoder associated with the selected variable, resulting in one or more parameter values; and generating the history dependent noise term based on the one or more parameter values.

14. The method of claim 1, wherein:

the sampling further comprises sampling a second causal graph from a second graph distribution, the second causal graph modelling presence of possible confounders, a confounder being an unobserved cause of both of two variables in the feature vector;

the identifying further comprises, from among the variables of the feature vector, identifying a parent variable which is a cause of the selected variable according to the temporal causal graph, and which together with the selected variable forms a confounded pair having a respective confounder being a cause of both according to the second causal graph;

the inputting the input values further comprises inputting the input value of the parent variable and an input value of the selected variable into an inference network, resulting in a latent value modelling the respective confounder of the confounded pair, and inputting the latent value into a second encoder, resulting in an embedding of the confounder of the confounded pair; and the combining includes combining the embeddings of the present and preceding parents with the embedding of the confounder of the confounded pair, thereby resulting in said combined embedding.

15. The method of claim 1, comprising:

for a given training data point comprising a given combination of input values of the variables of the feature vector at the present time step and each preceding time step, repeating the selecting, the sampling, the identifying, the inputting the input values, the combining, and the inputting the combined embedding over multiple selections, each selection selecting a different one of the variables of the feature vector as the selected variable thereby resulting in a respective reconstructed value, the multiple selections together thereby resulting in a reconstructed version of the training data point comprising the reconstructed values for the training data point;

evaluating a measure of difference between the training data point and the reconstructed version; and training model parameters of the encoders, decoders, and temporal graph distributions, based on the evaluated measure.

16. The method of claim 15, comprising repeating the repeating, the evaluating, and the training over multiple input data points, each comprising a different combination of input values of the variables of the feature vector.

17. The method of claim 15, wherein:

each selection in the repeating further comprises a history dependent noise model generating a respective history dependent noise term based on embeddings of the preceding parents;

wherein the training further comprises training model parameters of the history dependent noise model based on the evaluated measure.

18. The method of claim 17, wherein in each selection in the repeating, the generating of the history dependent noise term by the history dependent noise model comprises:

combining the embeddings of the preceding parents, resulting in a respective further embedding;

inputting the respective further embedding into the decoder associated with the selected variable, resulting in one or more parameter values; and generating the respective history dependent noise term based on the one or more parameter values.

19. A system comprising:

processing apparatus comprising one or more processors; and memory comprising one or more memory units, wherein the memory stores:

a machine learning model comprising a plurality of encoders and a plurality of decoders, and code arranged to run on the processing apparatus and being configured so as when run to perform a method comprising:

selecting a variable from among variables of a feature vector;

sampling a temporal causal graph from a temporal graph distribution, the temporal graph distribution specifying probabilities of directed causal edges between different ones of the variables of the feature vector at a present time step, and probabilities of causal edges existing from each of a plurality of variables of the feature vector at one or more preceding time steps to one or more variables of the feature vector at the present time step;

from among the variables of the feature vector, identifying a present parent which is a cause of the selected variable in the present time step according to the sampled temporal causal graph, and identifying a preceding parent which is a cause of the selected variable from any preceding time step according to the sampled temporal causal graph;

inputting input values of the present parent and the preceding parent into a respective one of the encoders of the machine learning model, resulting in a respective embedding of the present and preceding parents;

combining the embeddings of the present and preceding parents, resulting in a combined embedding;

inputting the combined embedding into a respective one of the decoders associated with the selected variable, resulting in a reconstructed value of the selected variable, the machine learning model including the decoder;

setting input values of a plurality of intervened-on variables of the feature vector, other than the selected variable, to respective specified values;

estimating an effect of the plurality of intervened-on variables on the selected variable based on the reconstructed value of the selected variable;

determining a reconstruction loss based on the effect of the plurality of intervened-on variables on the selected variable; and updating parameters of the encoders and the decoders of the machine learning model based on the reconstruction loss.

20. A computer program embodied on non-transitory computer-readable storage, wherein the computer program comprises instructions configured so as when run on one or more processors to perform a method comprising:

selecting a variable from among variables of a feature vector;

sampling a temporal causal graph from a temporal graph distribution, the temporal graph distribution specifying probabilities of directed causal edges between different ones of the variables of the feature vector at a present time step, and probabilities of causal edges existing from each of a plurality of variables of the feature vector at one or more preceding time steps to one or more variables of the feature vector at the present time step;

from among the variables of the feature vector, identifying a present parent which is a cause of the selected variable in the present time step according to the sampled temporal causal graph, and identifying a preceding parent which is a cause of the selected variable from any preceding time step according to the sampled temporal causal graph;

inputting input values of the present parent and the preceding parent into a respective first encoder of a machine learning model, resulting in a respective embedding of the present and preceding parents;

combining the embeddings of the present and preceding parents, resulting in a combined embedding;

inputting the combined embedding into a decoder associated with the selected variable, resulting in a reconstructed value of the selected variable, the machine learning model including the decoder;

setting input values of a plurality of intervened-on variables of the feature vector, other than the selected variable, to respective specified values;

estimating an effect of the plurality of intervened-on variables on the selected variable based on the reconstructed value of the selected variable;

determining a reconstruction loss based on the effect of the plurality of intervened-on variables on the selected variable; and updating parameters of the encoders and the decoders of the machine learning model based on the reconstruction loss.

* * * * *